US008188256B2

(12) United States Patent
Ishikawa

(10) Patent No.: US 8,188,256 B2
(45) Date of Patent: May 29, 2012

(54) **PRIMER AND PROBE FOR DETECTION OF *MYCOBACTERIUM INTRACELLULARE***

(75) Inventor: Tomokazu Ishikawa, Hyogo (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 233 days.

(21) Appl. No.: 12/298,525

(22) PCT Filed: Apr. 27, 2007

(86) PCT No.: PCT/JP2007/059251
§ 371 (c)(1),
(2), (4) Date: Oct. 24, 2008

(87) PCT Pub. No.: WO2007/129628
PCT Pub. Date: Nov. 15, 2007

(65) Prior Publication Data
US 2009/0275026 A1    Nov. 5, 2009

(30) Foreign Application Priority Data

May 2, 2006   (JP) ................................. 2006-128046

(51) Int. Cl.
*C12Q 1/68* (2006.01)
*C12P 19/34* (2006.01)
*C07H 21/02* (2006.01)
*C07H 21/04* (2006.01)

(52) U.S. Cl. ..................... 536/24.32; 435/6.1; 435/6.11; 435/6.12; 435/6.15; 536/23.1; 536/23.7; 536/24.33

(58) Field of Classification Search .................... None
See application file for complete search history.

(56) References Cited

U.S. PATENT DOCUMENTS

| 5,494,796 | A  | * | 2/1996 | Spears et al. ................ 435/6.15 |
| 5,681,705 | A  |   | 10/1997 | Schram et al. |
| 5,691,143 | A  |   | 11/1997 | Bustos et al. |
| 5,840,488 | A  |   | 11/1998 | Hogan |
| 5,866,336 | A  | * | 2/1999 | Nazarenko et al. ................ 435/6 |
| 6,022,542 | A  | * | 2/2000 | Rose et al. ................ 424/186.1 |
| 6,183,952 | B1 | * | 2/2001 | Billing-Medel et al. .......... 435/6 |
| 6,465,638 | B2 |   | 10/2002 | Gorman et al. |
| 6,582,908 | B2 | * | 6/2003 | Fodor et al. ................ 506/9 |
| 6,706,867 | B1 | * | 3/2004 | Lorenz ................ 536/23.1 |
| 6,919,180 | B2 | * | 7/2005 | Gunning et al. ................ 435/6 |
| 2001/0019822 | A1 |   | 9/2001 | Gorman et al. |
| 2004/0033547 | A1 | * | 2/2004 | Field et al. ................ 435/7.32 |
| 2004/0077565 | A1 | * | 4/2004 | Pavco et al. ................ 514/44 |
| 2004/0110129 | A1 | * | 6/2004 | Fischer et al. ................ 435/6 |
| 2006/0051769 | A1 | * | 3/2006 | Barts ................ 435/6 |
| 2009/0275026 | A1 |   | 11/2009 | Ishikawa |

FOREIGN PATENT DOCUMENTS

| JP | A-2001-103986 | 7/1996 |
| JP | A-H10-4984 | 3/1997 |
| JP | A-H11-6999 | 6/1998 |
| JP | A-10-323189 | 12/1998 |
| JP | B-3111213 | 9/2000 |
| JP | A-2001-299354 | 10/2001 |
| JP | A-2003-135099 | 5/2003 |
| JP | A-2003-284565 | 10/2003 |
| JP | A-2005-204582 | 8/2005 |
| JP | A-2006-61155 | 3/2006 |
| WO | WO 2004/067702 A2 | 8/2004 |
| WO | WO2005/103249 A1 | 3/2005 |
| WO | WO2006/029014 A2 | 3/2006 |
| WO | WO2007/129628 A1 | 11/2007 |

OTHER PUBLICATIONS

Extended European Search Report dated Dec. 9, 2009, for European Patent Application No. 07742686.4 (12 pages) (including the Supplementary European Search Report and the European Search Opinion).
Saito et al., "Identification of Various Serovar Strains of *Mycobacterium avium* Complex by Using DNA Probes Specific for *Mycobacterium avium* and *Mycobacterium intracellulare*," *J. Clin. Microbiol*, 28(8): 1694-1697 (1990).
Yamamoto et al., "Polymerase chain reaction for the differentiation of *Mycobacterium intracellulare* and *Mycobacterium avium*", *Tubercle and Lung Disease*, 74: 342-345 (1993).
Yamazaki et al., "Identification of *Mycobacterium intracellulare* by a polymerase chain reaction using species-specific primers," *Tubercle and Lung Disease*, 76: 330-335 (1995).
Database EMBL [Online], "*Mycobacterium intracellulare* gtfB, drrC, genes for glycosyl transferase, putative glycosyltransferase, putative acyltransferase, putative methyltransferase, hypothetical proteins, DegT/DnrJ/EryCI/StrS aminotransferase, putative glycosyltransferase, daunorubicin resistance protein C, complete cds.," created May 8, 2008; last updated May 8, 2008; XP-002556511; Accession No. AB355138.

(Continued)

*Primary Examiner* — Carla Myers
(74) *Attorney, Agent, or Firm* — Finnegan, Henderson, Farabow, Garrett & Dunner, LLP

(57) ABSTRACT

The present invention discloses an oligonucleotide which comprises a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene; a primer or a probe for the detection of *M. intracellulare*, which comprises the aforementioned oligonucleotide; and a method for detection of *M. intracellulare* using the aforementioned primer and/or the probe.

According to the detection method of the present invention, any false-positive result in diagnosis can be eliminated and detection or diagnosis of *M. intracellulare* can be carried out with higher accuracy, more preciseness, and more specifically compared to a conventional diagnostic method employing a cell culture assay or a PCR assay. The method also enables to quantify a microbial cell.

10 Claims, 9 Drawing Sheets

OTHER PUBLICATIONS

Poly, Frederic et al. Journal of Bacteriology, 2004, vol. 186, No. 14, p. 4781-4795.

De Beenhouwer, Hans, et al, Detection and identification of Mycobacteria by DNA Amplification and Oligonucleotide-Specific Capture Plate Hybridization, Journal of Clinical Microbiology, vol. 33(11), p. 2994-2998,1995, American Society for Microbiology.

PCT/ISA/237, English Translation of Written Opinion from the International Search Authority, for PCT/JP2009/059593, dated Aug. 11, 2009.

PCT/IB/373, English Translation of International Preliminary Report on Patentability, from the Patent Cooperation Treaty, for PCT/JP2009/059593, dated Jan. 11, 2011.

PCT/IB/338, PCT/IB/373, PCT/IB/237 International Preliminary Report on Patentability for PCT/JP2007/059251, English translation, mailed Nov. 27, 2008.

Extended European Search Report mailed Jan. 12, 2012, for European Patent Application No. 09754689.9—2401, PCT/JP2009/059593, (10 pgs.) (including the Supplementary European Search Report and the European Search Opinion).

Database EMBL [Online], "WLB1414G08.ab1 WLtestis Gallus gallus cDNA 5', mRNA sequence," created Apr. 4, 2004; last updated Feb. 8, 2011; Accession No. CN237871.

* cited by examiner

[Fig.1]
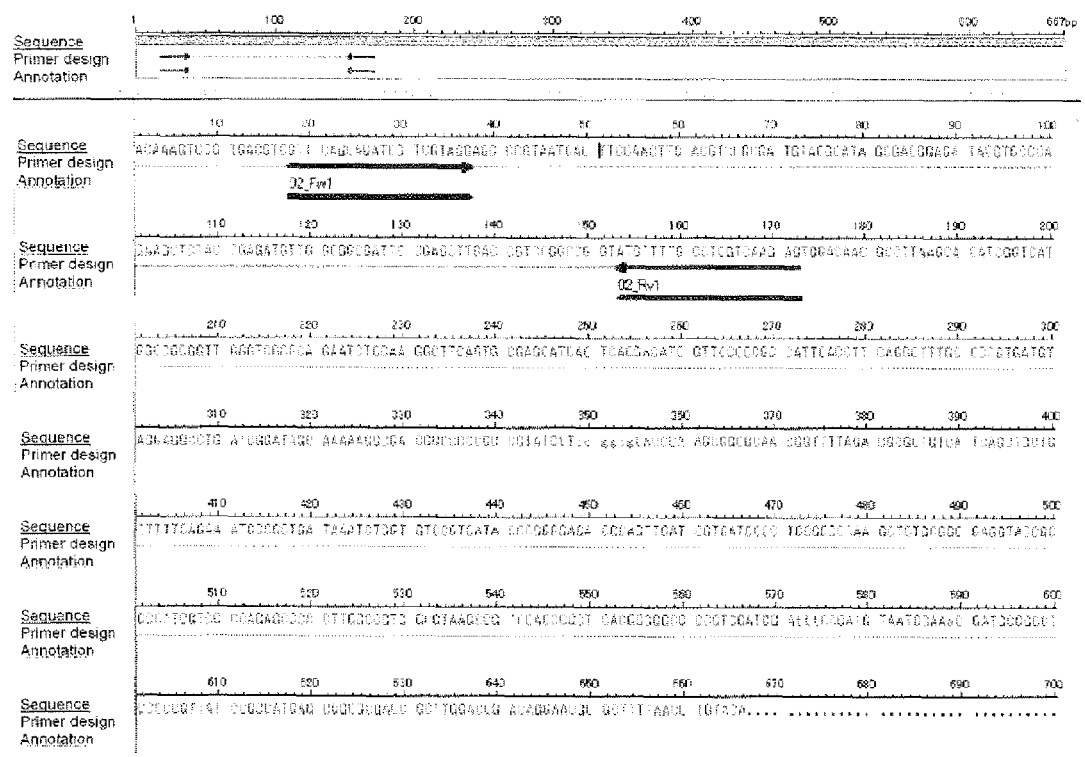

[Fig.2]
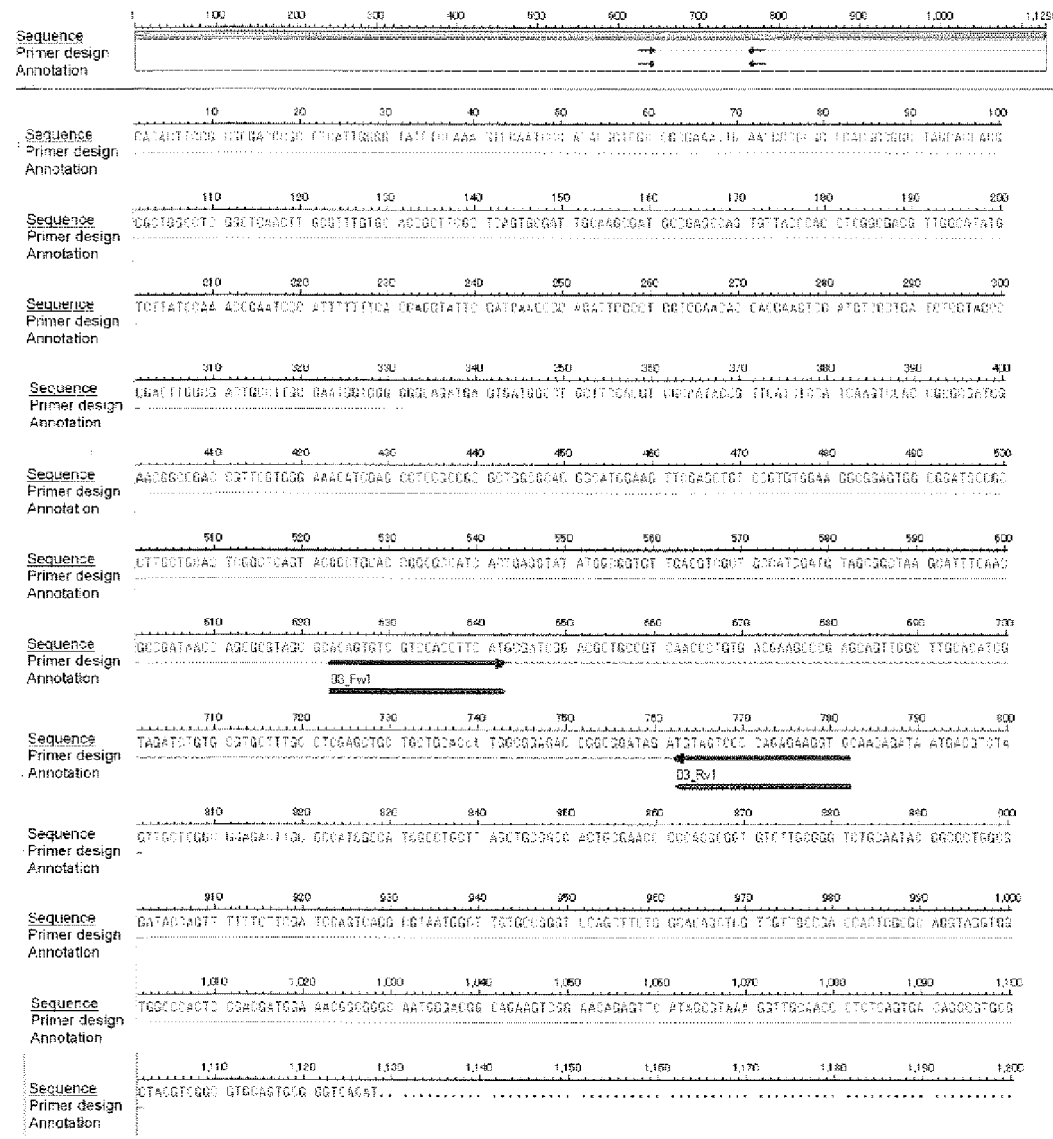

[Fig.3]
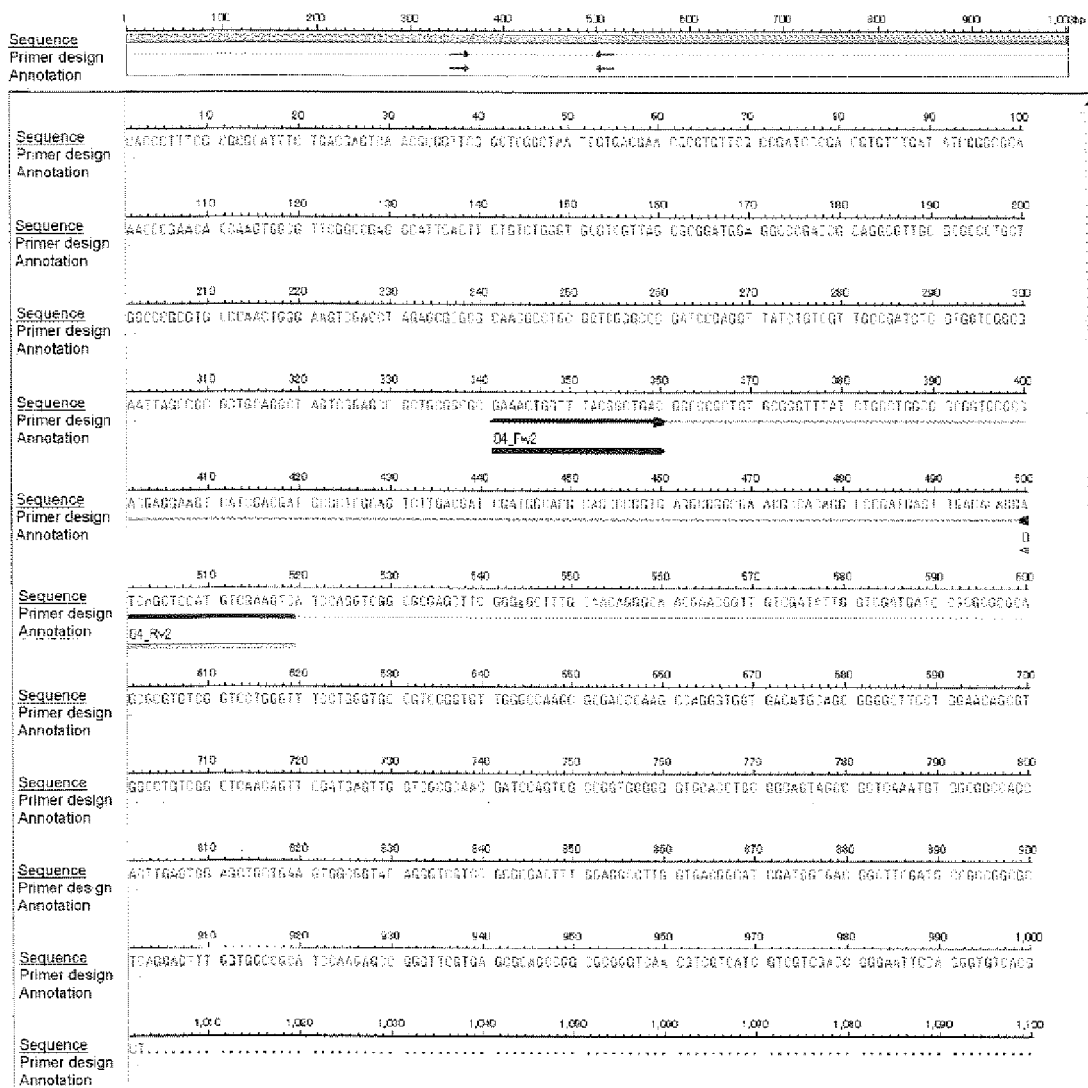

[Fig.4]
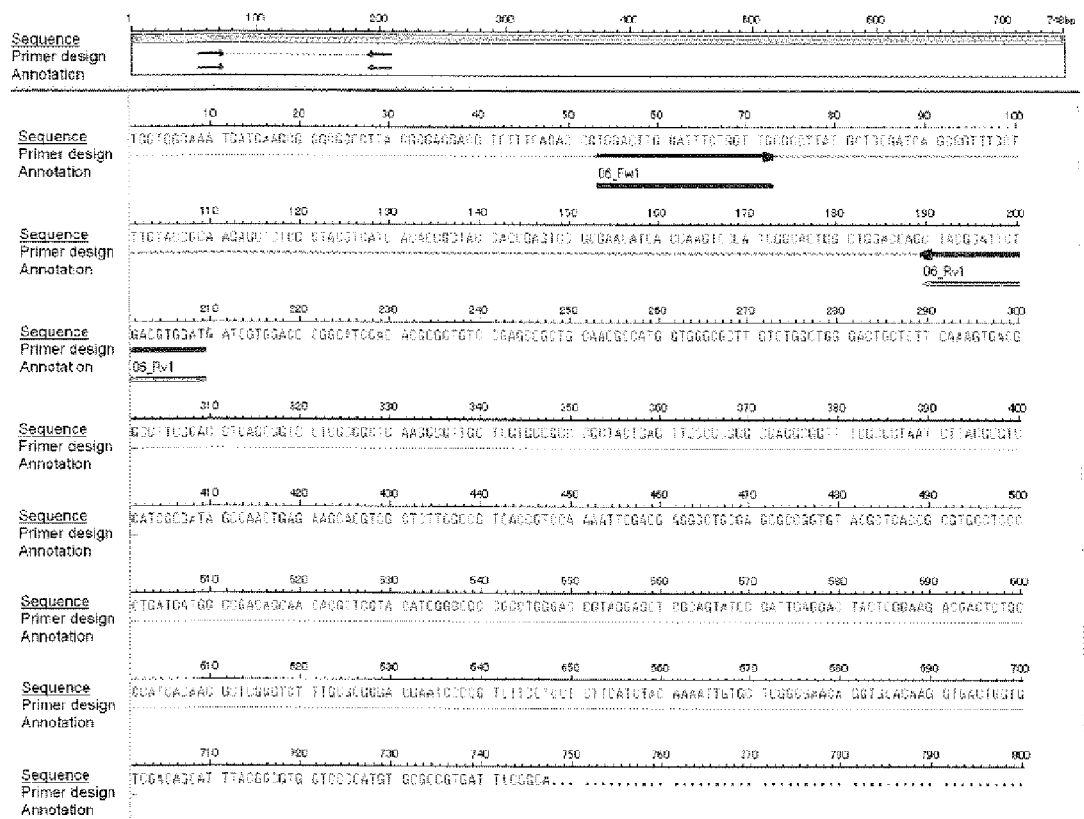

[Fig.5]
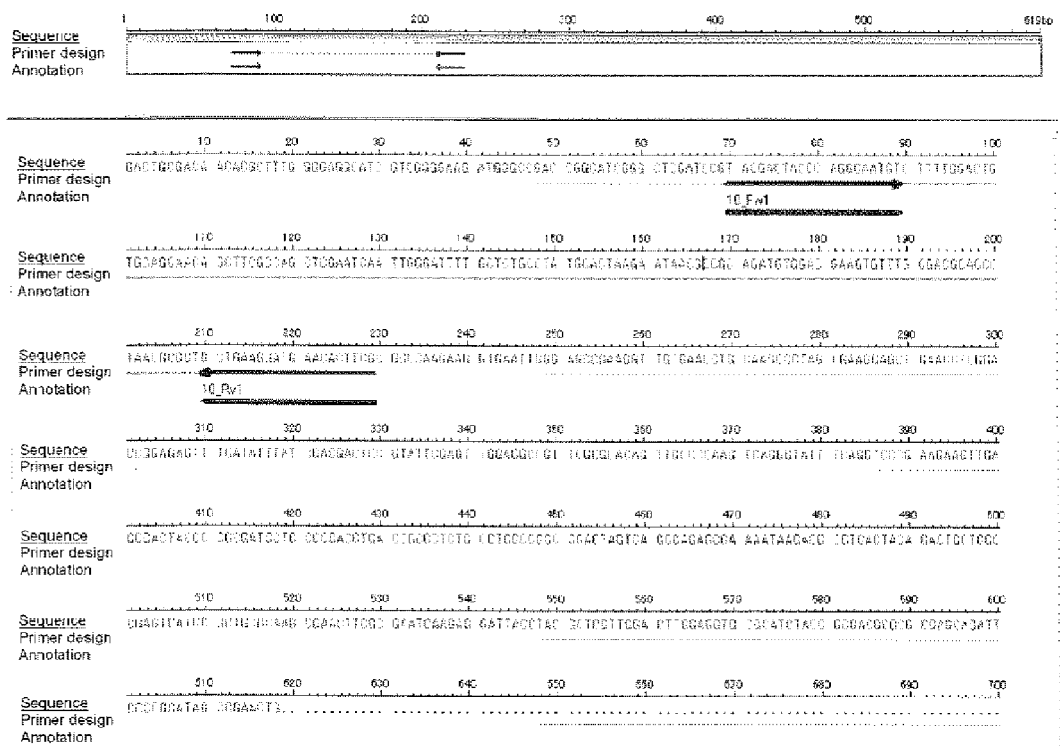

[Fig.6]
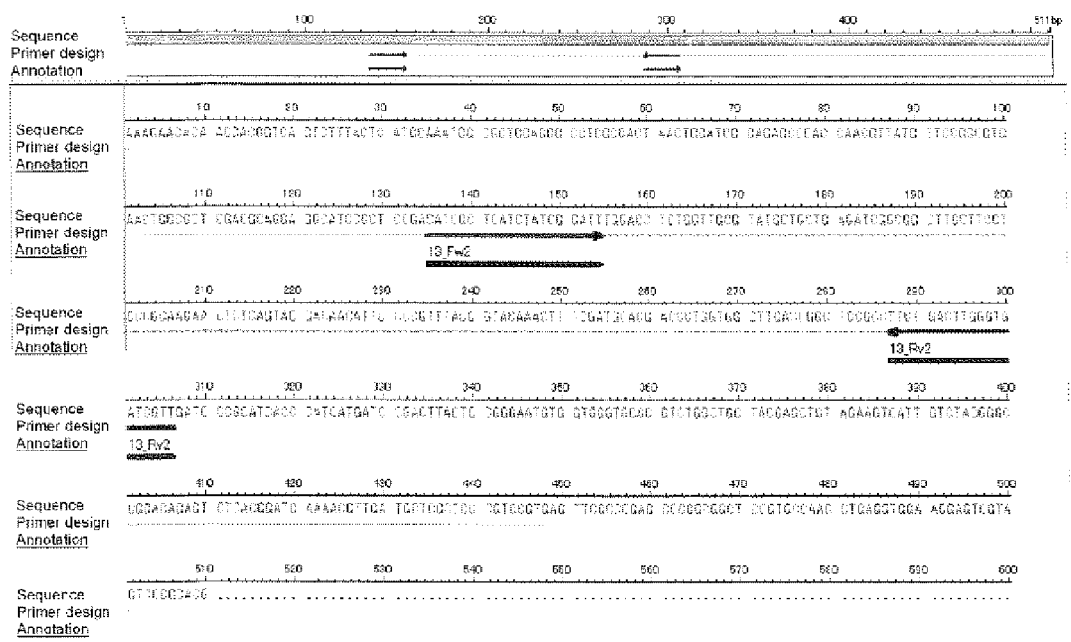

[Fig. 7]
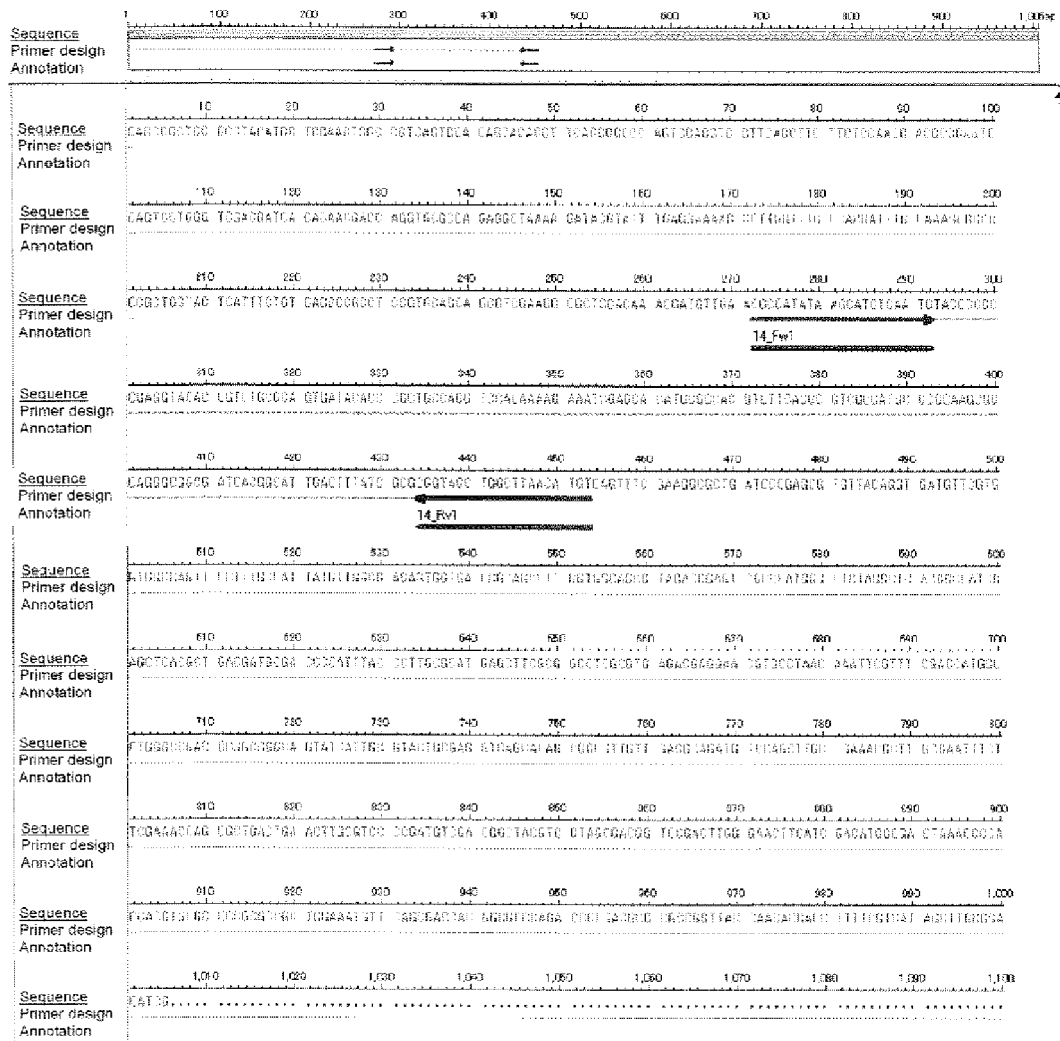

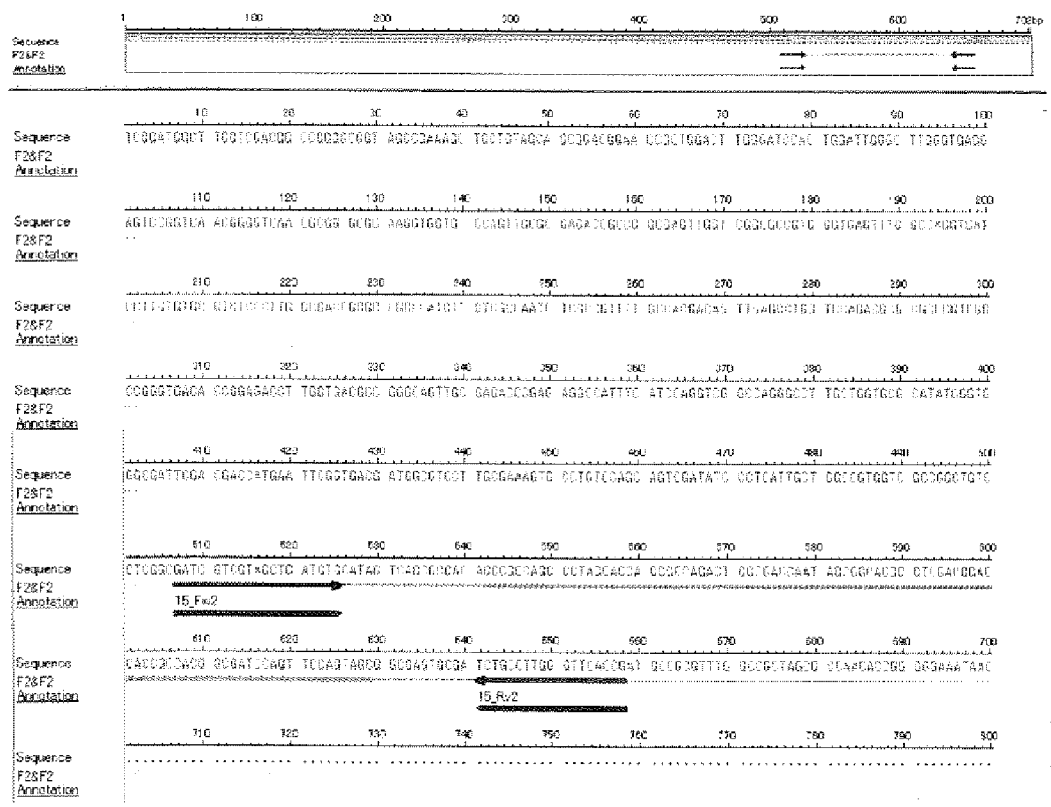
[Fig.8]

[Fig.9]
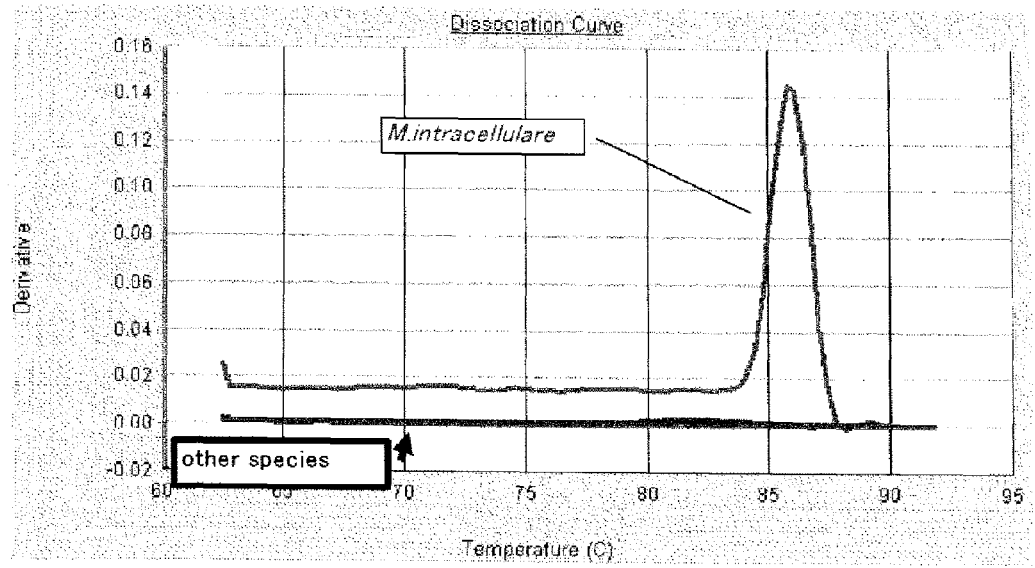
[Fig.10]
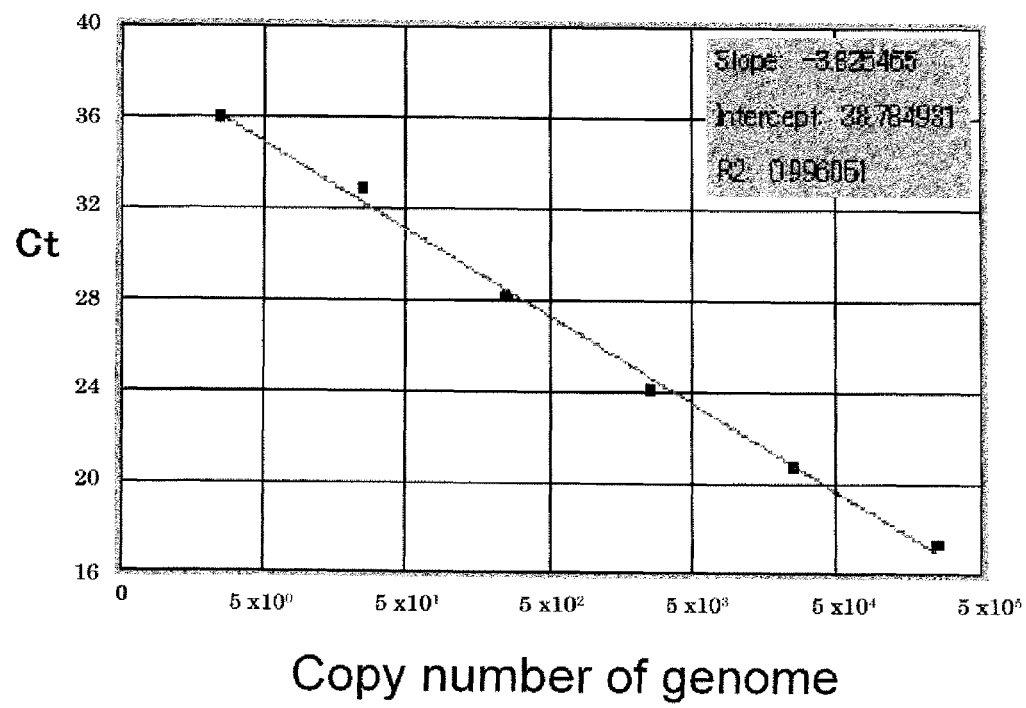
Copy number of genome

PRIMER AND PROBE FOR DETECTION OF MYCOBACTERIUM INTRACELLULARE

TECHNICAL FIELD

The present invention relates to a method for detecting and/or identifying *Mycobacterium intracellulare* (hereinafter optionally abbreviated as *M. intracellulare*) through the use of amplification of nucleic acid and detection system thereof.

BACKGROUND ART

Nontuberculous *mycobacterium* is a gram positive *bacillus* having acid-fast characteristics classified into genus *Mycobacterium* (hereinafter, optionally abbreviated simply as M.), and is a kind of acid-fast bacterium other than tuberculosis complex and *Mycobacterium leprae*. Fifteen to 20% of cases showing positive for sputum smear examination for acid-fast bacterium have been diagnosed thereafter to be nontuberculous *mycobacterium* by the test for the identification of bacterial species.

Among nontuberculous *mycobacterium*, clinically problematic bacterial species are blown to be *M. intracellulare, Mycobacterium kansasii, Mycobacterium marinum, Mycobacterium gordonae, Mycobacterium szulgai, Mycobacterium avium, Mycobacterium xenopi, Mycobacterium fortuitum, Mycobacterium chelonei, Mycobacterium abscessus*, and so on.

Above all, the commonly noted strains are *M. intracellulare* and *M. avium*. Since *M. intracellulare* and *M. avium* are closely resemble each other and difficult to distinguish between them, *M. intracellulare* and *M. avium* have been referred to collectively as *Mycobacterium avium* complex (MAC). About 70% of patients with nontuberculous mycobacteria disease are MAC infection, and the second large population is *M. kansasii* infection accounting 20%. And the rest of 10% are the infection by other bacterial species.

In general, since the nontuberculous mycobacteria have weak toxicity, they are believed to be harmless to a healthy subject. However, on rare occasions, they may exert infectivity to human. Among them, the MAC is known to cause sometimes aftereffects of tuberculosis (lung infectious disease), or to cause opportunistic infections to a compromised patient such as AIDS patient. Therefore, it is particularly important in the therapy to detect the nontuberculous mycobacteria with rapidity and preciseness.

In addition, in recent years, the incidence of nontuberculous *mycobacterium* infection demonstrates upward trend, and therefore, development of a method for discriminating tuberculosis bacterium from nontuberculous *mycobacterium* in a short period of time has been desired strongly. Moreover, from the viewpoint of the fact that the method of detecting/diagnosing *M. intracellulare* and *M. avium* by nucleic acid amplification technology has been included in health insurance coverage, its diagnostic significance is obviously great.

In addition, most of the nontuberculous mycobacteria demonstrate resistance against antituberucular agents. Therefore, when a patient is suspected of acid-fast bacterium infection, differential diagnosis whether the disease is tuberculosis or nontuberculous *mycobacterium* disease is quite important to decide a course of treatment. Further, as a method for treatment of the diseases caused by nontuberculous mycobacteria may vary depending on the individual species of bacterium, the identification of bacterial species is also quite important. However, nontuberculous *mycobacterium* diseases do not show any specific clinical symptom. Therefore, it is quite difficult to differentiate tuberculosis from nontuberculous *mycobacterium* disease by clinical observation and histopathological manifestation, and to specify the species of the nontuberculous *mycobacterium*. Consequently, the diagnosis whether the disease is tuberculosis or nontuberculous *mycobacterium* disease has to be carried out by identification of the infected bacterium.

A typical method for the identification of bacterium to be carried out for the diagnosis of nontuberculous mycobacterium disease is sputum smear examination. However, by this test, it can be recognized only whether the pathogenic bacterium is "acid-fast bacterium-positive" or not, and cannot be identified whether the pathogenic bacterium is tuberculosis bacteria or nontuberculous *mycobacterium*. Therefore, when result of the sputum smear examination is positive, bacterial culture examination by isolation culture on a culture medium such as Ogawa's medium is carried out to differentiate between tuberculosis bacteria and nontuberculous *mycobacterium*. And further, by performing additional biochemical examinations, bacterial species of the infected bacterium is identified. However, in general, growth of genus *Mycobacterium* is slow; for example, it takes 3 to 4 weeks only for its isolation culture. And further, it requires additional 2 to 3 weeks to obtain results of various biochemical tests for the identification of bacterial species. Accordingly, the conventional basic method, in which a diagnostic outcome on whether the disease is tuberculosis or not is obtained by conducting the above described smear examination and a cell culture assay, is a considerably time-consuming method.

On the other hand, in recent years, a technology of detecting bacteria on a genetic level has been developed. For example, a diagnostic technique utilizing the nucleic acid amplification technology such as polymerase chain reaction (PCR) and the like has been studied as a useful means for detecting bacteria. Because of high sensitivity of this method, even if there are only several cells of the bacteria in a sample, the bacteria can be detected. In addition, this method has an advantage that the detection (identification of bacterial species) can be completed in a short time (in 4 days at the longest). However, in the usual PCR method, the number of bacteria cannot be determined. In addition, in this method, cells are detected regardless of live cells or dead cells. Further, if some bacteria exist in the sample, the determination is made positive regardless of size of the bacterial count. Therefore, by the PCR method, diagnosis of infectivity will be provided with uncertainty. Furthermore, the method has other problems such as that judgment of false positive tends to be made due to too high sensitivity.

With respect to the method for detection of *M. intracellulare* using the PCR method, there is a method for detection of existence or absence of MAC nucleic acid using a multiple primer set of oligonucleotide primer specific for 2 or more of gene regions comprising, for example, MacSequevar gene region, 19 kD protein (MAV 19k) gene region of *M. avium*, and ribosomal protein s1 gene region of *M. intracellulare* (Patent Literature 1). However, by this method, discrimination between *M. intracellulare* and *M. avium* cannot be achieved. In addition, in the PCR using the employed rps1 primer (a primer designed from the ribosomal protein s1 gene region of *M. intracellulare*), even when the isolated strain of *M. avium* is used as a sample, the amplification product has also been detected; there remains a problem in terms of the specificity for *M. intracellulare*.

In addition, a method has also been known, in which PCR is performed by using a primer which is capable of amplifying a DNA nucleotide sequence targeting insertion site of the gene insertion sequence IS901, and determining whether it is avian tuberculosis bacterium (*M. avium*) or *M. intracellulare* based on a chain length of the obtained amplification product (Patent Literature 2). However, in the PCR using the aforementioned primer, the primer extension product can be obtained not only when the sample is avian tuberculosis bacterium (*M. avium*) but also *M. intracellulare*, and therefore, this determination method can not be said as a specific method for *M. intracellulare*. In addition, the method, whereby the discrimination between both bacterial species is carried out based on the chain length of the primer extension product, is cumbersome; and it is conceivable that different determination may be made depending on the judge; and in consequence, the method cannot be said as a reliable determination method.

Other than the PCR method, there is a determination method through the use of Strand Displacement Amplification Method (SDA method). For example, JP-A-1998-4984 (Patent Literature 3) discloses a method in which the 63 nucleotide segment of BCG85-B gene coding a part of α-antigen of mycobacteria is targeted. In this method, using a primer which is capable of amplifying the target sequence in the BCG85-B gene owned by both *M. intracellulare* and *M. avium*, nucleic acid amplification reaction is performed by the SDA method, and then MAC is detected based on the results. That is, the primer used in the aforementioned method is a primer capable of amplifying both *M. intracellulare* and *M. avium*. However, in this method, as a matter of course, a primer extension product will be obtained in both cases where either of *M. intracellulare* or *M. avium* exists in a sample. Because of this, MAC can be detected by this method; however, it is impossible to detect *M. intracellulare* specifically. In addition, even when MAC is detected, there can be an instance where false-positive result is provided.

In JP-A-2001-103986 (Patent Literature 4), a primer to be used for the detection of MAC and an oligonucleotide to be used as a capture probe and a detection probe have been disclosed. However, the aforementioned primer can amplify a 48 bp target sequence from dnaJ gene which is owned commonly by both *M. intracellulare* and avian tuberculosis bacteria (*M. avium*). Namely, amplification reaction will take place in both cases where either of *M. intracellulare* or *M. avium* is present in a sample. Therefore, if the SDA method is practiced using aforementioned primer, the primer extension product will be detected using the capture probe and detection probe, and based on the results, detection of MAC can be achieved. However, specific detection of *M. intracellulare* is impossible to achieve without detection of *M. avium*.

Beyond that, there is a method of amplification of nucleic acid of *M. intracellulare* through the use of LAMP (Loop-Mediated Isothermal Amplification) method, and the like. However, in the LAMP method, there remains some problems such as that the nucleotide sequence of amplified DNA cannot be determined; that efficient length of DNA to be amplified is limited; and that the method provides false-positive result occasionally; and the like.

As described above, in this situation, it has been desired to establish a method which enables to detect *M. intracellulare* specifically and rapidly.

Patent Literature 1 JP-A-1999-69999;
Patent Literature 2 JP-3111213;
Patent Literature 3 JP-A-1998-4984;
Patent Literature 4 JP-A-2001-103986;
Patent Literature 5 JP-A-2005-204582;
Non-Patent Literature 1: F. Poly et al., J. Bacteriology, 2004, 186 (14), p. 4781-4795.

DISCLOSURE OF THE INVENTION

Problems to be Solved by the Invention

The present invention was made in view of the above described situation, and an object of the present invention is to provide a new primer for detecting *M. intracellulare* which can exclude any false-positive result for the diagnosis; and to provide a method for detecting *M. intracellulare* more simply, rapidly and with high accuracy.

Means for Solving Problems

The present invention was made for the purpose of solving the above described problems, and comprises the following aspects:
(1) An oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 (wherein A represents adenine, C represents cytosine, G represents guanine and T represents thymine, respectively; and, T at arbitrary position may be replaced by uracil (U); and hereinafter, the same abbreviations will be used), or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8,
wherein the oligonucleotide is capable of hybridizing with a nucleotide sequence of *Mycobacterium intracellulare* gene.
(2) A primer for detecting *Mycobacterium intracellulare* comprising, an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8,
wherein the oligonucleotide is capable of hybridizing with a nucleotide sequence of *Mycobacterium intracellulare* gene.
(3) A probe for detecting *Mycobacterium intracellulare* comprising, an oligonucleotide comprising a part or the entire sequence of the nucleotide sequence shown in SEQ ID NO: 1, SEQ ID NO; 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8,
wherein the oligonucleotide is capable of hybridizing with a nucleotide sequence of *Mycobacterium intracellulare* gene.
(4) A method for detecting *Mycobacterium intracellulare*, comprising using an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene as a primer and/or a probe.

(5) A reagent kit for detecting *Mycobacterium intracellulare*, comprising an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene as a primer and/or a probe.

The present inventor conducted theoretical and experimental verification of genetic homology between species with regard to the nucleotide sequence of various species including *M. intracellulare* and other living organisms. As a result, the present inventor has found that a nucleotide sequence is present in the nucleic acid fragments derived from *M. intracellulare* obtained by the method using microarray technique, which is capable of hybridizing specifically with a particular region of the nucleotide sequence for a *M. intracellulare* and useful for detection of *M. intracellulare*.

And so, on the basis of these findings, the present inventor further studied intensively and obtained an oligonucleotides specific for *M. intracellulare* (the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8), and has found that these nucleotide sequences are useful for detection of *M. intracellulare*. And further, on the basis of these sequences, a primer and a probe for the detection of *M. intracellulare* have been developed, and thus a method for detection of *M. intracellulare* using these primer and probe has been established.

EFFECT OF THE INVENTION

According to the method for detection of *M. intracellulare* using the primer and/or probe of the present invention, *M. intracellulare* can be detected and diagnosed more rapidly and with high accuracy compared to the conventional bacterium identification method by a cell culture assay and the like. In addition, by performing the detection using the method of the present invention, any false-positive result in diagnosis can be eliminated as compared with the diagnosis method by PCR using a conventional primer and/or a probe, and as the results, *M. intracellulare* can be detected and diagnosed with higher accuracy and preciseness in a specific manner. Further, by the use of the detection method of the present invention, *M. intracellulare* cell can also be quantified.

BRIEF DESCRIPTION OF THE DRAWINGS

FIG. 1 shows the nucleotide sequence of candidate clone 1 (SEQ ID NO:1, 666 nucleotides), and the location and size of primers 02_Fw1 (SEQ ID NO:9) and 02_Rv1 (SEQ ID NO:10) within the sequence of the candidate clone 1 are designated by the heavy arrows.

FIG. 2 shows the nucleotide sequence of candidate clone 2 (SEQ ID NO:2, 1128 nucleotides), and the location and size of primers 03_Fw1 (SEQ ID NO:23) and 03_Rv1 (SEQ ID NO:4) within the sequence of the candidate clone 2 are designated by the heavy arrows.

FIG. 3 shows the nucleotide sequence of candidate clone 3 (SEQ ID NO:3, 1002 nucleotides), and the location and size of primers 04_Fw2 (SEQ ID NO:41) and 04_Rv2 (SEQ ID NO:42) within the sequence of the candidate clone 3 are designated by the heavy arrows.

FIG. 4 shows the nucleotide sequence of candidate clone 4 (SEQ ID NO:4, 747 nucleotides), and the location and size of primers 06_Fw1 (SEQ ID NO:59) and 06_Rv1 (SEQ ID NO:60) within the sequence of the candidate clone 4 are designated by the heavy arrows.

FIG. 5 shows the nucleotide sequence of candidate clone 5 (SEQ ID NO:5, 618 nucleotides), and the location and size of primers 10_Fw1 (SEQ ID NO:79) and 10_Rv1 (SEQ ID NO:80) within the sequence of the candidate clone 5 are designated by the heavy arrows.

FIG. 6 shows the nucleotide sequence of candidate clone 6 (SEQ ID NO:6, 510 nucleotides), and the location and size of primers 13_Fw2 (SEQ ID NO:93) and 13_Rv2 (SEQ ID NO:94) within the sequence of the candidate clone 6 are designated by the heavy arrows.

FIG. 7 shows the nucleotide sequence of candidate clone 7 (SEQ ID NO:7, 1005 nucleotides), and the location and size of primers 14_Fw1 (SEQ ID NO:105) and 14_Rv1 (SEQ ID NO:106) within the sequence of the candidate clone 7 are designated by the heavy arrows.

FIG. 8 shows the nucleotide sequence of candidate clone 8 (SEQ ID NO:8, 700 nucleotides), and the location and size of primers 15_Fw2 (SEQ ID NO:127) and 15_Rv2 (SEQ ID NO:128) within the sequence of the candidate clone 8 are designated by the heavy arrows.

FIG. 9 shows results of an analysis of melting curve obtained based on the results of the real-time PCR by the intercalator method using Primer 02_Fw1 and Primer 02_Rv1 and using a DNA sample derived from *M. intracellulare* as a template obtained in Example 1.

FIG. 10 shows results of detection performed by the real-time PCR in Example 2, which is a standard curve drawn by plotting Ct value (Y-axis) for the copy number of genome (X-axis, logarithmic scale) of each DNA sample for PCR.

BEST MODE FOR CARRYING OUT THE INVENTION

In the present invention, *M. intracellulare* gene refers to an arbitral unit of nucleotide sequence (a region) in the entire genome sequence owned by *Mycobacterium intracellulare*. The entire genome sequence of *Mycobacterium intracellulare* has not been completed yet.

The oligonucleotide of the present invention includes an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 (wherein A represents adenine, C represents cytosine, G represents guanine and T represents thymine, respectively; and, T at arbitrary position may be replaced by uracil (U); and hereinafter, the same abbreviations will be used), or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene (hereinafter, optionally referred to as "the oligonucleotide of the present invention").

As to size of the oligonucleotide of the present invention, an oligonucleotide having the nucleotide sequence shown in SEQ ID NO: 1 has 666 nucleotides; an oligonucleotide having the nucleotide sequence shown in SEQ ID NO: 2 has 1128 nucleotides; an oligonucleotide having the nucleotide sequence shown in SEQ ID NO: 3 has 1002 nucleotides; an oligonucleotide having the nucleotide sequence shown in SEQ ID NO: 4 has 747 nucleotides; an oligonucleotide having the nucleotide sequence shown in SEQ ID NO: 5 has 618 nucleotides; an oligonucleotide having the nucleotide sequence shown in SEQ ID NO: 6 has 510 nucleotides; an oligonucleotide having the nucleotide sequence shown in SEQ ID NO: 7 has 1005 nucleotides; and an oligonucleotide having the nucleotide sequence shown in SEQ ID NO: 8 has 700 nucleotides.

An oligonucleotide of the present invention which comprises a part or the entire sequence of the nucleotide sequence shown in SEQ ID NO: 1, SEQ ID NO; 2, SEQ ID NO: 3, SEQ ID NO; 4, SEQ ID NO: 5, SEQ ID NO; 6, SEQ ID NO: 7 or SEQ ID NO: 8 includes, for example, (1) an oligonucleotide comprising a nucleotide sequence having a sequence homology of not less than 70%, preferably not less than 80%, more preferably not less than 90%, further more preferably not less than 95% to the nucleotide sequence of SEQ ID NO: 1, SEQ ID NO: 2, SEQ ID NO: 3, SEQ ID NO: 4, SEQ IDE NO: 5, SEQ ID NO: 6, SEQ ID NO: 7 or SEQ ID NO: 8, or (2) an oligonucleotide comprising more than 10 consecutive nucleotides, preferably more than 15 consecutive nucleotides, more preferably more than 20 consecutive nucleotides in the sequence shown in SEQ ID NO; 1, SEQ ID NO: 2, SEQ ID NO: 3, SEQ ID NO; 4, SEQ ID NO: 5, SEQ ID NO: 6, SEQ ID NO: 7 or SEQ ID NO: 8, or the like.

Specific examples of the oligonucleotide of the present invention which comprises the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 includes, for example, the oligonucleotide which consists of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or the oligonucleotide which comprises the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8.

A specific example of the oligonucleotide which comprises a part of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 includes, for example, the one which comprises a part or the entire sequence of the sequence selected from the nucleotide sequences shown in SEQ ID NO: 9 to 203. Preferably, an oligonucleotide which comprises more than 10 consecutive nucleotides, preferably more than 15 consecutive nucleotides, more preferably more than 20 consecutive nucleotides in the sequence selected from the nucleotide sequences shown in SEQ ID NO: 9 to 203, is included.

A specific example of the oligonucleotide which comprises the entire sequence of a sequence selected from the nucleotide sequences shown in SEQ ID NO: 9 to 203 includes an oligonucleotide consisting of a sequence selected from the nucleotide sequences shown in SEQ ID NO: 9 to 203, or an oligonucleotide which comprises a sequence selected from the nucleotide sequences shown in SEQ ID NO: 9 to 203.

A specific example of an oligonucleotide which comprises a part of the nucleotide sequence shown in SEQ ID NO: 1 includes, for example, the one which comprises a sequence selected from the nucleotide sequences shown in SEQ ID NO: 9 to 22 or SEQ ID NO: 139 to 145.

A specific example of an oligonucleotide which comprises a part of the nucleotide sequence shown in SEQ ID NO: 2 includes, for example, the one which comprises a sequence selected from the nucleotide sequences shown in SEQ ID NO: 23 to 40 or SEQ ID NO: 146 to 154.

A specific example of an oligonucleotide which comprises a part of the nucleotide sequence shown in SEQ ID NO: 3 includes, for example, the one which comprises a sequence selected from the nucleotide sequences shown in SEQ ID NO: 41 to 58 or SEQ ID NO: 155 to 163.

A specific example of an oligonucleotide which comprises a part of the nucleotide sequence shown in SEQ ID NO: 4 includes, for example, the one which comprises a sequence selected from the nucleotide sequences shown in SEQ ID NO: 59 to 78 or SEQ ID NO: 164 to 173.

A specific example of an oligonucleotide which comprises a part of the nucleotide sequence shown in SEQ ID NO: 5 includes, for example, the one which comprises a sequence selected from the nucleotide sequences shown in SEQ ID NO: 79 to 92 or SEQ ID NO: 174 to 180.

A specific example of an oligonucleotide which comprises a part of the nucleotide sequence shown in SEQ ID NO: 6 includes, for example, the one which comprises a sequence selected from the nucleotide sequences shown in SEQ ID NO: 93 to 104 or SEQ ID NO: 181 to 186.

A specific example of an oligonucleotide which comprises a part of the nucleotide sequence shown in SEQ ID NO: 7 includes, for example, the one which comprises a sequence selected from the nucleotide sequences shown in SEQ ID NO: 105 to 126 or SEQ ID NO: 187 to 197.

A specific example of an oligonucleotide which comprises a part of the nucleotide sequence shown in SEQ ID NO: 8 includes, for example, the one which comprises a sequence selected from the nucleotide sequences shown in SEQ ID NO: 127 to 138 or SEQ ID NO: 198 to 203.

An oligonucleotide of the present invention which comprises a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 includes, for example, an oligonucleotide comprising a part or the entire sequence of the nucleotide sequence which is capable of hybridizing with the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 of the present invention, and the like.

The above described oligonucleotide which comprises a part or the entire sequence of the nucleotide sequence which is capable of hybridizing with the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 of the present invention includes, in particular, an oligonucleotide having a part or the entire sequence of the nucleotide sequence which is capable of hybridizing under high stringent condition or stringent condition with the oligonucleotide shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 of the present invention, and the like.

It should be noted that, the phrase of "high stringent condition" used herein means, specifically, for example, "the condition where hybridization is carried out in 50% formamide at 42 to 70° C., preferably 60 to 70° C., and followed by washing with 0.2 to 2×SSC containing 0.1% sodium dodecyl sulfate (SDS) at 25 to 70° C.".

In addition, the phrase of "stringent condition" means, specifically, for example, "the condition where hybridization is carried out in 6×SSC or a hybridization solution with equivalent salt concentration at the temperature of 50 to 70° C. for 16 hours, and then, if needed, pre-washing with 6×SSC or a solution with the equivalent salt concentration, and followed by washing with 1×SSC or a solution with the equivalent salt concentration and the like".

An example of the oligonucleotide which comprises a part or the entire sequence of the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 of the present invention includes, for example, (1) an oligonucleotide comprising a nucleotide sequence having a sequence homology of not less than 70%, preferably not less than 80%, more preferably not less than 90%, further more preferably not less than 95% to the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6. SEQ ID NO; 7 or SEQ ID NO: 8, or (2) an oligonucleotide comprising more than 10 consecutive nucleotides, preferably more than 15 nucleotides, more preferably more than 20 nucleotides in the sequence complementary to the nucleotide sequence shown in SEQ ID NO; 1, SEQ ID NO: 2, SEQ ID NO: 3, SEQ ID NO: 4, SEQ ID NO: 5, SEQ ID NO: 6. SEQ ID NO: 7 or SEQ ID NO; 8, and the like.

A specific example of the oligonucleotide which comprises the entire sequence of the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 of the present invention includes, for example, an oligonucleotide consisting of the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or an oligonucleotide which comprises the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8.

A specific example of the oligonucleotide which comprises a part of the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO; 7 or SEQ ID NO: 8 includes, for example, an oligonucleotide comprising a part or the entire sequence of the sequence complementary to the nucleotide sequence selected from the nucleotide sequences shown in SEQ ID NO: 9 to 203. Preferably, an oligonucleotide which comprises more than 10 consecutive nucleotides, preferably more than 15 nucleotides, more preferably more than 20 nucleotides in the sequence complementary to the nucleotide sequence selected from the nucleotide sequences shown in SEQ ID NO: 9 to 203, is included.

A specific example of the oligonucleotide which comprises the entire sequence TO of the sequence complementary to the nucleotide sequence selected from the nucleotide sequences shown in SEQ ID NO: 9 to SEQ ID NO: 203 includes, for example, an oligonucleotide consisting of a sequence complementary to the nucleotide sequence selected from the nucleotide sequences shown in SEQ ID NO: 9 to 203, or an oligonucleotide which comprises a sequence complementary to the nucleotide sequence selected from the nucleotide sequences shown in SEQ ID NO: 9 to 203.

The oligonucleotide being capable of hybridizing with a nucleotide sequence of *M. intracellulare* gene of the present invention includes an oligonucleotide which comprises a nucleotide sequence being capable of hybridizing with the nucleotide sequence of *M. intracellulare* gene under the above described high stringent condition or the stringent condition, and the like. The high stringent condition and the stringent condition are as described above.

It should be noted that, the oligonucleotide of the present invention may be either deoxyribonucleic acid (DNA) or ribonucleic acid (RNA). In the case of ribonucleic acid, it goes without saying that thymidine residue (T) may be read as uridine (U) residue. In addition, it may be a DNA comprising uridine residue which is synthesized by exchanging T at arbitral position by U. Also, it may be an RNA comprising thymidine residue which is synthesized by exchanging U at arbitral position by T. In addition, there may be deletion, insertion or replacement of one or plural nucleotides. One or plural nucleotides may be a modified nucleotide such as inosine (I).

Method for obtaining the oligonucleotide of the present invention includes, for example, but not limited to, a method for preparing by chemical synthesis well known per se. In this method, it is possible to obtain an oligonucleotide of the same quality without difficulty in larger scale at lower cost compared to the method of obtaining the oligonucleotide or the polynucleotide by genetic engineering technique using a vector and the like (cloning method).

For example, by a conventional method of DNA synthesis using a DNA synthesizer, an oligonucleotide is synthesized according to the conventional phosphoramidite method, and purified by a conventional method of the anion exchange column chromatography. And thus, an objective oligonucleotide of the present invention can be obtained.

Alternatively, using vendor's custom service of contract synthesis, the oligonucleotide may be purchased from the vendor.

A means for searching (screening) an oligonucleotide which can attain the purpose of the present invention include the subtraction method as described in FEMS Microbiology Letters 166: 63-70, 1998 or Systematic and Applied Microbiology 24: 109-112, 2001, which is a methodology of concentrating a candidate sequence by subtracting a nucleotide sequence which reacts with a fragment of genomic DNA derived from a species to be differentiated from a group of fragments derived from the target genomic DNA.

In addition, an approach in which differential display of amplification products from a target genomic DNA and a genomic DNA derived from species to be differentiated are prepared, that is, a methodology utilizing the arbitrarily primed polymerase chain reaction (AP-PCR) (JP-A-1999-155589) and the like can be considered.

Further, also by use of so called microarray method, searching of an oligonucleotide which can attain the purpose of the present invention can also be performed, and the oligonucleotide of the present invention can be obtained. The brief description of the method is as follows:

Namely, for example, a shotgun clone of genomic DNA derived from *M. intracellulare* is prepared, and then the DNA is purified from the obtained shotgun clone. After that, the purified DNA derived from the shotgun clone is amplified by PCR and the like, and the amplified DNA is arranged on a slide glass to prepare a microarray. In addition, a group of fluorescent labeled genomic DNA fragments (Label-1) is prepared from the genomic DNA of target *M. intracellulare*. On the other hand, a group of fluorescent labeled DNA fragments (Label-2) is prepared separately from the genomic DNA derived from species to be differentiated, and used for the comparative experiment. That is, the reactivity (binding potency) of each Label-1 and Label-2 to the sequence on the microarray is assayed by a competitive hybridization method using the Label-1 and Label-2 in the same reaction system. By this assay, the candidate sequence group which react more specifically to the fragments (Label-1) derived from genomic DNA of the target *M. intracellulare* can be selected (for example, Non-Patent Literature 1, and the like), and thereby, the objective oligonucleotide can be selected. An example of the method for selection of the oligonucleotide of the present invention using the microarray method will be described in detail as follows;

(1) Preparation of Purified Genomic DNA Derived from *M. intracellulare*

At first, the microbial cell of *M. intracellulare* strain is subjected to conventional disrupting treatment (for example, the pulverizing treatment of microbial cell by autoclaving and using glass beads and the like), and then extraction and purification of DNA may be carried out according to the conventional procedures.

(2) Preparation of Whole Genome Shotgun Library

As an example of the method for preparing Whole Genome Shotgun library of *M. intracellulare*, a method modified from the Whole Genome Shotgun method described in Venter et al., Science 2001 Feb. 16; 291 (5507): 1304-1351 will be described below.

First, the purified genomic DNA derived from *M. intracellulare* obtained in the above described (1) is diluted with an appropriate buffer solution and the like, and then subjected to DNA fragmentation treatment, for example, in the presence of 20% final concentration of glycerol, by treating for about 1 to 5 minutes using a nebulizer under a pressure of 5 to 9 kPa. By this treatment method, the objective size of 500 to 1,000 base pair fraction can be recovered efficiently. The fraction obtained is purified using a commercially available extraction column.

After that, the recombinant DNA (Whole Genome Shotgun library of *M. intracellulare*) in which the obtained fraction (DNA fragments, containing the objective DNA fragments) is inserted into a vector DNA by ligation according to the common methods, is obtained.

The vector to be used for this purpose includes, in the case where the host cell for subsequent transformation is *E. coli*, for example, the vectors such as pBS (e.g., pBSII sk$^+$ vector (Stratagene Corp.)), pQE-TRI plasmid (Qiagen Inc.), pBluescript, pET, pGEM-3Z, pGEX and the like. Depending on kind of the vector to be used, prior to the ligation, terminal of the DNA fragments may be blunted by treating with DNA polymerase and the like in advance.

After that, using the obtained recombinant DNA, an appropriate host cell is transformed to obtain a transformant.

The host cell to be used for this purpose includes, for example, *E. coli*, preferably the strain of JM109, DH5α, TOP10 and the like. In addition to these, competent cells having higher transfection efficiency for the plasmid and the phage DNA may be used. For example, *E. coli* JM109 Competent Cells (Takara Bio Inc.) and the like are included.

The transformation may be carried out according, for example, to the D. M. Morrison's method (Method in Enzymology, 68, 326-331, 1979) and the like. In addition, when a commercially available competent cell is used, the transformation may be carried out according to the protocol provided for the product.

Selection of the transformant which is transformed with the recombinant DNA having objective DNA fragment may be carried out, for example, by a method utilizing the property of the vector used for the transformation. For example, when a vector comprising ampicillin-resistant gene is used, by culturing the transformant on a medium containing ampicillin and selecting the resulting clone, the transformant which has been transformed by the recombinant DNA incorporating the objective DNA fragment (Whole Genome Shotgun library derived from *M. intracellulare* genome) can be obtained easily.

(3) Preparation of Microarray

Microarray is prepared by the following method.

Namely, from the transformant (Whole Genome Shotgun clone library derived from *M. intracellulare* genome) obtained in the above described (2), DNA is purified according to the conventional methods. Using the purified DNA as a template, and using a suitable primer (it may be a commercially available primer; for example, M13 Primer M1 (Takara Bio Inc.) and M13 Primer RV (Takara Bio Inc.) and the like), the PCR is performed according to the conventional procedure and the obtained PCR amplification product is purified. After that, according to the conventional procedures, the purified PCR amplification product is spotted on a slide glass for microarray. The spots are irradiated with UV light (60 mJ/cm$^2$ to 300 mJ/cm$^2$, normally 150 mJ/cm$^2$) to fix the PCR amplification product (comprising target DNA derived from *M. intracellulare*) on the slide glass, and thus the microarray is prepared.

It should be noted that a control microarray is also prepared, if necessary. For example, using a DNA fragment having a specific sequence for *M. intracellulare* such as rps 1 (Patent Literature 1) and a DNA fragment of genomic DNA derived from species to be differentiated [partial sequence of insertion sequence IS6110 unique to tuberculosis bacteria (IS6110 element), a DNA fragment having nucleotide sequence specific for *M. kansasii* such as KATS2 sequence (JP-A-1999-155589), a DNA fragment having nucleotide sequence specific for *M. avium* such as MAV 19K (Patent Literature 1), and the like, and for example, the DNA derived from bacteria other than *Mycobacterium* genus such as *E. coli*, and the like], a line of treatment from the fragmentation of each DNA to the preparation of Whole Genome Shotgun clone library is carried out in the same way; the PCR is performed in the same way; the PCR products obtained are fixed on a slide glass; and the microarray for each DNA is prepared.

It should be noted that, with respect to the microarray for control, when a certain microarray is set as a positive control, as a Cy3-labeled genomic DNA for comparison which will be used in microarray hybridization later, a genomic DNA which is derived from the same bacterial cell as that originated from aforementioned positive control and labeled with Cy3 is used. For example, when a microarray is prepared using a DNA fragment having a nucleotide sequence specific for *M. kansasii* and configured as a positive control, a labeled product, which is a genomic DNA extracted and purified from *M. kansasii* and then labeled with Cy3, is used as one of the Cy3-labeled comparative genomic DNA to be used in the microarray hybridization.

In addition, when a certain microarray is set as a negative control, in a microarray hybridization performed later, neither Cy3-labeled product nor Cy5-labeled product of the genomic DNA derived from the same microbial cell to that from aforementioned negative control is used.

(4) Labeling of Target Genomic DNA with Fluorescent Dye i) Labeling of Target Genomic DNA with Fluorescent Dye The genomic DNA which is extracted and purified from *M. intracellulare* strain by the conventional method is labeled with Cy5 by an indirect labeling method using hexylamino-UTP. Also, the comparative genomic DNA which is extracted and purified from the microbial cell from the above described positive control in microarray is labeled with Cy3. For example, an indirect labeling method which has been modified from a protocol published by DeRisi Laboratory (www.microarray.org) will be explained as an example. In this method, using αUTP having an amino group, an αUTP-incorporated DNA chain is produced by incorporating it into the molecule by enzymatic extension reaction. And, to this amino group, a fluorescent dye (succinimide body) is coupled chemically, thereby, the DNA is labeled.

First, the starting materials (genomic DNA derived from *M. intracellulare* and comparative genomic DNA) are subjected to heat denaturation treatment according to the conventional method. After that, to the heat treated material, 2 µl DTT, a mixed solution of dATP/dCTP/dGTP, dTTP, Ha-dUTP and Klenow enzyme, are added, and the extension reaction is performed at 37° C. for about 3 hours. The obtained reaction product is placed onto an ultrafiltration column and centrifuged at 14,000 rpm for about 4 minutes, and the concentrated solution is recovered in a microtube, and then dried thoroughly using a centrifugal vacuum drier and the like. After that, to the dried above reaction product, $NaHCO_3$ is added and mixed, and then left for standing at ambient temperature for 2 to 3 minutes.

Separately, a solution of Cy3 (or Cy5) dissolved in DMSO (Cy-dye Solution Cy3, Cy-dye Solution Cy5) is prepared. This Cy-dye Solution Cy3 is added to the above described reaction product obtained by the use of comparative genomic DNA, and the Cy-dye Solution Cy5 is added to the above described reaction product obtained by the use of genomic DNA from *M. intracellulare*, and each mixture is incubated under light shielding at 40° C. for about 60 minutes. Further, each reaction product is added with 4 M $NR_2OH$ and mixed, and incubated under light shielding for about 15 minutes to obtain the labeled product of each genomic DNA. After that, the obtained labeled product is placed onto an ultrafiltration column and centrifuged at 14,000 rpm for about 4 minutes, The concentrated solution is recovered in a microtube, and then dried thoroughly using a centrifugal vacuum drier.

ii) Fragmentation Process of The Labeled Products

For each of the labeled products of the DNA fragments derived from each genome in dry state obtained in the above i) of (4), a solution of the following components and final concentrations of 0.04 M Tris-acetate (pH 8.1), 0.1 M potassium acetate, and 0.03 M magnesium acetate tetrahydrate is prepared. To the aforementioned solution, the labeled product of DNA fragments derived from genome in dry state is mixed in suspension. The suspension is heat-treated at 94° C. for 15 minutes, and the labeled product of DNA fragments derived from genome with 100 base to 300 base is obtained (Cy3-labeled product, Cy5-labeled product).

The Cy3-labeled product and the Cy5-labeled product obtained are mixed; the mixture is placed onto an ultrafiltration column and centrifuged at 14,000 rpm for about 4 minutes; the concentrated solution is recovered in a microtube; and then dried thoroughly using a centrifugal vacuum drier.

After that, to this microtube, a reagent solution which contains 0.5 µl of salmon sperm DNA (10 mg/ml) and 5 µl of formamide having a total volume adjusted to give 40 to 50 µl using ArrayHyb Hybridization buffer (SIGMA-Aldrich Co.) (this composition is for the case where a size of cover glass to be used for the microarray later is 24×55 mm) is added, and the dry material obtained above is mixed in suspension in the same solution, and then incubated at 95° C. for about 5 minutes to prepare a mixed solution of the Cy3- and Cy5-labeled products.

(5) Microarray Hybridization (DNA-DNA Hybridization on the Array)

On a microarray (DNA chip) prepared in the above described (3), a mixed solution of the Cy3- and Cy5-labeled products prepared in the above described ii) of (4) is placed, and covered with a cover glass. The microarray is set on a Hybri-cassette, and kept at 65° C. under light shielding for not less than 8 hours to allow hybridization. After hybridization, the microarray is dipped in a 2×SSC-0.1% SDS solution together with the cover glass at room temperature, and the cover glass is removed. After sequential washing with 1×SSC solution containing 0.03% SDS (60° C.) for 10 minutes, 0.2×SSC solution (42° C.) for 10 minutes and 0.05×SSC solution (room temperature) for 10 minutes, the microarray is dried by centrifugation at 800 rpm for 5 minutes.

(6) Measurement of Fluorescence Intensity: from Signal Detection to Quantification Using a fluorescence detection scanner, the fluorescence intensity of the microarray on which the microarray hybridization has been carried out as described in the above (5) is measured. On this occasion, the fluorescence intensity is measured by 2 channels of Cy3 and Cy5 to obtain detection data of fluorescence. Quantification of the fluorescence signal may be performed using commercially available DNA chip expression image analysis software and the like, and carrying out automated spot recognition, background calculation, and normalization of the fluorescence intensity ratio according to the operational procedure of the software.

The Cy5-labeled product used for the hybridization is a group of labeled DNA fragments prepared using the genomic DNA derived from *M. intracellulare* as a material, and the Cy3-labeled product is a group of labeled DNA fragments prepared using comparative genomic DNA as a material. Therefore, when the fluorescence intensity of Cy3 and Cy5 of a certain spot on a microarray is measured, and the fluorescence of Cy5 is detected stronger, it means that the DNA fragment (PCR product) in the spot has been hybridized more strongly with the Cy5-labeled product, namely, with a particular sequence in the genomic DNA derived from *M. intracellulare*, and the specificity of the DNA fragment (PCR product) for *M. intracellulare* is deemed to high.

On the other hand, for a certain spot, when the fluorescence of Cy3 is detected more strongly than Cy5, it means that the DNA fragment (PCR product) in the spot has been hybridized with the Cy3-labeled product, namely, with the comparative genomic DNA, and the specificity of the DNA fragment (PCR product) for *M. intracellulare* is deemed to low. In addition, when the fluorescence intensity of Cy3 and Cy5 are detected in the same level, or no fluorescence of both Cy3 and Cy5 is detected, the specificity for *M. intracellulare* is also deemed to low.

And so, for example, on the basis of the fluorescence intensity ratio of Cy3/Cy5 (Ratio) detected on the microarray, and analyzing the results, for example, by making up a scatter chart (scatter plot), to carry out the screening for detecting a specific sequence for a *M. intracellulare*. In the analysis, the numeric value of Cy3/Cy5 ratio for the specific DNA for *M. intracellulare* among the positive control sequence employed will be a useful reference value for the assessment of specificity.

It should be noted that, when a positive control and a negative control are spotted on the microarray, and the fluorescence intensities of Cy3 and Cy5 in each spot are measured, the tendency of fluorescence intensities can be utilized as a data evaluation standard in the measurement by a fluorescence scanner.

Among the candidates obtained by screening, the clone which provides a significantly specific signal for *M. intracellulare* (when the fluorescence intensity of Cy5 is strong) as a result of numerical analysis of Cy3/Cy5 ratio, and yet provides a greater numerical value of the ratio (the fluorescence intensity of Cy5 is strong) compared with that of the positive control spot specific for the above described *M. intracellulare*, is selected.

In the next place, the determination of nucleotide sequence of the obtained candidate clone may be carried out according to the conventional methods using equipment such as a sequencer usually used in this field, for example, ABI PRISM310 capillary sequencer (Applied Biosystems Inc.).

It should be noted that, for the purpose of screening a candidate sequence for further specific detection of *M. intracellulare* among the selected clones, for example, secondary screening by the real-time PCR method may be performed.

Namely, on the candidate clone selected as the result of numerical analysis of the above described Cy3/Cy5 ratio, determination of nucleotide sequence is carried out. For each candidate clone, based on the obtained nucleotide sequence, and using, for example, a software commonly used for designing primer, or using, for example, a primer design tool on the web, Primer 3 (Whitehead Institute for Biomedical Research), an appropriate primer for each PCR is designed.

An appropriate combination is selected from the designed primers, and using the primers in combination, according to the conventional methods, the real-time PCR with a genomic DNA derived from *M. intracellulare* as a template is performed. In addition, using a genomic DNA derived from an appropriate bacteria strain of *Mycobacterium* genus, and further, if necessary, a genomic DNA derived from bacteria strain of other than *Mycobacterium* genus such as *E. coli* (comparison) as a template, the real-time PCR is performed in the same way. From the results, the primer combination, by which the amplification product is provided in the real-time PCR using genomic DNA derived from *M. intracellulare* as a template, and no amplification product is provided in the real-time PCR using genomic DNA derived from other bacteria strain as a template, is selected. And, the candidate clone designed for this primer combination may be selected finally as the candidate clone specific for *M. intracellulare*.

A primer for detecting *M. intracellulare* of the present invention includes the primer which comprises an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene (hereinafter, optionally referred to as the primer of the present invention).

In addition, in compliance with the conditions of the nucleic acid amplification reaction such as PCR (including the real-time PCR), nucleic acid hybridization and the like, the primer of the present invention can be used by selecting an appropriate length in an appropriate region in consideration of dissociation temperature (Tm value) and the like from the oligonucleotides which comprises a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8.

Preferably, the primer may be an oligonucleotide having a length with 10 to 50 nucleotides, more preferably 10 to 35 nucleotides, further more preferably 18 to 25 nucleotides which is considered to be a necessary nucleotide number for retaining specificity as a primer.

As to a method for designing the primer, the primer may be designed using a software commonly used for designing primer such as, for example, a primer design tool on the web, Primer 3 (Whitehead Institute for Biomedical Research) and the like.

A specific example of an oligonucleotide to be used for the primer of the present invention (the oligonucleotide of the present invention), which comprises an oligonucleotide comprising a part or the entire sequence of the nucleotide sequence shown in SEQ ID NO: 1 SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene, is the same as described in the above explanation of the oligonucleotide of the present invention.

Specific examples of the primer of the present invention include, for example, an oligonucleotide which comprises a part or the entire sequence selected from the nucleotide sequences shown in SEQ ID NO: 9 to 138, wherein the oligonucleotide is capable of hybridizing with a nucleotide sequence of *Mycobacterium intracellulare* gene, or an oligonucleotide which comprises a part or the entire sequence complementary to the oligonucleotide sequence selected from the nucleotide sequences shown in SEQ ID NO: 9 to 138, wherein the oligonucleotide is capable of hybridizing with a nucleotide sequence of *Mycobacterium intracellulare* gene.

Preferable specific examples of the primer of the present invention include an oligonucleotide which comprises a sequence selected from the nucleotide sequences shown in SEQ ID NO: 9 to 138, wherein the oligonucleotide is capable of hybridizing with a nucleotide sequence of *Mycobacterium intracellulare* gene, or an oligonucleotide which comprises a sequence complementary to the oligonucleotide sequence selected from the nucleotide sequences shown in SEQ ID NO: 9 to 138, wherein the oligonucleotide is capable of hybridizing with a nucleotide sequence of *Mycobacterium intracellulare* gene.

The more preferable primer includes, for example, an oligonucleotide which comprises a sequence selected from the nucleotide sequences shown in SEQ ID NO: 9, 10, 23, 24, 41, 42, 59, 60, 79, 80, 93, 94, 105, 106, 127, 128, or an oligonucleotide which comprises a sequence complementary to the oligonucleotide sequence selected from the nucleotide sequences shown in SEQ ID NO: 9, 10, 23, 24, 41, 42, 59, 60, 79, 80, 93, 94, 105, 106, 127, 128.

It should be noted that, the primers comprising the nucleotide sequence shown in SEQ ID NO: 9 to 22 are designed based on the nucleotide sequence shown in SEQ ID NO: 1.

The primers comprising the nucleotide sequence shown in SEQ ID NO: 23 to 40 are designed based on the nucleotide sequence shown in SEQ ID NO: 2.

The primers comprising the nucleotide sequence shown in SEQ ID NO: 41 to 58 are designed based on the nucleotide sequence shown in SEQ ID NO: 3.

The primers comprising the nucleotide sequence shown in SEQ ID NO: 59 to 78 are designed based on the nucleotide sequence shown in SEQ ID NO: 4.

The primers comprising the nucleotide sequence shown in SEQ ID NO: 79 to 92 are designed based on the nucleotide sequence shown in SEQ ID NO: 5.

The primers comprising the nucleotide sequence shown in SEQ ID NO: 93 to 104 are designed based on the nucleotide sequence shown in SEQ ID NO: 6.

The primers comprising the nucleotide sequence shown in SEQ ID NO: 105 to 126 are designed based on the nucleotide sequence shown in SEQ ID NO: 7.

The primers comprising the nucleotide sequence shown in SEQ ID NO: 127 to 138 are designed based on the nucleotide sequence shown in SEQ ID NO: 8.

In FIG. 1, in the nucleotide sequence shown in SEQ ID NO: 1, locations of the nucleotide sequences which are designed as a primer having nucleotide sequences shown in SEQ ID NO: 9 and SEQ ID NO: 10 are each indicated as 02_Fw1 and 02_Rv1 by arrows.

In FIG. 2, in the nucleotide sequence shown in SEQ ID NO: 2, locations of the nucleotide sequences which are designed as a primer having nucleotide sequences shown in SEQ ID NO: 23 and SEQ ID NO: 24 are each indicated as 03_Fw1 and 03_Rv1 by arrows.

In FIG. 3, in the nucleotide sequence shown in SEQ ID NO: 3, locations of the nucleotide sequences which are designed as a primer having nucleotide sequences shown in SEQ ID NO: 41 and SEQ ID NO: 42 are each indicated as 04_Fw2 and 04_Rv2 by arrows.

In FIG. 4, in the nucleotide sequence shown in SEQ ID NO: 4, locations of the nucleotide sequences which are designed as a primer having nucleotide sequences shown in SEQ ID NO: 59 and SEQ ID NO: 60 are each indicated as 06_Fw1 and 06_Rv1 by arrows.

In FIG. 5, in the nucleotide sequence shown in SEQ ID NO: 5, locations of the nucleotide sequences which are designed as a primer having nucleotide sequences shown in SEQ ID NO: 79 and SEQ ID NO: 80 are each indicated as 10_Fw1 and 10_Rv1 by arrows.

In FIG. 6, in the nucleotide sequence shown in SEQ ID NO: 6, locations of the nucleotide sequences which are designed as a primer having nucleotide sequences shown in SEQ ID NO: 93 and SEQ ID NO: 94 are each indicated as 13_Fw2 and 13_Rv2 by arrows.

In FIG. 7, in the nucleotide sequence shown in SEQ ID NO: 7, locations of the nucleotide sequences which are designed as a primer having nucleotide sequences shown in SEQ ID NO: 105 and SEQ ID NO: 106 are each indicated as 14_Fw1 and 14_Rv1 by arrows.

In FIG. 8, in the nucleotide sequence shown in SEQ ID NO: 8, locations of the nucleotide sequences which are designed as a primer having nucleotide sequences shown in SEQ ID NO: 127 and SEQ ID NO: 128 are each indicated as 15_Fw2 and 15_Rv2 by arrows.

In addition, in the nucleotide sequence shown in SEQ ID NO: 1, locations of the nucleotide sequences which are designed as a primer having nucleotide sequences shown in SEQ ID NO: 11 to 22 are each as follows:

SEQ ID NO: 11 (02_Fw2): $415^{th}$ to $434^{th}$;
SEQ ID NO: 12 (02_Fw3): $91^{st}$ to $110^{th}$;
SEQ ID NO: 13 (02_Fw4): $272^{nd}$ to $290^{th}$;
SEQ ID NO: 14 (02_Fw5): $245^{th}$ to $264^{th}$;
SEQ ID NO: 15 (02_Fw6): $41^{st}$ to $61^{st}$;
SEQ ID NO: 16 (02_Fw7): $423^{rd}$ to $442^{nd}$;
SEQ ID NO: 17 (02_Rv2): $563^{rd}$ to $582^{nd}$;
SEQ ID NO: 18 (02_Rv3): $294^{th}$ to $313^{th}$;
SEQ ID NO: 19 (02_Rv4): $447^{th}$ to $466^{th}$;
SEQ ID NO: 20 (02_Rv5): $373^{rd}$ to $392^{nd}$;
SEQ ID NO: 21 (02_Rv6): $175^{th}$ to $194^{th}$;
SEQ ID NO: 22 (02_Rv7): $641^{st}$ to $659^{th}$.

In the nucleotide sequence shown in SEQ ID NO: 2, locations of the nucleotide sequences which are designed as a primer having nucleotide sequences shown in SEQ ID NO: 25 to 40 are each as follows:

SEQ ID NO: 25 (03_Fw2): $18^{th}$ to $35^{th}$;
SEQ ID NO: 26 (03_Fw3): $11^{th}$ to $128^{th}$;
SEQ ID NO: 27 (03_Fw4): $229^{th}$ to $248^{th}$;
SEQ ID NO: 28 (03_Fw5): $412^{th}$ to $430^{th}$;
SEQ ID NO: 29 (03_Fw6): $580^{th}$ to $599^{th}$;
SEQ ID NO: 30 (03_Fw7): $776^{th}$ to $796^{th}$;
SEQ ID NO: 31 (03_Fw8): $873^{rd}$ to $890^{th}$;
SEQ ID NO: 32 (03_Fw9): $911^{th}$ to $930^{th}$;
SEQ ID NO: 33 (03_Rv2): $158^{th}$ to $175^{th}$;
SEQ ID NO: 34 (03_Rv3): $288^{th}$ to $306^{th}$;
SEQ ID NO: 35 (03_Rv4): $362^{nd}$ to $381^{st}$;
SEQ ID NO: 36 (03_Rv5): $542^{nd}$ to $561^{st}$;
SEQ ID NO: 37 (03_Rv6): $700^{th}$ to $719^{th}$;
SEQ ID NO: 38 (03_Rv7): $955^{th}$ to $972^{nd}$;
SEQ ID NO: 39 (03_Rv8): $1040^{th}$ to $1059^{th}$;
SEQ ID NO: 40 (03_Rv9): $1075^{th}$ to $1093^{rd}$.

In the nucleotide sequence shown in SEQ ID NO: 3, locations of the nucleotide sequences which are designed as a primer having nucleotide sequences shown in SEQ ID NO: 43 to 58 are each as follows:

SEQ ID NO: 43 (04_Fw3): $4^{th}$ to $21^{st}$;
SEQ ID NO: 44 (04_Fw4): $217^{th}$ to $235^{th}$;
SEQ ID NO: 45 (04_Fw5): $423^{rd}$ to $440^{th}$;
SEQ ID NO: 46 (04_Fw6): $476^{th}$ to $494^{th}$;
SEQ ID NO: 47 (04_Fw7): $658^{th}$ to $675^{th}$;
SEQ ID NO: 48 (04_Fw8): $709^{th}$ to $728^{th}$;
SEQ ID NO: 49 (04_Fw9): $772^{nd}$ to $789^{th}$;
SEQ ID NO: 50 (04_Fw10): $803^{rd}$ to $822^{nd}$;
SEQ ID NO: 51 (04_Rv3): $134^{th}$ to $152^{nd}$;
SEQ ID NO: 52 (04_Rv4): $367^{th}$ to $384^{th}$;
SEQ ID NO: 53 (04_Rv5): $560^{th}$ to $579^{th}$;
SEQ ID NO: 54 (04_Rv6): $605^{th}$ to $622^{nd}$;
SEQ ID NO: 55 (04_Rv7): $801^{st}$ to $820^{th}$;
SEQ ID NO: 56 (04_Rv8): $845^{th}$ to $862^{nd}$;
SEQ ID NO: 57 (04_Rv9): $899^{th}$ to $916^{th}$;
SEQ ID NO: 58 (04_Rv10): $955^{th}$ to $972^{th}$.

In the nucleotide sequence shown in SEQ ID NO: 4, locations of the nucleotide sequences which are designed as a primer having nucleotide sequences shown in SEQ ID NO: 61 to 78 are each as follows:

SEQ ID NO: 61 (06_Fw2): $153^{rd}$ to $172^{nd}$;
SEQ ID NO: 62 (06_Fw3): $1^{st}$ to $19^{th}$;
SEQ ID NO: 63 (06_Fw4): $32^{nd}$ to $49^{th}$;
SEQ ID NO: 64 (06_Fw5): $268^{th}$ to $285^{th}$;
SEQ ID NO: 65 (06_Fw6): $376^{th}$ to $395^{th}$;
SEQ ID NO: 66 (06_Fw7): $445^{th}$ to $462^{nd}$;
SEQ ID NO: 67 (06_Fw8): $492^{nd}$ to $509^{th}$;
SEQ ID NO: 68 (06_Fw9): $556^{th}$ to $574^{th}$;
SEQ ID NO: 69 (06_Fw10): $581^{st}$ to $600^{th}$;
SEQ ID NO: 70 (06_Rv2): $282^{nd}$ to $301^{st}$;
SEQ ID NO: 71 (06_Rv3): $100^{th}$ to $119^{th}$;
SEQ ID NO: 72 (06_Rv4): $184^{th}$ to $203^{rd}$;
SEQ ID NO: 73 (06_Rv5): $386^{th}$ to $405^{th}$;
SEQ ID NO: 74 (06_Rv6): $516^{th}$ to $534^{th}$;
SEQ ID NO: 75 (06_Rv7): $575^{th}$ to $594^{th}$;
SEQ ID NO: 76 (06_Rv8): $656^{th}$ to $675$;
SEQ ID NO: 77 (06_Rv9): $686^{th}$ to $705^{th}$;
SEQ ID NO: 78 (06_Rv10): $703^{rd}$ to $720^{th}$.

In additions in the nucleotide sequence shown in SEQ ID NO: 5, locations of the nucleotide sequences which are designed as a primer having nucleotide sequences shown in SEQ ID NO: 81 to 92 are each as follows:

SEQ ID NO: 81 (10_Fw2): 388$^{th}$ to 407$^{th}$;
SEQ ID NO: 82 (10_Fw3): 2$^{nd}$ to 19$^{th}$;
SEQ ID NO: 83 (10_Fw4): 122$^{nd}$ to 141$^{st}$;
SEQ ID NO: 84 (10_Fw5): 207$^{th}$ to 226$^{th}$;
SEQ ID NO: 85 (10_Fw6): 298$^{th}$ to 318$^{th}$;
SEQ ID NO: 86 (10_Fw7): 459$^{th}$ to 478$^{th}$;
SEQ ID NO: 87 (10_Rv2): 541$^{st}$ to 560$^{th}$;
SEQ ID NO: 88 (10_Rv3): 150$^{th}$ to 169$^{th}$;
SEQ ID NO: 89 (10_Rv4): 276$^{th}$ to 294$^{th}$;
SEQ ID NO: 90 (10_Rv5): 370$^{th}$ to 289$^{th}$;
SEQ ID NO: 91 (10_Rv6): 453$^{rd}$ to 472$^{nd}$;
SEQ ID NO: 92 (10_Rv7): 593$^{rd}$ to 610$^{th}$.

In the nucleotide sequence shown in SEQ ID NO: 6, locations of the nucleotide sequences which are designed as a primer having nucleotide sequences shown in SEQ ID NO: 95 to 104 are each as follows:

SEQ ID NO: 95 (13_Fw3): 56$^{th}$ to 75$^{th}$;
SEQ ID NO: 96 (13_Fw4): 129$^{th}$ to 148$^{th}$;
SEQ ID NO: 97 (13_Fw5): 200$^{th}$ to 219$^{th}$;
SEQ ID NO: 98 (13_Fw6): 333$^{rd}$ to 352$^{nd}$;
SEQ ID NO: 99 (13_Fw7): 286$^{th}$ to 305$^{th}$;
SEQ ID NO: 100 (13_Rv3): 225$^{th}$ to 244$^{th}$;
SEQ ID NO: 101 (13_Rv4): 242$^{nd}$ to 261$^{st}$;
SEQ ID NO: 102 (13_Rv5): 325$^{th}$ to 343$^{rd}$;
SEQ ID NO: 103 (13_Rv6): 481$^{st}$ to 500$^{th}$;
SEQ ID NO: 104 (13_Rv7): 416$^{th}$ to 435$^{th}$.

In the nucleotide sequence shown in SEQ ID NO: 7, locations of the nucleotide sequences which are designed as a primer having nucleotide sequences shown in SEQ ID NO: 107 to 126 are each as follows:

SEQ ID NO: 107 (14_Fw3): 11$^{th}$ to 29$^{th}$;
SEQ ID NO: 108 (14_Fw4): 73$^{rd}$ to 92$^{nd}$;
SEQ ID NO: 109 (14_Fw5): 201$^{st}$ to 220$^{th}$;
SEQ ID NO: 110 (14_Fw6): 413$^{th}$ to 431$^{st}$;
SEQ ID NO: 111 (14_Fw7): 519$^{th}$ to 538$^{th}$;
SEQ ID NO: 112 (14_Fw8): 657$^{th}$ to 674$^{th}$;
SEQ ID NO: 113 (14_Fw9): 596$^{th}$ to 613$^{th}$;
SEQ ID NO: 114 (14_Fw10): 618$^{th}$ to 635$^{th}$;
SEQ ID NO: 115 (14_Fw11): 864$^{th}$ to 883$^{rd}$;
SEQ ID NO: 116 (14_Fw12): 806$^{th}$ to 824$^{th}$;
SEQ ID NO: 117 (14_Rv3): 158$^{th}$ to 177$^{th}$;
SEQ ID NO: 118 (14_Rv4): 208$^{th}$ to 227$^{th}$;
SEQ ID NO: 119 (14_Rv5): 337$^{th}$ to 356$^{th}$;
SEQ ID NO: 120 (14_Rv6): 548$^{th}$ to 565$^{th}$;
SEQ ID NO: 121 (14_Rv7): 669$^{th}$ to 688$^{th}$;
SEQ ID NO: 122 (14_Rv8): 782$^{nd}$ to 800$^{th}$;
SEQ ID NO: 123 (14_Rv9): 721$^{st}$ to 740$^{th}$;
SEQ ID NO: 124 (14_Rv10): 755$^{th}$ to 773$^{rd}$;
SEQ ID NO: 125 (14_Rv11): 978$^{th}$ to 997$^{th}$;
SEQ ID NO: 126 (14_Rv12): 967$^{th}$ to 986$^{th}$.

In the nucleotide sequence shown in SEQ ID NO: 8, locations of the nucleotide sequences which are designed as a primer having nucleotide sequences shown in SEQ ID NO: 129 to 138 are each as follows:

SEQ ID NO: 129 (15_Fw3): 28$^{th}$ to 45$^{th}$;
SEQ ID NO: 130 (15_Fw4): 64$^{th}$ to 82$^{nd}$;
SEQ ID NO: 131 (15_Fw5): 131$^{st}$ to 148$^{th}$;
SEQ ID NO: 132 (15_Fw6): 348$^{th}$ to 366$^{th}$;
SEQ ID NO: 133 (15_Fw7): 462$^{nd}$ to 481$^{st}$;
SEQ ID NO: 134 (15_Rv3): 182$^{nd}$ to 200$^{th}$;
SEQ ID NO: 135 (15_Rv4): 197$^{th}$ to 215$^{th}$;
SEQ ID NO: 136 (15_Rv5): 270$^{th}$ to 287$^{th}$;
SEQ ID NO: 137 (15_Rv6): 451$^{st}$ to 470$^{th}$;
SEQ ID NO: 138 (15_Rv7): 619$^{th}$ to 636$^{th}$.

It should be noted that, in the above description, names of the primers denominated in the present invention are shown in parenthesis next to each SEQ ID NO.

Method for obtaining the primer of the present invention is as described above in the method for obtaining the nucleotide of the present invention.

In addition, the primer of the present invention may be labeled with a labeling substance.

Method for labeling the primer of the present invention includes the labeling methods of the oligonucleotide usually conducted in this field, and the methodology may be selected appropriately depending on the labeling substance.

As to the labeling substance to be used for labeling the primer of the present invention, any of known labeling substances such as radioisotope, enzyme, fluorescent substance, luminescent substance, biotin and the like may be used.

For example, the radioisotope includes $^{32}$P, $^{33}$P, $^{35}$S and the like; the enzyme includes alkaline phosphatase, horseradish peroxydase and the like; the fluorescent substance includes cyanine dye type of Cy3, Cy5 (Amersham Biosciences K.K.), fluorescein and the like; the luminescent substance includes chemiluminescent reagents including acridinium esters and the like.

The method for labeling the primer of the present invention with a radioisotope includes the method of labeling by incorporation of a radioisotope-labeled nucleotide into a primer at the time when the primer is synthesized, or labeling with a radioisotope after the primer is synthesized and the like. Specifically, as popularly used methods, random primer method, nick-translation method, 5'-terminal labeling method using T4 polynucleotide kinase, 3'-terminal labeling method using terminal deoxynucleotide transferase, RNA labeling method and the like are included.

The method for labeling the primer of the present invention with enzyme includes a direct labeling method, a conventional technique in this field, in which an enzyme molecule such as alkaline phosphatase, horseradish peroxidase and the like is directly and covalently linked to the primer to be labeled.

As to the method for labeling the primer of the present invention with fluorescent substance includes, for example, the fluorescent-labeled nucleotide may be incorporated into the primer by a conventional labeling technique in this field. In addition, by a method of replacing a nucleotide in a sequence with a nucleotide having a linker arm as a member of the sequence (See, for example, Nucleic Acids Res., 1986, vol. 14, p. 6115), the nucleotide can also be labeled with fluorescent substance. In this case, there may be a method in which a uridine having a linker arm on 5-position is synthesized chemically from deoxyuridine by a synthesis method disclosed in JP-A-1985-500717, and using it, a fluorescent substance is introduced into the above described oligonucleotide.

In order to label the primer of the present invention with a luminescent substance or biotin, the labeling may be carried out according to the conventional a technique of luminescent-labeling or biotin-labeling usually conducted for nucleotides in this field.

A probe for detecting *M. intracellulare* of the present invention includes a probe which comprises an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene (hereinafter, optionally referred to as the probe of the present invention).

In compliance with the conditions of the nucleic acid amplification reaction such as PCR (including the real-time PCR), nucleic acid hybridization and the like, the probe of the present invention can be used by selecting an appropriate length in an appropriate region in consideration of dissociation temperature (Tm value) and the like from the oligonucleotides which comprise a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of the sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8. In this regard, however, if the probe is intended to have sufficient specificity, it is desirable to design the probe in consideration of nucleotide number necessary for retaining specificity as a probe.

For example, the probe to be used for the nucleic acid hybridization method (for example, Southern hybridization, and the like) includes a probe having a length of 10 to 700 nucleotides, preferably 100 to 600 nucleotides, more preferably 100 to 500 nucleotides, and further more preferably 200 to 500 nucleotides.

For example, the probe to be used for the real-time PCR amplification system (for example, TaqMan™ method, Molecular Beacon method, and the like) includes the one having a length of 10 to 50 nucleotides, preferably 15 to 40 nucleotides, more preferably 20 to 30 nucleotides.

A specific example of the oligonucleotide to be used for the probe of the present invention (the oligonucleotide of the present invention), which comprises a part or the entire sequence of the nucleotide sequence shown in SEQ ID NO: 1, SEQ ID NO: 2, SEQ ID NO: 3, SEQ ID NO: 47 SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene, is the same as described in the above explanation of the oligonucleotide of the present invention.

A specific example of the probe of the present invention includes, for example, the one selected from the probe comprising an oligonucleotide which comprises a part or the entire sequence of the sequence selected from the nucleotide sequences shown in SEQ ID NO: 9 to 203, or a pan or an entire sequence of the sequence complementary to the nucleotide sequence selected from the nucleotide sequences shown in SEQ ID NO: 9 to 203, wherein the oligonucleotide is capable of hybridizing with a nucleotide sequence of *Mycobacterium intracellulare* gene.

In particular, a preferable example of the probe of the present invention includes the one which comprises a sequence selected from the nucleotide sequences shown in SEQ ID NO: 9 to 203, or the one which comprises a sequence complementary to the nucleotide sequence selected from the nucleotide sequences shown in SEQ ID NO: 9 to 203. Among them, the one which comprises a sequence selected from nucleotide sequences shown in SEQ ID NO: 139 to 203, or the one which comprises a sequence complementary to the nucleotide sequence selected from the nucleotide sequences shown in SEQ ID NO: 139 to 203 are included. Particularly preferable probe includes the one which comprises a sequence selected from the nucleotide sequences shown in SEQ ID NO: 139, 146, 155, 164, 174, 181, 187 and 198, or the one which comprises a sequence complementary to the nucleotide sequence selected from the nucleotide sequences shown in SEQ ID NO: 139, 146, 155, 164, 174, 181, 187 and 198.

It should be noted that, the nucleotide sequences shown in SEQ ID NO: 139 to 203 or the sequence complementary to the nucleotide sequences shown in SEQ ID NO: 139 to 203 is the nucleotide sequence of the oligonucleotide to be amplified by the PCR using the primer of the present invention. Combinations of the forward primer and the reverse primer, and the SEQ ID NO of the nucleotide sequence to be amplified by the PCR using such a combination of primers are shown collectively in Table 1. For example, the nucleotide sequence shown in SEQ ID NO: 139 is a sequence which is amplified by the PCR using an oligonucleotide having a nucleotide sequence shown in SEQ ID NO: 9 as a forward primer and an oligonucleotide having a nucleotide sequence shown in SEQ ID NO: 10 as a reverse primer.

TABLE 1

| Forward primer | Reverse primer | Sequence to be amplified |
|---|---|---|
| 9 | 10 | 139 |
| 11 | 17 | 140 |
| 12 | 18 | 141 |
| 13 | 19 | 142 |
| 14 | 20 | 143 |
| 15 | 21 | 144 |
| 16 | 22 | 145 |
| 23 | 24 | 146 |
| 25 | 33 | 147 |
| 26 | 34 | 148 |
| 27 | 35 | 149 |
| 28 | 36 | 150 |
| 29 | 37 | 151 |
| 30 | 38 | 152 |
| 31 | 39 | 153 |
| 32 | 40 | 154 |
| 41 | 42 | 155 |
| 43 | 51 | 156 |
| 44 | 52 | 157 |
| 45 | 53 | 158 |
| 46 | 54 | 159 |
| 47 | 55 | 160 |
| 48 | 56 | 161 |
| 49 | 57 | 162 |
| 50 | 58 | 163 |
| 59 | 60 | 164 |
| 61 | 70 | 165 |
| 62 | 71 | 166 |
| 63 | 72 | 167 |
| 64 | 73 | 168 |
| 65 | 74 | 169 |
| 66 | 75 | 170 |
| 67 | 76 | 171 |
| 68 | 77 | 172 |
| 69 | 78 | 173 |
| 79 | 80 | 174 |
| 81 | 87 | 175 |
| 82 | 88 | 176 |
| 83 | 89 | 177 |
| 84 | 90 | 178 |
| 85 | 91 | 179 |
| 86 | 92 | 180 |
| 93 | 94 | 181 |
| 95 | 100 | 182 |
| 96 | 101 | 183 |
| 97 | 102 | 184 |
| 98 | 103 | 185 |
| 99 | 104 | 186 |
| 105 | 106 | 187 |
| 107 | 117 | 188 |
| 108 | 118 | 189 |

TABLE 1-continued

| Forward primer | Reverse primer | Sequence to be amplified |
|---|---|---|
| 109 | 119 | 190 |
| 110 | 120 | 191 |
| 111 | 121 | 192 |
| 112 | 122 | 193 |
| 113 | 123 | 194 |
| 114 | 124 | 195 |
| 115 | 125 | 196 |
| 116 | 126 | 197 |
| 127 | 128 | 198 |
| 129 | 134 | 199 |
| 130 | 135 | 200 |
| 131 | 136 | 201 |
| 132 | 137 | 202 |
| 133 | 138 | 203 |

The method for obtaining the probe of the present invention is as described above in the method for obtaining the nucleotide of the present invention.

The probe of the present invention may be labeled with a labeling substance.

As to the labeling substance to be used for labeling the probe of the present invention, any of the known labeling substances such as radioisotope and enzyme, fluorescent substance, luminescent substance, biotin and the like may be used.

The specific examples of the labeling substance and the labeling method to be used for labeling the probe of the present invention are as described in the labeling method of the primer of the present invention.

In addition, the labeled probe to be used in the real-time PCR method as described later includes the probe of the present invention labeled with a labeling substance usually used in the real-time detection method. For example, the labeled probe of the present invention in which the 5'-terminal is labeled with a reporter fluorescent substance [carboxyfluorescein (FAM), hexachlorofluorescein (HEX), tetrachlorofluorescein (TET) and the like] and 3'-terminal is labeled with a quencher dye [for example, a fluorescent substance such as carboxytetramethylrhodamine (TAMRA), nonfluorescent substance such as Black Hole Quencher dye (BHQ) and 4-((4-(dimethylamino) phenyl)azo)benzoic acid (DABCYL), and the like] is included.

In the method for detection by the TaqMan™ real-time PCR method to be described hereinafter, the above described labeled probe can also be used.

Sample to be used for detecting *M. intracellulare* of the present invention includes various kinds of clinical specimen such as sputum blood, pharyngeal mucosa, gastric juice, bronchial washing fluid, transbronchial specimen, puncture fluid such as pleural effusion, urine, pus, and the like. In addition, the sample may be the microbial cell isolated and cultured from a specimen; the nucleic acid isolated and purified from such microbial cell; or the nucleic acid amplified by the nucleic acid amplification detection system and the like.

The extraction and purification of the DNA from the above described samples may be carried out according to the conventional procedures usually used for the extraction of acid-fast bacterium (tuberculosis bacterium) DNA from a specimen.

First, the cell wall of microbial cell in the sample is needed to be broken down. The method for this purpose includes, for example, in the case where the microbial cell is used as a sample, a method for disruption of the membrane structure of tuberculosis bacterium by treating the microbial cell with, for example, surface active agent such as SDS, protein denaturing agent such as guanidine thiocyanate (GTC), and a method of physical disruption of the microbial cell using glass beads and the like.

In the case where the expectorated sputum is used as a sample, as a pretreatment, it is desirable to conduct homogenization of the specimen material by NALC (N-acetyl-L-cysteine)-NaOH method (Kent P T, Kubica G P, Public Health Mycobacteriology, A Guide for the Level III Laboratory, U.S. Department of Health and Human Services, Public Health Service, Center for Disease Control, Atlanta, U.S.A., 1985, p. 31-55) according to the recommendation from Center for Disease Control and Prevention (CDC).

After disruption of cell wall of the microbial cell, extraction and purification of DNA may be carried out by a conventional method for preparation of DNA in this field (phenol-chloroform extraction, ethanol precipitation method and the like, Rapid and simple method for purification of nucleic acids, the method described in J. Clin. Microbiol., 1990, Mar; 28 (3), 495-503, Boom R, Sol CJ, Salimans MM, Jansen CL, Wertheim-van Dillen PM, van der Noordaa J, and the method for precipitation using isopropanol and the like).

Taking a case where the isolated and cultured microbial cell from specimen is used as a sample for detecting *M. intracellulare* as an example, the procedure is shown as follows.

For example, colonies grown on the Ogawa's medium are collected; suspended in sterile distilled water; centrifuged to collect microbial cell; the microbial cell is resuspended in distilled water and autoclaved; after disruption treatment (physical disruption using glass beads and the like), the disrupted microbial cell is further centrifuged to recover supernatant fluid. The DNA may be extracted and purified from the obtained supernatant fluid.

For extraction and purification of DNA, as various types of kits for this purpose are commercially available, such kits may be utilized, or the extraction may be carried out according to the conventional procedures in this field (for example, phenol-chloroform extraction method, precipitation method using ethanol, propanol and the like). For example, using an ion exchange resin type DNA extraction and purification kit of Genomic-tip (QIAGEN GmbH) and the like, the extraction and purification of the DNA may be carried out.

The method for detecting *M. intracellulare* of the present invention includes, a method which utilizes an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene as a primer and/or a probe (the method using the primer and/or the probe of the present invention).

For example, the following methods are included:

(A) a method in which, using an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene (the oligonucleotide of the present invention) as a primer, the nucleic acid amplification reaction is performed, then the obtained primer extension product is detected;

(B) a method in which the oligonucleotide of the present invention is labeled with a labeling substance, and is used as a labeled probe.

Each method will be explained below.

(A) The Method in which the nucleic Acid Amplification Reaction is Performed using the Oligonucleotide of the Present Invention as a Primer, then the Obtained Primer Extension Product is Detected In the aforementioned method, the method (A) of performing the nucleic acid amplification reaction using the oligonucleotide of the present invention as a primer includes, for example, a method in which, using the primer of the present invention and using the nucleic acid in the sample as a template, the nucleic acid amplification by DNA polymerase and the like [for example, the polymerase chain reaction (PCR) method (JP-A-1985-281); LAMP (Loop-mediated Isothermal Amplification) method (Tsugunori Notomi et al., Nucleic Acid Res., 28, e63, 2000), ICANTM (Isothermal and Chimeric primer-initiated Amplification of Nucleic acids) method (Rinsho Byori (Clinical Pathology), 51 (11), 1061-1067, 2003, November), LCR (ligase chain reaction) method (JP-A-1992-211399), SDA (strand displacement amplification) method (JP-A-1996-19394)] is performed to allow primer extension. And, by this method, the sequence of a specific region of the nucleotide sequence of M. intracellulare gene can be amplified, and thus M. intracellulare can be detected by measuring the obtained primer extension product.

Among the above described methods of the nucleic acid amplification reaction, the PCR method is quoted as the most common method; and an example of the PCR method includes, for example, the real-time amplification detection system (see, for example, the description in U.S. Pat. No. 5,210,015 and U.S. Pat. No. 5,538,848). In addition, an example of the detection system by the real-time amplification detection system includes, for example, the real-time PCR detection method.

An example of the real-time PCR detection method includes TaqMan™ real-time PCR method (see, for example, the description in U.S. Pat. No. 5,538,848), MGB Eclipse Probe System method (see, for example, the description in U.S. Pat. No. 5,801,155), Molecular Beacons Probe Technology method (see, for example, the description in U.S. Pat. No. 5,925,517), LUX Fluorogenic Primer method (Invitrogen Corp.), Quenching probe-PCR (QP) method (see, for example, the description in U.S. Pat. No. 6,492,121), and the like.

Specific examples of the primer of the present invention to be used in the nucleic acid amplification reaction such as the PCR are as described above.

In addition, preferable combinations of the forward primer and the reverse primer to be used in the nucleic acid amplification reaction include the combinations shown in the above described Table 1.

Among them, preferable combinations of the forward primer and the reverse primer include, for example, the following combinations:

(1) A combination of the primers wherein the forward primer is an oligonucleotide comprising the nucleotide sequence shown in SEQ ID NO: 9 and the reverse primer is an oligonucleotide comprising the nucleotide sequence shown in SEQ ID NO: 10;

(2) A combination of the primers wherein the forward primer is an oligonucleotide comprising the nucleotide sequence shown in SEQ ID NO: 23 and the reverse primer is an oligonucleotide comprising the nucleotide sequence shown in SEQ ID NO: 24;

(3) A combination of the primers wherein the forward primer is an oligonucleotide comprising the nucleotide sequence shown in SEQ ID NO: 41 and the reverse primer is an oligonucleotide comprising the nucleotide sequence shown in SEQ ID NO: 42;

(4) A combination of the primers wherein the forward primer is an oligonucleotide comprising the nucleotide sequence shown in SEQ ID NO: 59 and the reverse primer is an oligonucleotide comprising the nucleotide sequence shown in SEQ ID NO: 60;

(5) A combination of the primers wherein the forward primer is an oligonucleotide comprising the nucleotide sequence shown in SEQ ID NO: 79 and the reverse primer is an oligonucleotide comprising the nucleotide sequence shown in SEQ ID NO: 80;

(6) A combination of the primers wherein the forward primer is an oligonucleotide comprising the nucleotide sequence shown in SEQ ID NO: 93 and the reverse primer is an oligonucleotide comprising the nucleotide sequence shown in SEQ ID NO: 94;

(7) A combination of the primers wherein the forward primer is an oligonucleotide comprising the nucleotide sequence shown in SEQ ID NO: 105 and the reverse primer is an oligonucleotide comprising the nucleotide sequence shown in SEQ ID NO: 106;

(8) A combination of the primers wherein the forward primer is an oligonucleotide comprising the nucleotide sequence shown in SEQ ID NO: 127 and the reverse primer is an oligonucleotide comprising the nucleotide sequence shown in SEQ ID NO: 128

Other reagents such as deoxyribonucleoside triphosphate (dATP, dCTP dGTP, dTTP), the DNA polymerase and the like to be used for the nucleic acid amplification reaction such as the real-time PCR using the above described primers may be the reagents commonly used in this field; and the conditions and the procedures and the like, except for the use of the primer and the probe of the present inventions may be performed according to the general protocol of the PCR.

Method for detection of the primer extension product obtained by the nucleic acid amplification reaction may be the conventional procedures commonly conducted in this field, and is not limited specifically.

For example, various detection methods are included such as intercalator method; TaqMan™ real-time PCR method (see, for example, the description in U.S. Pat. No. 5,538,848); MGB Eclipse Probe System method (see, for example, the description in U.S. Pat. No. 5,801,155); Molecular Beacons Probe Technology method (see, for example, the description in U.S. Pat. No. 5,925,517); LUX Fluorogenic Primer method (invitrogen Corporation); Quenching probe-PCR (QP) method (see, for example, the description in U.S. Pat. No. 6,492,121); a method in which, after the nucleic acid amplification reaction is performed, the primer extension products obtained are subjected to electrophoresis, and the detection is performed based on the results of the electrophoresis; a method in which determination is performed by measuring the signal derived from the primer extension product obtained by the nucleic acid amplification reaction using a labeled primer; and the like.

Among them, generally the method commonly used includes, for example, the following methods:

(A-1) Intercalator method;

(A-2) TaqMan™ real-time PCR method;

(A-3) A method in which, after the nucleic acid amplification reaction is performed, the primer extension products obtained are subjected to electrophoresis, and the detection is performed based on the results of the electrophoresis; and (A-4) A method in which the determination is carried out by measuring the signal derived from the primer extension product obtained by the nucleic acid amplification reaction using the labeled primer.

Each of these methods will be explained below.

(A-1) Intercalator Method

Conventional intercalator method in which the real-time PCR is performed by using known intercalator, can be utilized.

For example, a method in which, using the primer of the present invention and an intercalator, the real-time PCR is performed by using a conventional intercalator method, is included.

That is, the intercalator is a reagent capable of generating fluorescence by binding specifically with a double-stranded DNA, and generates fluorescence when exposed to excitation light. When DNA is increased by repeated amplification of PCR, the intercalator is incorporated into the DNA accordingly. That is, as the amount of the intercalator incorporated into DNA is proportion to the amount of the amplification product, the amount of the primer extension product can be determined by detecting an fluorescence intensity derived from the intercalator.

In this regard, however, since the intercalator binds to all of the double-stranded DNAs, melting curve analysis may be carried out based on the measurement results of fluorescence intensity, if necessary. Namely, after conducting the PCR, the fluorescence intensity derived from the intercalator is measured, while temperature of the reaction solution of PCR is gradually increased. In the beginning, the PCR amplification product generates fluorescence because it forms double strand. However, when temperature of the reaction solution of PCR reaches to a certain temperature, the amplification products will dissociate to a single strand, and the intensity of the fluorescence derived from the intercalator decreases immediately. The temperature at this point is the melting temperature (Tm value), and is an specific value of the sequence of a primer extension product. A specific product and a non-specific product may be determined from this Tm value.

This intercalator method does not require any electrophoretic procedure after the real-time PCR, and therefore, is an effective method in the case where a rapid determination is required in the field of clinical testing.

The intercalator to be used in the present invention includes, any type of intercalator usually used in this field can be utilized, and the intercalator includes, for example, SYBR™ Green I (Molecular Probes Inc.), ethidium bromide, fluorine and the like.

An example of "the method for detecting M. intracellulare through the use of intercalator method" of the present invention would be explained as follows:

Using the primer of the present invention and the intercalator (for example, SYBR™ Green I), and using a purified DNA sample purified from a sample to be detected for M. intracellulare as a template, the real-time PCR is performed with the use of a polymerase such as Taq DNA polymerase. And, by the method of increasing the temperature described above, the fluorescence intensity derived from the intercalator (SYBR™ Green I) intercalated into the primer extension products is measured.

After that, by plotting the melting temperature of the primer extension product (double-stranded DNA) as horizontal axis and the first derivation (variation) of fluorescence intensity as vertical axis, the melting curve analysis of the primer extension product is carried out, and thereby detection of peak is examined. When a single peak is obtained, it can be determined that the sample is positive for M. intracellulare (that is, there exist M. intracellulare strain or the gene thereof; and hereinafter, the same as above).

Or otherwise, a dilution series of the purified DNA sample solution is prepared, and for each dilution series, the real-time PCR is performed in the same way as described above. After that, the melting curve is depicted by plotting the melting temperature of the primer extension product (double-stranded DNA) as horizontal axis and the first derivation (variation) of fluorescence intensity as vertical axis, and then the melting curve analysis of the amplification product is performed to detect the peak.

In this instance, in the method for detecting M. intracellulare, when the peaks with identical Tm value for each primer extension product of each dilution series is detected in the melting curve analysis, it may be determined that the sample is positive for M. intracellulare.

In addition, based on the measurement value obtained by the method through the use of the intercalator method, a standard curve can also be made up according to the condition employed for performing the realtime PCR, and thereby, using the standard curve, the quantity (copy number) of genomic DNA of M. intracellulare in a sample can be obtained.

The method of making the standard curve and the assay method of M. intracellulare will be described later.

As an example of the method for detecting M. intracellulare by the real-time PCR detection method using the intercalator of the present invention, taking a case where M. intracellulare is detected using the above described "Primer 02_Fw1" and "Primer 02_Rv1", the method will be explained as follows.

At first, by known method, the purified DNA sample is obtained from the sample to be detected for M. intracellulare.

Separately, using a DNA synthesizer, an oligonucleotide (02_Fw1) consisting of the nucleotide sequence shown in SEQ ID NO: 9 and an oligonucleotide (02_Rv1) consisting of the nucleotide sequence shown in SEQ ID NO: 10 are synthesized by the phosphoramidite method.

Using the 02_Fw1 synthesized above as a forward primer and the 02_Rv1 as a reverse primer, the real-time PCR is performed, for example, as follows.

That is, a 10 mM Tris-HCl buffer solution (pH 8.9) containing each 50 to 2000 nM of the primer 02_Fw1 and the primer 02_Rv1, about 5000 to 100000 times dilution of the concentrate solution of intercalator [for example, SYBR™ Green I (product name of Molecular Probe Inc.)], 1.0 to 4.0 mM $MgCl_2$, KCl, BSA, sodium cholate, 0.005 to 0.2% TritonX-100, 0.2 nM each of dATP, dCTP, dGTP and dTTP, and 10 to 80 unit/ml of polymerase (for example, Taq DNA polymerase) is prepared, and used as a reaction solution for PCR. To the aforementioned reaction solution for PCR, the purified DNA sample purified from a sample to be detected for M. intracellulare is added, and used as a DNA sample for PCR. This sample for PCR is placed in each well of 96-well reaction plate, and the real-time PCR is performed using real-time PCR a detection equipment and the like. The reaction is repeated for 30 to 50 cycles, and the fluorescence intensity derived from the intercalator (for example, SYBR™ Green I) intercalated into the primer amplification products is measured at each cycle.

After that, the melting curve is depicted by plotting the melting temperature of the primer extension product (double-stranded DNA) as horizontal axis and the first derivation (variation) of fluorescence intensity as vertical axis, and the melting curve analysis of the primer extension product is carried out to detect the peak. When a single peak is obtained, it may be determined that the sample is positive for *M. intracellulare*.

Or otherwise, a dilution series of the purified DNA sample solution is prepared, and for each dilution series, the real-time PCR is performed in the same way as described above. After that, the melting curve is depicted by plotting the melting temperature of the primer extension product (double-stranded DNA) as horizontal axis and the first derivation (variation) of fluorescence intensity as vertical axis, and then the melting curve analysis of the primer extension product is performed to analyze the detected peak.

In this instance, as for the method of detecting *M. intracellulare*, when the peaks with identical Tm value for each primer extension product of each dilution series are detected in the melting curve analysis, it may be determined that the sample is positive for *M. intracellulare*.

In addition, as a reference (comparison), a DNA derived from *Mycobacterium* genus other than *M. intracellulare* is extracted and purified. The real-time PCR is performed according to the same method as described above except for the use of this DNA as a template; and fluorescence intensity derived from SYBR™ Green I is measured in the same way; and then the melting curve analysis may be carried out. In this case, as there is no nucleotide sequence derived from *M. intracellulare* in the sample, no peak should appear in the melting curve analysis. To make the determination of *M. intracellulare* more assured, it is desirable to conduct the above described control experiment in parallel.

Further, by making a standard curve, number of the genomic DNA (the copy number) of *M. intracellulare* in the sample can be obtained. In addition, as the number is proportional to number of *M. intracellulare*, the number of *M. intracellulare* in the sample can also be determined.

(A-2) TaqMan™ Real-Time PCR Method (TaqMan™ Probe Method)

The TaqMan™ real-time PCR method is a real-time PCR method using a probe in which the 5'-terminal thereof is labeled with a fluorescent dye (reporter) such as, for example, FAM, and the 3'-terminal thereof is labeled with a quencher dye such as, for example, TAMRA, and is a method capable of detecting a small amount of target DNA with high sensitivity and quantitatively (see, for example, the document in U.S. Pat. No. 5,538,848).

More specifically, using an oligonucleotide which comprises a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene as a primer (the primer of the present invention), and using a labeled oligonucleotide which is labeled with a reporter fluorescent dye on the 5'-terminal and with a quencher dye on the 3'-terminal as a labeled probe, which comprises a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene (the oligonucleotide of the present invention), the PCR is performed with the nucleic acid in a sample as a template, and then the signal derived from labeling substance released from aforementioned labeled probe is detected.

The principle of the TaqMan™ real-time PCR method is as follows:

In this method, an oligonucleotide probe, which is labeled with a fluorescent dye (reporter) on the 5'-terminal thereof and with a quencher dye on the 3'-terminal thereof, and is capable of hybridizing with a specific region in the target gene, is used. In the aforementioned probe, the fluorescence of the reporter is suppressed by the quencher dye under normal condition. Under the state where this fluorescent probe is hybridized completely with the target gene, the PCR is performed from the outside thereof using a DNA polymerase. As the extension reaction by the DNA polymerase progresses, the fluorescent probe is hydrolyzed away from the 5'-terminal by the exonuclease activity of the DNA polymerase, and the released reporter dye generates the fluorescence. The real-time PCR method is a method of monitoring the intensity from this fluorescence in real time, and thereby, the initial amount of the template DNA can be quantified accurately.

For the forward primer and the reverse primer to be used for the TaqMan™ real-time PCR detection system of the present invention, the primer of the present invention is utilized. The preferable primer includes the primer to be used in the nucleic acid amplification reaction such as the above described PCR method, and the preferable combination thereof are also as described above.

The probe to be used for labeling with a fluorescent dye (reporter) on the 5'-terminal thereof and a quencher dye on the 3'-terminal thereof, and which is used for the TaqMan™ real-time PCR detection method of the present invention, may be the probe of the present invention described above. In a practical sense, a probe comprising a nucleotide sequence of primer extension product which is anticipated to be obtained when the real-time PCR is performed by the combinational use of a selected forward primer and a reverse primer, or a probe comprising a nucleotide sequence designed further from such sequence may be used. For example, the probe which is used when the real-time PCR is performed by the combinational use of two primers of 02_Fw1 (having a nucleotide sequence shown in SEQ ID NO: 9) and 02_Rv1 (having a nucleotide sequence shown in SEQ ID NO: 10) includes a nucleotide comprising a nucleotide sequence shown in SEQ ID NO: 139 which is anticipated to be amplified in the real-time PCR thereof, or an oligonucleotide comprising a sequence designed from a nucleotide sequence shown in SEQ ID NO: 139 (for example, a sequence shown in SEQ ID NO: 204).

The reporter fluorescent substance for labeling the 5'-terminal of the labeled probe includes carboxyfluorescein (FAM), hexachlorofluorescein (HEX), tetrachlorofluorescein (TET), Cy5, VIC and the like, however, FAM is used commonly among them. The quencher dye for labeling the 3'-terminal includes fluorescent substance such as carboxytetramethyl-rhodamine (TAMRA), nonfluorescent substance such as Black Hole Quencher dye (for example, BHQ2), 4-((4-

(dimethylamino) phenyl)azo)benzoic acid (DABCYL), however, TAMRA is used commonly among them.

Other reagents to be used for the real-time PCR detection system such as deoxyribonucleoside 3-phosphate (dATP, dCTP, dGTP, dTTP) and DNA polymerase may be the same reagents as usually used in the conventional real-time PCR, and the procedure of the real-time PCR may be performed according to the customary protocol of the real-time PCR except for the use of the primer and the probe of the present invention.

An example of the method for detecting *M. intracellulare* by the TaqMan™ real-time PCR detection system of the present invention will be explained as follows:

First, according to a known method (for example, above described method), a purified DNA sample is obtained from the sample to be detected for *M. intracellulare*. Separately, using a DNA synthesizer, an oligonucleotide (02_Fw1) consisting of the nucleotide sequence shown in SEQ ID NO; 9 and an oligonucleotide (02_Rv1) consisting of the nucleotide sequence shown in SEQ ID NO; 10 are synthesized by the phosphoramidite method.

In addition, from the nucleotide sequence shown in SEQ ID NO: 138 which is anticipated to be amplified by the PCR using 02_Fw1 and 02_Rv1 as primers, a sequence for use as a probe (for example, the sequence shown in SEQ ID No: 204) is designed, and an oligonucleotide with this nucleotide sequence is synthesized. The 5'-terminal of this oligonucleotide is coupled with a reporter dye of FAM, and the 3'-terminal with a reporter quencher of TAMRA by the conventional procedures, and thereby a fluorescence labeled probe is obtained.

Using the above-prepared 02_Fw1 as a forward primer and the 02_Rv1 as a reverse primer, the real-time PCR is performed, for example, as follows:

That is, a 10 mM Tris-HCl buffer solution (pH 8.9) containing each 0.1 to 2 µM, preferably each 1 µM of the primer 02_Fw1 and the primer 02_Rv1, 100 to 1000 nM fluorescence-labeled probe, 1.0 to 4.0 mM $MgCl_2$, KCl, BSA, sodium cholate, 0.005 to 0.2% TritonX-100, each about 0.2 mM of dATP, dCTP, dGTP and dTTP, and 10 to 80 unit/ml of polymerase such as Taq DNA polymerase is prepared, and used as a reaction solution for PCR. To 20 µl of this reaction solution for PCR, 1 ng of the purified DNA sample is added, and obtained a sample for PCR. This sample for PCR is placed in each well of a 96-well reaction plate, and the real-time PCR is performed using appropriate real-time PCR detection equipment and the like. The reaction is repeated 30 to 50 cycles, and at every cycle, the fluorescence intensity derived from the reporter dye is measured.

In this instance, as for the method for detecting *M. intracellulare*, when the fluorescence derived from the reporter dye is observed, it may be determined that the sample is positive for *M. intracellulare*.

In addition, in the real-time PCR method, as a standard curve can be made up, the number of genomic DNA (copy number) of *M. intracellulare* in the sample can be determined. Further, as the number is proportional to the number of *M. intracellulare* cell, the number of *M. intracellulare* in the sample can also be determined.

The method of preparation of the standard curve may be performed according to the conventional procedure commonly carried out in the real-time PCR method. For example, using a genomic DNA sample of a known copy number derived from *M. intracellulare* as a standard, a dilution series of concentration (copy number) of the DNA sample for PCR is prepared. After that, using each of the dilution series of the DNA sample for PCR, the real-time PCR is performed according to the above described method, and the fluorescence intensity from the reporter dye is measured. For each concentration of the dilution series of the DNA sample for PCR, the measured value of the fluorescence intensity (Rn, y-axis) is plotted for each cycle number of PCR (x-axis) to make up an amplification curve. After that, an Rn part where the fluorescence intensity is amplified exponentially is selected, and a threshold line (Th) is drawn. The crossing point of the Th with an amplification curve of each DNA sample for PCR is defined as threshold cycle (Ct). After that, the Ct value (y-axis) is plotted for the logarithmic value of the copy number of each used DNA sample used for PCR (x-axis), and an approximated curve obtained for each Ct may be used as a standard curve.

By performing the real-time PCR according to the intercalator method, a standard curve can be made by the same way based on the obtained measurement value. For example, an amplification curve is made up by plotting the measurement value of the fluorescence intensity derived form the intercalator (Rn, y-axis) for each cycle number of PCR (x-axis). After that, Ct value is obtained by the same way as described above, and the Ct value (y-axis) is plotted for the logarithmic value of the copy number of each used DNA sample for PCR (x-axis) used in the real-time PCR, and an approximated curve obtained for each Ct may be used as a standard curve.

For the quantitative determination of the number of the genomic DNA (copy number) of *M. intracellulare* in the specimen, at first, the DNA is isolated and purified from the specimen to be detected for *M. intracellulare*, and the real-time PCR of the obtained DNA sample is performed, and an amplification curve is made up in the same manner. The Ct value at the point where the obtained amplification curve crosses the Th obtained when the standard curve is made, is obtained. By fitting the Ct value to the standard curve, the quantity (copy number) of genomic DNA of *M. intracellulare* in the sample can be obtained.

(A-3) A Method in which, after the Nucleic Acid Amplification Reaction is Performed, the Primer Extension Products Obtained are Subjected to Electrophoresis, and the Detection is Performed Based on the Results of the Electrophoresis This method includes, for example, "the method for detecting *M. intracellulare* comprising the following steps of:

(i) performing a nucleic acid amplification reaction using as a primer an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene (the primer of the present invention), and the nucleic acid in a sample as a template; and (ii) performing electrophoresis of the primer extension product obtained in above (i);

and detecting *Mycobacterium intracellulare* based on the obtained result from the electrophoresis.

Method for determination of the presence of *M. intracellulare* based on the obtained results of electrophoresis includes, for example, (A-3-1) a method in which the determination is made by confirming a fraction of the primer extension product having an objective size (number of base pair);

(A-3-2) a method in which the determination is made by hybridization using labeled probe.

Specific examples of the nucleic acid amplification reaction are as described above.

Conditions, operational procedures and the like of the electrophoresis may be in accordance with those of the conventional method usually carried out in this field.

The methods of (A-3-1) and (A-3-2) will be described below.

(A-3-1) The Method in which the Determination is Made by Confirming a Fraction of the Primer Extension Product Having Objective Size (Number of Base Pair)

For example, at first, an appropriate combination of the forward primer and the reverse primer is selected from the primer of the present invention, and with the use of it, the nucleic acid amplification reaction such as PCR is performed by using the combination. And then, the primer extension product obtained is subjected to electrophoresis. From the combination of the forward primer and the reverse primer used for the nucleic acid amplification reaction, a size (number of base pair) of the primer extension product which is anticipated to be amplified by the PCR is estimated in advance. And, confirmation whether the electrophoretic fraction obtained is relevant to the estimated size of amplification product may be made by conventional method. For example, a method in which, by such a way that the type of nucleic acid is visualized by staining the obtained electrophoretic fraction with ethidium bromide and the like, the primer extension product is confirmed based on its characteristic size, is included.

Specific example of the method for determination by the method of (A-3-1) includes, for example, a method in which, after performing the PCR using a combination of the forward primer and the reverse primer listed in the above described Table 1, the primer extension product is subjected to electrophoresis, and when an oligonucleotide having the nucleotide sequence shown in SEQ ID NO described in Table 1, which is anticipated to be amplified by the combination of the primers, or a fraction having a size corresponding to the number of the base pair is confirmed, it may be determined that the sample is positive for *M. intracellulare*.

Among these methods, more preferable method includes, for example, the following methods.

(1) A method in which, after performing the PCR using a combination of an oligonucleotide primer comprising the nucleotide sequence shown in SEQ ID NO: 9 and an oligonucleotide primer comprising the nucleotide sequence shown in SEQ ID NO: 10, the obtained primer extension product is subjected to electrophoresis, and it is determined to be positive if an oligonucleotide fraction having 155 base pair or an oligonucleotide fraction comprising the nucleotide sequence shown in SEQ ID NO: 139 is confirmed.

(2) A method in which, after performing the PCR using a combination of an oligonucleotide primer comprising the nucleotide sequence shown in SEQ ID NO: 23 and an oligonucleotide primer comprising the nucleotide sequence shown in SEQ ID NO: 24, the obtained primer extension product is subjected to electrophoresis, and it is determined to be positive if an oligonucleotide fraction having 159 base pair or an oligonucleotide fraction comprising the nucleotide sequence shown in SEQ ID NO: 146 is confirmed.

(3) A method in which, after performing the PCR using a combination of an oligonucleotide primer comprising the nucleotide sequence shown in SEQ ID NO: 41 and an oligonucleotide primer comprising the nucleotide sequence shown in SEQ ID NO: 42, the obtained primer extension product is subjected to electrophoresis, and it is determined to be positive if an oligonucleotide fraction having 179 base pair or an oligonucleotide fraction comprising the nucleotide sequence shown in SEQ ID NO: 155 is confirmed.

(4) A method in which, after performing the PCR using a combination of an oligonucleotide primer comprising the nucleotide sequence shown in SEQ ID NO: 59 and an oligonucleotide primer comprising the nucleotide sequence shown in SEQ ID NO: 60, the obtained primer extension product is subjected to electrophoresis, and it is determined to be positive if an oligonucleotide fraction having 157 base pair or an oligonucleotide fraction comprising the nucleotide sequence shown in SEQ ID NO: 164 is confirmed.

(5) A method in which, after performing the PCR using a combination of an oligonucleotide primer comprising the nucleotide sequence shown in SEQ ID NO: 79 and an oligonucleotide primer comprising the nucleotide sequence shown in SEQ ID NO: 80, the obtained primer extension product is subjected to electrophoresis, and it is determined to be positive if an oligonucleotide fraction having 160 base pair or an oligonucleotide fraction comprising the nucleotide sequence shown in SEQ ID NO: 174 is confirmed.

(6) A method in which, after performing the PCR using a combination of an oligonucleotide primer comprising the nucleotide sequence shown in SEQ ID NO: 93 and an oligonucleotide primer comprising the nucleotide sequence shown in SEQ ID NO: 94, the obtained primer extension product is subjected to electrophoresis, and it is determined to be positive if an oligonucleotide fraction having 172 base pair or an oligonucleotide fraction comprising the nucleotide sequence shown in SEQ ID NO: 181 is confirmed.

(7) A method in which, after performing the PCR using a combination of an oligonucleotide primer comprising the nucleotide sequence shown in SEQ ID NO: 105 and an oligonucleotide primer comprising the nucleotide sequence shown in SEQ ID NO: 106, the obtained primer extension product is subjected to electrophoresis, and it is determined to be positive if an oligonucleotide fraction having 181 base pair or an oligonucleotide fraction comprising the nucleotide sequence shown in SEQ ID NO: 187 is confirmed.

(8) A method in which, after performing the PCR using a combination of an oligonucleotide primer comprising the nucleotide sequence shown in SEQ ID NO: 127 and an oligonucleotide primer comprising the nucleotide sequence shown in SEQ ID NO: 128, the obtained primer extension product is subjected to electrophoresis, and it is determined to be positive if an oligonucleotide fraction having 152 base pair or an oligonucleotide fraction comprising the nucleotide sequence shown in SEQ ID NO: 198 is confirmed.

(A-3-2) The Method in which the Determination is Made by Hybridization Using Labeled Probe The method includes, for example, a method in which the primer extension product obtained by the nucleic acid amplification reaction is subjected to electrophoresis; the electrophoretic fraction obtained is tested for hybridization with a labeled probe which is prepared by labeling the present invention with a labeling substance; and it is determined that the sample is positive for *M. intracellulare* if presence of a fraction hybridized with the aforementioned labeled probe is confirmed by detecting the signal derived from the aforementioned labeled probe.

Specific examples of the probe to be used and the labeling substance for use in labeling the probe, and the method for labeling the probe are as described above.

An example of the method includes a method as described below, in which, after performing the PCR using a combination of the forward primer and the reverse primer listed in the above described Table 1, the obtained primer extension product is subjected to electrophoresis; an oligonucleotide which is anticipated to be amplified by the combination of the forward primer and the reverse primer used for the PCR and which has a nucleotide sequence comprising a part or an entire sequence of the nucleotide sequence shown in SEQ ID NO in Table 1 is labeled with labeling substance to prepare a labeled probe in advance; the electrophoretic fraction is tested for hybridization with the aforementioned labeled probe, and it is determined that the sample is positive for *M. intracellulare* if presence of a fraction hybridized with the aforementioned labeled probe is confirmed by detecting the signal derived from the aforementioned labeled probe.

The specific examples of the preferable method include, for example, the following methods.

(1) A method in which, after performing the PCR using a combination of an oligonucleotide primer comprising the nucleotide sequence shown in SEQ ID NO: 9 and an oligonucleotide primer comprising the nucleotide sequence shown in SEQ ID NO: 10, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 139 with a labeling substance; and it is determined to be positive if a fraction hybridized with the aforementioned labeled probe is confirmed by detecting the signal derived from the aforementioned labeled probe.

(2) A method in which, after performing the PCR using a combination of an oligonucleotide primer comprising the nucleotide sequence shown in SEQ ID NO: 23 and an oligonucleotide primer comprising the nucleotide sequence shown in SEQ ID NO: 24, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 146 with a labeling substance; and it is determined to be positive if a fraction hybridized with the aforementioned labeled probe is confirmed by detecting the signal derived from the aforementioned labeled probe.

(3) A method in which, after performing the PCR using a combination of an oligonucleotide primer comprising the nucleotide sequence shown in SEQ ID NO: 41 and an oligonucleotide primer comprising the nucleotide sequence shown in SEQ ID NO: 42, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 155 with a labeling substance; and it is determined to be positive if a fraction hybridized with the aforementioned labeled probe is confirmed by detecting the signal derived from the aforementioned labeled probe.

(4) A method in which, after performing the PCR using a combination of an oligonucleotide primer comprising the nucleotide sequence shown in SEQ ID NO: 59 and an oligonucleotide primer comprising the nucleotide sequence shown in SEQ ID NO: 60, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 164 with a labeling substance; and it is determined to be positive if a fraction hybridized with the aforementioned labeled probe is confirmed by detecting the signal derived from the aforementioned labeled probe.

(5) A method in which, after performing the PCR using a combination of an oligonucleotide primer comprising the nucleotide sequence shown in SEQ ID NO: 79 and an oligonucleotide primer comprising the nucleotide sequence shown in SEQ ID NO: 80, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 174 with a labeling substance; and it is determined to be positive if a fraction hybridized with the aforementioned labeled probe is confirmed by detecting the signal derived from the aforementioned labeled probe.

(6) A method in which, after performing the PCR using a combination of an oligonucleotide primer comprising the nucleotide sequence shown in SEQ ID NO: 93 and an oligonucleotide primer comprising the nucleotide sequence shown in SEQ ID NO: 94, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 181 with a labeling substance; and it is determined to be positive if a fraction hybridized with the aforementioned labeled probe is confirmed by detecting the signal derived from the aforementioned labeled probe.

(7) A method in which, after performing the PCR using a combination of an oligonucleotide primer comprising the nucleotide sequence shown in SEQ ID NO: 105 and an oligonucleotide primer comprising the nucleotide sequence shown in SEQ ID NO: 106, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 187 with a labeling substance; and it is determined to be positive if a fraction hybridized with the aforementioned labeled probe is confirmed by detecting the signal derived from the aforementioned labeled probe.

(8) A method in which, after performing the PCR using a combination of an oligonucleotide primer comprising the nucleotide sequence shown in SEQ ID NO: 127 and an oligonucleotide primer comprising the nucleotide sequence shown in SEQ ID NO: 128, the obtained primer extension product is subjected to electrophoresis; and then an electrophoretic fraction obtained is tested for hybridization with a labeled probe prepared by labeling an oligonucleotide which comprises a part or an entire sequence of the nucleotide sequence shown in SEQ ID NO: 198 with a labeling substance; and it is determined to be positive if a fraction hybridized with the aforementioned labeled probe is confirmed by detecting the signal derived from the aforementioned labeled probe.

The details of the method for detecting *M. intracellulare* of the present invention by the method of (A-3) will be explained, for example, by taking a case as an example where, after the PCR is performed using 02_Fw1 as a forward primer and 02_Rv1 as a reverse primer and followed by electrophoresis, the detection is performed by the method of confirming a fraction of the primer extension product having the objective number of base pair (the method of above (1) of (A-3-1)), as follows.

First, according to a known method (for example, the above described method), a purified DNA sample is obtained from the sample to be detected for the presence of *M. intracellulare*. Separately, according to the above described method, and using a DNA synthesizer, 02_Fw1 (an oligonucleotide having a nucleotide sequence shown in SEQ ID NO: 9) and 02_Rv1 (an oligonucleotide having a nucleotide sequence shown in SEQ ID NO: 10) are synthesized by the phosphoramidite method.

A 10 mM Tris-HCl buffer solution (pH 8.9) containing each 0.1 to 2 µM, preferably each 1 µM of the primer 02_Fw1 and the primer 02_Rv1, 1.0 to 4.0 mM $MgCl_2$, KCl, BSA, sodium cholate, 0.005 to 0.2% polyoxyethyleneoctylphenyl ether, each about 0.1 to 0.6 mM of dATP, dCTP, dGTP and dTTP, and 10 to 80 unit/ml of Taq DNA polymerase is prepared, and used as reaction solution for PCR.

The purified DNA is added to the reaction solution for PCR, and using this solution as a sample for PCR, 20 to 40 cycles of the PCR is performed by the DNA Thermal Cycler. The obtained reaction solution after PCR is subjected to 1.5% agarose gel electrophoresis. Subsequently, after staining the gel with ethidium bromide, the fluorescence generated by UV ray irradiation is detected. Also, the molecular weight marker is electrophoresed in the same time in parallel with the reaction solution, and a length of the detected DNA fragment is calculated by comparing the relative mobility. In the PCR using the 02_Fw1 as a forward primer and the 02_Rv1 as a reverse primer, it is anticipated that the DNA fragment with 155 base pair (having a nucleotide sequence shown in SEQ ID NO: 193) in the nucleotide sequence of *M. intracellulare* could be replicated. Consequently, if a fluorescent band with the size of 155 base pair is confirmed, it may be determined that the sample is positive for *M. intracellulare*.

In addition, in the nucleic acid amplification step of the present invention, a detection method through the use of RNA transcription product can be applied. For example, NASBA (nucleic acid sequence based amplification) method (JP-2650159), 3SR (self-sustained sequence replication) method (JP-B-1995-114718), TAS (transcription based amplification system) method (JP-A-1990-500565: WO 88/10315), TMA (transcription mediated amplification) method (JP-A-1999-46778) and the like are included. Among them, the constant temperature nucleic acid amplification methods utilizing a concerted mode of action of reverse transcriptase and RNA polymerase (reaction is performed under such condition that allows the reverse transcriptase and the RNA polymerase act as concertedly) is suitable for the automation of the determination system.

(A-4) The Method in which the Determination is Carried Out by Measuring the Signal Derived from the Primer Extension Product Obtained by the Nucleic Acid Amplification Reaction Using the Labeled Primer The method is included, in which, using a labeled primer which is the primer of the present invention labeled according to the above described method, the nucleic acid amplification reaction such as PCR is performed with the nucleic acid in the sample as a template, and the detection/measurement of the signal derived from the obtained primer extension product is carried out, and when the sign is detected, it is determined that the sample is positive for *M. intracellulare*. The forward primer and the reverse primer to be used in this method include the ones which are used in the above described PCR method, and the specific examples of preferable primers and preferable combination are also as described above.

In the case of the above described method, after the nucleic acid amplification reaction is performed, free labeled primer is removed; and the signal derived from the primer extension product is measured; and it may be determined that the sample is positive for *M. intracellulare* if the signal is detected.

Method for removing free labeled primer includes a method in which, after the primer extension product in the reaction mixture obtained by the nucleic acid amplification reaction is precipitated by the conventional procedure of precipitating nucleic acid (ethanol precipitation method, a precipitation method using isopropanol and the like), the supernatant solution which contains non-precipitated free labeled primer is removed, and the like.

In addition, a method for separating the primer extension product from free labeled primer by processing the reaction mixture obtained by the nucleic acid amplification reaction by gel chromatography under appropriate conditions, and a method of separation by electrophoresis under appropriate conditions are also included.

(B) A Method in which the Oligonucleotide of the Present Invention is Labeled with a Labeling Substance, and is Used as a Labeled Probe.

Further, the method for detecting *M. intracellulare* of the present invention includes a method in which, an oligonucleotide which comprises a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene (the oligonucleotide of the present invention) is labeled with a labeling substance and used as a labeled probe, the aforementioned labeled probe is allowed to hybridize with the nucleic acid in the sample, and after removing the free labeled probe, the signal derived from the hybridized complex is detected.

Specifically, the following methods are included:

(B-1) A detection method in which, the oligonucleotide of the present invention is bound to the solid carrier and used as a trapping probe, and is allowed to hybridize with nucleic acid in the sample, and thereby the nucleic acid derived from *M. intracellulare* is immobilized on the solid phase (see, for example, the description in JP-A-1987-265999). In this case, the oligonucleotide of the present invention or the solid carrier may be labeled with a labeling substance.

(B-2) A method of so called "sandwich assay" in which an unlabeled trapping probe of (B-1) and the labeled probe which is the labeled probe of the present invention, are allowed to hybridize with nucleic acid in the sample to form a complex of trapping probe and nucleic acid derived from *M. intracellulare* and labeled probe on the solid carrier, then the signal derived from the labeled probe is measured (see, for example, the description in JP-A-1989-40099).

(B-3) A method in which, using a biotin-labeled probe of the present invention, the hybridization with nucleic acid in the sample is carried out, and after that, the nucleic acid derived from *M. intracellulare* in the sample is trapped by the avidin-bound carrier.

It should be noted that, as to the reagents to be used for the method for detecting *M. intracellulare* of the present invention, the reagent usually used in this field which neither inhibit the stability of the coexisting reagents nor inhibit the nucleic acid amplification reaction such as PCR and hybridization reaction, for example, buffering agent, stabilizer, preservatives and the like can be used. And, concentration of the reagent may be selected as appropriate from the range of concentration usually used in this field.

The specific example of buffer solution includes all of the buffer solutions usually used for performing PCR and hybridization reaction, for example, Tris buffer, phosphate buffer, veronal buffer, borate buffer, Good's buffer and the like; and the pH of the buffer solution is not particularly limited, but generally a range between pH 5 to 9 is preferable.

In addition, if necessary, nucleic acid synthetase (DNA polymerase, RNA polymerase, reverse transcriptase and the like), substrate corresponding to the enzyme (dNTP, rNTP and the like), and additionally, double strand intercalator (ethidium bromide, SYBR™ Green and the like), and alternatively, the signal detection substance such as FAM and TAMRA may be used.

The reagent kit for detecting *M. intracellulare* of the present invention includes "A reagent kit for detecting *Mycobacterium intracellulare*, comprising an oligonucleotide comprising a part or the entire sequence of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, or a part or the entire sequence of a sequence complementary to the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, wherein the oligonucleotide is capable of hybridizing with a nucleotide sequence of *Mycobacterium intracellulare* gene as a primer (the primer of the present invention) and/or a probe (the probe of the present invention)". The primer may be the one which is labeled with a labeling substance. The specific example of the labeling substance is as described above.

Specific examples of the primer of the present invention and the probe of the present invention which constitute the above described kit are as described hereinbefore in the explanation for the "the primer of the present invention" and "the probe of the present invention".

The primer of the present invention may be the one which is labeled with a labeling substance. Specific example of the labeling substance is as described above.

The kit comprising the primer of the present invention also encompasses a composition comprising a pair of the forward primer and the reverse primer. A preferable embodiment of the kit includes the composition comprising a combination of the forward primer and the reverse primer listed in the above described Table 1.

For example, the following compositions may be included.

(1) A kit comprising (a) an oligonucleotide primer which comprises a part or the entire sequence of the nucleotide sequence shown in SEQ ID NO: 9, or a part or the entire sequence of the sequence complementary to the nucleotide sequence shown in SEQ ID NO: 9, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 10, or a part or the entire sequence of the sequence complementary to the nucleotide sequence shown in SEQ ID NO: 10, wherein the oligonucleotide is capable of hybridizing with a nucleotide sequence of *M. intracellulare* gene, as the constituent reagents.

(2) A kit comprising (a) an oligonucleotide primer which comprises a part or the entire sequence of the nucleotide sequence shown in SEQ ID NO: 23, or a part or the entire sequence of the sequence complementary to the nucleotide sequence shown in SEQ ID NO: 23, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 24, or a part or the entire sequence of the sequence complementary to the nucleotide sequence shown in SEQ ID NO: 24, wherein the oligonucleotide is capable of hybridizing with a nucleotide sequence of *M. intracellulare* gene, as the constituent reagents.

(3) A kit comprising (a) an oligonucleotide primer which comprises a part or the entire sequence of the nucleotide sequence shown in SEQ ID NO: 41, or apart or the entire sequence of the sequence complementary to the nucleotide sequence shown in SEQ ID NO: 41, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 42, or a part or the entire sequence of the sequence complementary to the nucleotide sequence shown in SEQ ID NO: 42, wherein the oligonucleotide is capable of hybridizing with a nucleotide sequence of *M. intracellulare* gene, as the constituent reagents.

(4) A kit comprising (a) an oligonucleotide primer which comprises a part or the entire sequence of the nucleotide sequence shown in SEQ ID NO: 59, or a part or the entire sequence of the sequence complementary to the nucleotide sequence shown in SEQ ID NO: 59, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 60, or a part or the entire sequence of the sequence complementary to the nucleotide sequence shown in SEQ ID NO: 60, wherein the oligonucleotide is capable of hybridizing with a nucleotide sequence of *M. intracellulare* gene, as the constituent reagents.

(5) A kit comprising (a) an oligonucleotide primer which comprises a part or the entire sequence of the nucleotide sequence shown in SEQ ID NO: 79, or a part or the entire sequence of the sequence complementary to the nucleotide sequence shown in SEQ ID NO: 79, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 80, or a part or the entire sequence of the sequence complementary to the nucleotide sequence shown in SEQ ID NO: 80, wherein the oligonucleotide is capable of hybridizing with a nucleotide sequence of *M. intracellulare* gene, as the constituent reagents.

(6) A kit comprising (a) an oligonucleotide primer which comprises a part or the entire sequence of the nucleotide sequence shown in SEQ ID NO: 93, or a part or the entire sequence of the sequence complementary to the nucleotide sequence shown in SEQ ID NO: 93, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 94, or a part or the entire sequence of the sequence complementary to the nucleotide sequence shown in SEQ ID NO: 94, wherein the oligonucleotide is capable of hybridizing with a nucleotide sequence of *M. intracellulare* gene, as the constituent reagents.

(7) A kit comprising (a) an oligonucleotide primer which comprises a part or the entire sequence of the nucleotide sequence shown in SEQ ID NO: 105, or a part or the entire sequence of the sequence complementary to the nucleotide sequence shown in SEQ ID NO: 105, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 106, or a part or the entire sequence of the sequence complementary to the nucleotide sequence shown in SEQ ID NO: 106, wherein the oligonucleotide is capable of hybridizing with a nucleotide sequence of *M. intracellulare* gene, as the constituent reagents.

(8) A kit comprising (a) an oligonucleotide primer which comprises a part or the entire sequence of the nucleotide sequence shown in SEQ ID NO: 127, or a part or the entire sequence of the sequence complementary to the nucleotide sequence shown in SEQ ID NO: 127, wherein the oligonucleotide is capable of hybridizing with a nucleotide sequence of *M. intracellulare* gene, and (b) an oligonucleotide which comprises a part or the entire sequence of the nucleotide sequence shown in SEQ ID NO: 128, or a part or the entire sequence of the sequence complementary to the nucleotide sequence shown in SEQ ID NO: 128, wherein the oligonucleotide is capable of hybridizing with a nucleotide sequence of *M. intracellulare* gene, as the constituent reagents.

In the above described kits, further, the oligonucleotide of the present invention which is labeled with a labeling substance may be contained as a labeled probe.

Further, "a reagent kit for detecting *M. intracellulare*, comprising the oligonucleotide of the present invention as a probe" is included. The aforementioned probe may be the one labeled with a labeling substance.

The preferable embodiment and specific examples of the constituent reagents composing these kits are as described above.

It should be noted that, the reagent kit for detecting *M. intracellulare* of the present invention may comprise, for example, buffering agent, stabilizer, preservatives and the like which neither inhibit the stability of the coexisting reagents and the like nor inhibit the nucleic acid amplification reaction such as PCR and the hybridization reaction. In addition, the concentrations of the reagents may be selected as appropriate from the range of concentration usually used in this field.

Specific example of buffer solution includes all of the buffer solutions usually used for performing the PCR and the hybridization reaction, for example, Tris buffer, phosphate buffer, veronal buffer, borate buffer, Good's buffer and the like, and the pH is not particularly limited, but generally a range between pH 5 to 9 is preferable.

In addition, if necessary, the nucleic acid synthetase (DNA polymerase, RNA polymerase, reverse transcriptase and the like), the substrate corresponding to the enzyme (dNTP, rNTP and the like), and additionally, the double strand intercalator (ethidium bromide, SYBR™ Green and the like), and alternatively, the signal detection substance such as FAM and TAMRA, may be contained in the kit.

Hereinafter, the present invention will be further explained in detail by referring to the following Examples, but the scope of the present invention should not be limited thereto.

It should be noted that all bacteria used in Examples are clinical isolates, and their bacterial species has already been differentiated by the colony morphology and the conventional various biochemical tests on the cultured bacterium.

EXAMPLE

Experimental Example 1

Selection of Clone Derived from *M. intracellulare* Genome (1) Preparation of DNA Sample First, colonies of *M. intracellulare* (ATCC13950) cultured on the Ogawa's medium are collected and suspended in purified water, and after autoclaving (at 120° C., 2 atmospheres for 20 minutes), by way of disruption treatment (physical disruption using 2 mm diameter of glass beads) followed by centrifugation, a supernatant solution was obtained. From the supernatant solution obtained, extraction and purification of DNA was carried out using an ion exchange resin type DNA extraction and purification kit, Genomic-tip, manufactured by QIAGEN GmbH.

The purified genomic DNA fragments obtained was adjusted to give final concentration of 400 ng/μl (in 10 mM Tris-HCl buffer, pH 8.9), and used as DNA sample derived from *M. intracellulare*.

In addition, using rps1 (a DNA fragment having a sequence shown in SEQ ID NO. 205, a specific sequence for a *M. intracellulare*, described in Patent Literature 1), IS6110 element (a DNA fragment having a sequence shown in SEQ ID NO: 206, a specific sequence of *Mycobacterium bovis* (bovine tubercle *bacillus*)), and KATS2 sequence of *M. kansasii* (a DNA fragment having a sequence shown in SEQ ID NO: 207, a specific sequence for *M. kansasii*, described in JP-A-1990-155589) as positive control, and using MAV19K of *M. avium* (a DNA fragment having a sequence shown in SEQ ID NO: 208, a specific sequence for a *M. avium*, described in JP-A-11-06999) and the DNA derived from *E. coli* prepared according to the conventional procedure of extraction and purification of *E. coli* DNA as negative control, each DNA sample was prepared in the same manner, and subjected to the following treatment in the same way.

(2) Preparation of Whole Genome Shotgun Library

Using a 24 μg of the DNA sample derived from *M. intracellulare* obtained in (1) above as a material, the Whole Genome Shotgun library was prepared by the following method (a modified method from the Whole Genome Shotgun method described in Science 2001 Feb. 16; 291 (5507): 1304-1351 Venter et al).

First, the DNA sample derived from *M. intracellulare* was treated using a nebulizer (manufactured by Invitrogen) in the presence of 20% Final concentration of glycerol under the pressure of 5 kPa to 9 kPa for about 10 minutes to fragmentate the DNA. By this treatment method, a fraction with the objective size of 500 to 1,000 base pair was recovered efficiently. The fraction obtained was purified using an extraction column manufactured by QIAGEN GmbH.

In the next place, using the DNA Blunting Kit manufactured by Takara Bio Inc. and through the use of 5'→3' polymerase activity and 3'→5' exonuclease activity of T4 DNA Polymerase, the terminal of obtained DNA fragment was blunted. This blunt-ended DNA fragment was subjected to ligation reaction with blunt-ended pBSII sk⁺ vector (Stratagene Corp.), and a recombinant DNA of pBSII sk+ vector (amp$^r$), in which the DNA fragment was inserted thereto, was prepared.

Using *E. coli* JM109 Competent Cells manufactured by Takara Bio Inc., transformation of the *E. coli* JM109 Competent Cells was carried out using the recombinant DNA obtained above according to a protocol of the product. The transformant obtained above was cultured in a plate on LB-agarose medium containing 100 μg/ml ampicillin, 0.2 mM IPTG and 40 μg/ml X-Gal. The white colonies were picked up, and thus a library of the transformant (Whole Genome Shotgun clone library derived from *M. intracellulare* genome) which was introduced by transduction with the recombinant DNA in which the objective DNA fragment has been inserted therein was obtained.

(3) Preparation of Microarray

Using the library of the transformant obtained in (2) above (Whole Genome Shotgun clone library derived from *M. intracellulare* genome), the PCR was performed for preparing a probe material to be fixed on a slide glass by the following method.

Firstly, a 10 mM Tris-HCl buffer solution (pH 8.9) containing 1 μM each of M13 Primer M1 (Takara Bio Inc.) and M13 Primer RV (Takara Bio Inc.), 1.5 MgCl$_2$, 80 mM KCl, 500 μg/ml BSA, 0.1% sodium cholate, 0.11% Triton X-100 (product name of polyoxyethylene octylphenyl ether, Rohm and Haas Co.), 0.2 nM each of dATP, dCTP, dGTP and dTTP, and 40 unit/ml of Taq DNA polymerase (Nippon Gene Co.) was prepared and used as a reaction solution for PCR.

The DNA was purified from each transformant (Whole Genome Shotgun clone of *M. intracellulare* genome) obtained in (2) above according to the conventional procedure. This purified DNA (which would be used as a template) was added to 20 μl of the reaction solution and suspended, and the suspension prepared was used as a sample for PCR. Using this sample for PCR, 30 cycles of PCR was performed under the following reaction conditions using the DNA Thermal Cycler (DNA Engine PTC200, MJ Research Inc.).

Reaction conditions of the PCR:
Heat denaturation: 94° C. for 0.5 minutes;
Annealing: 55° C. for 1 minute;
Polymerization reaction: 75° C. for 0.5 minutes.

The obtained PCR amplification product was purified, and then mixed with immobilization buffer (final concentration: 3×SSC).

The final concentration of the PCR product to be spotted was adjusted to give 300 ng/μl, and using a typing instrument (GTMAS Stamp II; Nippon Laser & Electronics) which was set at 55% in humidity in the instrument, the PCR amplification product obtained above was spotted (the spot diameter: 150 to 250 μm) on a slide glass (CMT GAPS-II; Corning Inc.). The spotting-completed slide glass was transferred to a UV cross-linker (UV Stratalinker 1800; Stratagene Corp.), and was irradiated with 150 mJ/cm$^2$ of UV light to fix the PCR amplification product (the objective DNA) on the slide glass, and thus the microarray (a microarray made from the Whole Genome Shotgun clone library of DNA derived from *M. intracellulare* genome as a material, 1,100 clones in total) was prepared.

As to the DNA sample for positive control (rps1, IS6110 element and KAT S2 sequence) and the DNA sample for negative control (MAV19K and DNA derived from *E. coli*) as obtained in (1) above, the preparation of Whole Genome Shotgun library as described in (2) above and the preparation of the microarray as described in (3) above were also carried out in the same way, and each microarray for each DNA sample was prepared on a slide glass.

(4) Fluorescent Labeling of the Target Genomic DNA and Microarray Hybridization i) Fluorescent Labeling of the Target Genomic DNA Fluorescent labeling of the target genomic DNA was carried out using BioPrime DNA labeling system (Invitrogen Co.).

Firstly, after a 2 μg of genomic DNA extracted and purified from *M. intracellulare* (ATCC 16950) by conventional procedure were mixed with 20 μl of random primer solution contained in the product, the mixture was subjected to heat denaturation treatment (95° C. for 5 minutes), and thereby, the sample solution was obtained. Separately, the genomic DNA of each *Mycobacterium bovis* (bovine type tuberculosis bacterium, granted by Japanese Society for Bacteriology) and *M. kansasii* (ATCC12478) was extracted and purified by conventional procedure (comparative genomic DNA), and the same treatment was also carried out for each DNA sample, sample solutions were obtained.

Subsequently, to each sample solution obtained, 2 μl of 0.1 M DTT, 2 μl of the mixed solution of dATP/dCTP/dGTP (each 5 mM), 0.8 μl of 2.5 mM dTTP, 1.6 μl of 5 mM Ha-dUTP and 1 μl of Klenow enzyme (40 U/μl) were added and adjusted to give the total volume 50 μl with sterile deionized water, and then the extension reaction was performed at 37° C. for 3 hours. An ultrafiltration column Microcon YM-30 (Millipore Co.) was set to the attached 1.5 ml tube, and then above obtained reaction product was placed on the column and centrifuged at 14,000 rpm for 4 minutes. The concentrated solution was recovered in a microtube, and then dried thoroughly using a centrifugal vacuum drier (CentriVap concentrator; LABCONCO Co.).

The dried reaction product obtained above was added with 10 μl of 50 mM NaHCO$_3$ and mixed, then left for standing at ambient temperature for 2 to 3 minutes (hereinafter referred to as "solution of reaction product").

Separately, 1 mg of Cy3 (Amersham Biosciences) or Cy5 (Amersham Biosciences) was dissolved in 105 μl of DMSO (Cy-dye Solution Cy3, Cy-dye Solution Cy5). A 10 μl of the Cy-dye Solution Cy3 was added to each sample solution which was obtained with the use of comparative genomic DNA fragment (derived from *M. bovis, M. kansasii*), and incubated (under light shielding) at 40° C. for 60 minutes. In addition, a 10 μl of the Cy-dye Solution Cy5 was added to the above described sample solution which was obtained with the use of genomic DNA fragment derived from *M. intracellulare*, and incubated (under light shielding) at 40° C. for 60 minutes.

Further, to the above described each reaction product of post incubation, a 10 μl of 4 M NH$_2$OH (prepared just before use) was added and mixed, and was incubated (under light shielding) for 15 minutes to obtain the respective labeled product, namely, the labeled product of the Cy3-labeled comparative genomic DNA derived from *M. bovis*, the labeled product of the Cy3-labeled comparative genomic DNA derived from *M. kansasii* and the labeled product of the Cy5-labeled genomic DNA derived from *M. intracellulare*, were obtained.

An ultrafiltration column, Microcon YM-30 (Millipore Co.), was set to the attached 1.5 ml tube, and then each of the above obtained labeled products of genomic DNA was placed on the column and centrifuged at 14,000 rpm for 4 minutes. The each concentrated solution was recovered in a microtube and dried thoroughly using a centrifugal vacuum drier (CentriVap concentrator; LABCONCO Co.).

ii) Fragmentation Process for The Labeled Products

To the labeled product from genomic DNA in dry state obtained in i) of (4) above, a 40 μl of a solution with a composition of the final concentrations of 0.04 M Tris-acetate (pH 8.1), 0.1 M potassium acetate, and 0.03 M magnesium acetate tetrahydrate were added and mixed in suspension. After that, the suspensions was heat-treated at 94° C. for 15 minutes, and the fragmentation products of each labeled genomic DNA with 100 to 300 nucleotides were obtained.

It should be noted that, the labeling efficiency (nucleotide/dye) was checked using BcaBEST DNA Polymerase (Takara Bio Inc.) and rBst DNA Polymerase (EPICENTRE Biotechnologies), and confirmed that, in the results of Cy3 labeling experiment, one molecule of dye was incorporated into about 20 nucleotides of both the comparative genomic DNA derived from *M. bovis* and the genomic DNA derived from *M. kansasii*, and in the results of Cy5 labeling experiment, one molecule of dye was incorporated into about 10 nucleotides of the *M. intracellulare* genomic DNA.

The resultant solutions of Cy3-labeled product and Cy5-labeled product were mixed and placed onto an ultrafiltration column, and then centrifuged at 14,000 rpm for 4 minutes. After that, the concentrated solution was recovered in a microtube, and then dried thoroughly using a centrifugal vacuum drier (CentriVap concentrator; LABCONCO Co.). Subsequently, the following reagents were added to the microtube and dissolved the labeled products by mixing in suspension, and thus, a mixed solution of Cy3Cy5-labeled products comprising the Cy3-labeled product of the comparative genomic DNA for the derived from *M. bovis* and the Cy5-labeled product of the genomic DNA derived from *M. intracellulare*, and a mixed solution of Cy3Cy5-labeled products comprising the Cy3-labeled product of the comparative genomic DNA derived from *M. kansasii* and the Cy5-labeled product of the genomic DNA derived from *M. intracellulare*, were obtained.

ArrayHyb Hybridization buffer (SIGMA-Aldrich Co.); 40 µl
Salmon sperm DNA (10 mg/ml); 0.5 µl
Formamide; 5 µl
Total 40 to 50 µl The obtained mixed solutions of Cy3Cy5-labeled products were incubated at 95° C. for 5 minutes, and kept at 70° C. until use for hybridization.

iii) Microarray Hybridization

By the step of the above described (3), a microarray (DNA chip) in which each spot of the Whole Genome Shotgun clone of *M. intracellulare* and the DNA fragments for use in positive control and negative control were integrated on the same slide glass was prepared.

The mixed solutions of Cy3Cy5-labeled products obtained in the above described ii) of (4) were each placed on the microarray, and covered with a cover glass keeping no air bubble remained inside. The microarray was set on a Hybri-cassette and placed on Kim Towel mat wetted with distilled water in a Tupperware and closed tightly, and was kept (under light shielding) at 65° C. for 8 hours or more to allow hybridization. After hybridization, the DNA chip was soaked in a solution of 2×SSC containing 0.1% SDS together with cover glass at room temperature, and shook gently the DNA chip in the solution to remove the cover glass. Subsequently, after sequential washing with 1×SSC solution containing 0.03% SDS (at 60° C.) for 10 minutes, 0.2×SSC solution (at 42° C.) for 10 minutes and 0.05×SSC solution (at room temperature) for 10 minutes, the DNA chip was transferred quickly to a new dry rack, and dried immediately by centrifugation at 800 rpm for 5 minutes.

(5) Measurement of Fluorescence Intensity: from Signal Detection to Quantification Using a fluorescence detection scanner (Protein Array Scanner; Nippon Laser & Electronics), the fluorescence intensity on the microarray (DNA chip) which received the microarray-hybridization treatment was measured. On this occasion, in order to analyze the results of competitive hybridization by using Cy3-labeled product and Cy5-labeled product, 2 channel data, namely 2ch (Cy3, Cy5) fluorescence detection data were obtained.

The quantification of fluorescence signal was performed using the DNASIS™-Array (DNA chip expression image analysis software; Hitachi Software Engineering Co.), and according to the operational procedure of the software, automatic spot recognition, background calculation, and normalization of the fluorescence intensity ratio were carried out. In addition, by establishing a threshold limit line of reliability, and avoiding the value lower than this line, a reliable normalized fluorescence intensity ratio was obtained.

On the microarray chip, the DNA derived from the microbial cell of *M. intracellulare*, the positive control (rps1: a DNA fragment having a specific sequence for a *M. intracellulare*, IS6110 element: a DNA fragment having a specific sequence for a *Mycobacterium bovis*, and KATS2 sequence: a DNA fragment having a specific sequence for a *M. Kansasii*) and the negative control (MAV19K: a DNA fragment having a specific sequence for a *M. avium*, and the genomic DNA fragment derived from *E. coli*) have been spotted.

Firstly, using a mixture of the Cy3-labeled product of comparative DNA derived from *M. bovis* and the Cy5-labeled product of genomic DNA derived from *M. intracellulare*, the microarray hybridization was carried out, and the fluorescence intensity was measured to obtain the fluorescence intensity ratio of Cy3/Cy5 (Ratio). That is, when the fluorescence intensity ratio of Cy5 to Cy3 for a certain spot on the microarray is high, it indicates that the DNA fragment (PCR amplification product) of the spot has been hybridized more strongly with the Cy5-labeled product, namely with the genomic DNA derived from *M. intracellulare*. On the other hand, when the fluorescence intensity ratio of Cy5 to Cy3 for a certain spot on the microarray is low, it indicates that the DNA fragment of the spot has low specificity for the genomic DNA derived from *M. intracellulare*, but hybridized more strongly with the Cy3-labeled product, namely with the comparative genomic DNA derived from *M. bovis*. By this method, the fluorescence intensity ratio for the entire spots of the microarray was calculated, and the top 50 spots having high fluorescence intensities and having high fluorescence intensity ratios of Cy5 to Cy3 were selected.

For the same microarray, using a mixture of the Cy3-labeled product of comparative genomic DNA derived from *M. kansasii* and the Cy5-labeled product of genomic DNA derived from *M. intracellulare*, the micro array hybridization, measurement of the fluorescence intensity and measurement of the fluorescence intensity ratio were carried out in the same way as described above. In this case, when the fluorescence intensity ratio of Cy5 to Cy3 for a certain spot is high, it indicate that the DNA fragment (PCR amplification product) of the spot has been hybridized more strongly with the Cy5-labeled product, namely with the genomic DNA derived from *M. intracellulare*. On the other hand, when the fluorescence intensity ratio of Cy5 to Cy3 for a certain spot is low, it indicate that the DNA fragment of the spot has low specificity for the genomic DNA derived from *M. intracellulare*, but hybridized more strongly with the Cy3-labeled product, namely with the comparative genomic DNA derived from *M. kansasii*. The fluorescence intensity ratios for all spots of the microarray were calculated, and the top 50 spots having high fluorescence intensities, and having high fluorescence intensity ratios of Cy5 to Cy3 were selected.

By way of comparing the top 50 spots selected when the Cy3-labeled product of genomic DNA derived from *M. bovis* was utilized as a comparative one and the top 50 spots selected when the Cy3-labeled product of genomic DNA derived from *M. kansasii* was utilized as a comparative one, from the common spots in both cases, 16 spots detected much stronger fluorescence of Cy5 than the fluorescence from the spot of rps1 (a sequence specific for *M. intracellulare*) were selected. These spots were judged to have higher specificity for *M. intracellulare*, than for *M. bovis*, than for *M. kansasii*, and further than for rps1. Thus, these 16 clones were selected as the primitive candidates.

(6) Determination of Nucleotide Sequence of the Primitive Candidate Clones

For the selected 16 primitive candidate clones, their nucleotide sequences were determined by the method described below.

Namely, using Big Dye Terminator kit (Applied Biosystems), sequence analysis was carried out by the following procedure according to the protocol of the product.

Primitive candidate DNA (the primitive candidate clone); 2 μl (100 ng)

M13 Primer M1; 1 μl (5 pmol)

Premix; 8 μl

To the above mixture, sterile deionized water was added to give a total volume of 20 μl, and then 30 cycles of the sequencing reaction under the following reaction conditions were performed using the DNA Thermal Cycler (DNA Engine PTC200, MJ Research Inc.).

96° C. for 2 min→(96° C. for 10 sec→50° C. for 5 sec→60° C. for 4 min)×25→4° C.

The resultant sequencing reaction product obtained was purified using a gel filtration column (QIAGEN GmbH), and then, using a sequencer (BaseStation, MJ Research Inc.), sequence (nucleotide sequence) mapping for all of the candidate sequences was carried out according to the operation manual attached to the instrument.

The data obtained were searched from the data base (NCBI BLAST and CHEMICAL ABSTRACT), and it was found that all of the 16 primitive candidate clones were unregistered new sequence on the data base. This may supposedly be attributed to the fact that the genome sequencing of *M. intracellulare* is not completed yet.

(7) Selection of the Final Candidate Clone

1) Synthesis of the Primer for PCR

Firstly, based on the results of the sequence analysis for the determined 16 primitive candidate clones, the primer sequence for use in the PCR amplification detection was designed for each primitive candidate clone by using a primer design tool on the web, Primer 3 (whitehead Institute for Biomedical Research); and further, based on the results, a combination of the forward primer and the reverse primer which was supposed to be available for the PCR was designed.

The designed oligonucleotide was synthesized by the phosphoamidite method using ABI 392 DNA Synthesizer. The synthetic procedure was carried out according to a manual supplied by ABI, and deprotection of various types of oligonucleotides was performed by heating the aqueous ammonia solution of the oligonucleotide at 55° C. for over night.

Subsequently, the synthesized oligonucleotide was purified by anion exchange column chromatography using Pharmacia FPLC.

2) Preparation of Probe

From the nucleotide sequence anticipated to be amplified by the PCR with the use of a combination of forward primer and reverse primer designed for each primitive candidate clone, the sequence to be used as a probe was designed, and an oligonucleotide having this sequence was synthesized. The 5'-terminal of this oligonucleotide was labeled with a reporter dye of FAM and the 3'-terminal thereof was labeled with a reporter quencher of TAMRA, and thus the labeled oligonucleotide probe (TaqMan™ fluorescent probe, Applied Biosystems Japan) was obtained.

3) Preparation of DNA Sample for PCR

Separately, from *M. intracellulare*, the genomic DNA sample was prepared according to the conventional method. In addition, as a reference (comparison), DNA samples (for reference, for comparison) were prepared from *Escherichia coli* and 18 species of *Mycobacterium* genus (*M. tuberculosis, M. kansasii, M. marinum, M. simiae, M. scrofulaceum, M. gordonae, M. szulgai, M, avium, M. gastri, M. xenopi, M. nonchromogenicum, M. terrae, M. triviale, M. fortuitum, M. chelonei, M. abscessus, M. peregrinum*) according to the conventional method. For the obtained DNA samples, quantity of DNA in each sample was determined by measuring absorbance. Quantity of genomic DNA (genome copy number) in the sample was determined by comparing the obtained quantity of DNA with the known quantity of genomic DNA of individual microbial cell. A $10^8$ copy/μl of genomic DNA was obtained.

After that, the DNA sample was diluted using 10 mM Tris-HCl buffer, pH 8.9 to a dilution series of $10^5$, $10^4$, $10^3$, $10^2$, 10, 5 and 2 copy/μl, and used as DNA samples for PCR.

4) Real-time PCR

Using the forward primer and the reverse primer prepared in the above 1), real-time PCR was performed as follows.

Namely, a 10 mM Tris-HCl buffer solution (pH 8.9) containing 1 μM each of the forward primer and the reverse primer designed from one of the primitive candidate clones, 195 nM of the fluorescence labeled probe prepared in the above (2), 1.5 mM $MgCl_2$, 80 mM KCl, 500 μg/ml BSA, 0.1% sodium cholate, 0.1% Triton X-100, 0.2 mM each of dATP, dCTP, dGTP and dTTP, and 40 unit/ml of Taq DNA polymerase (Nippon Gene Co.) was prepared and used as a reaction solution.

To 20 μl of the reaction solution, 1 ng of each dilution series of DNA sample was added and used as a sample for PCR. This sample for PCR was placed in each well of a 96-well reaction plate (MicroAmp Optical 96-well Reaction Plate; Applied Biosystems Japan Ltd.), and the real-time PCR was performed using a specialized thermal cycler/detector for the TaqMan™ PCR (ABI 7500, Applied Biosystems Japan Ltd.). After keeping the temperature at 95° C. for 10 minutes, the reaction was repeated 50 cycles of a reaction cycle composed of heating at 95° C. for 15 seconds and 60° C. for 1 minute, and in every cycle, fluorescence intensity of the reporter dye was measured. It should be noted that, fluorescence intensity was measured by using a function of the thermal cycler used for the measurement to calculate relative fluorescent intensity ratio, for each of the 96 well reaction plates used for the measurement.

It should be noted that, for every one of the primitive candidate clone, using the forward primer and the reverse primer each of which was designed based on the nucleotide sequence, and using the DNA samples derived from *M. intracellulare,* 18 types of DNA samples derived from microbial cell of *Mycobacterium* genus and the DNA sample from *E. Coli* as a template, the real-time PCR was performed in a 96-well reaction plate at a time.

5) Secondary Screening

From the results of the real-time PCR obtained in the above described 4), the combination of the primers which provided the amplification product in the real-time PCR when the genomic DNA derived from *M. intracellulare* was used as a template, and which did not provide any amplification product when the genomic DNA (for comparison) derived from other microbial cell was used as a template, was selected. And, the candidate clone which was involved in designing such combination of primers was selected finally as a specific candidate clone for *M. intracellulare*.

Selected candidate clones were the following 8 clones. In this regard, unless otherwise indicated, hereinafter, the candidate clone selected in the primary screening is referred to as "the primitive candidate clone", and the candidate clone selected finally in the secondary screening is referred to simply as "the candidate clone"

Candidate clone 1: an oligonucleotide with 667 nucleotides having a nucleotide sequence shown in SEQ ID NO: 1;
Candidate clone 2: an oligonucleotide with 1129 nucleotides having a nucleotide sequence shown in SEQ ID NO: 2;
Candidate clone 3: an oligonucleotide with 1003 nucleotides having a nucleotide sequence shown in SEQ ID NO: 3;
Candidate clone 4: an oligonucleotide with 748 nucleotides having a nucleotide sequence shown in SEQ ID NO: 4;
Candidate clone 5: an oligonucleotide with 619 nucleotides having a nucleotide sequence shown in SEQ ID NO: 5;
Candidate clone 6: an oligonucleotide with 511 nucleotides having a nucleotide sequence shown in SEQ ID NO: 6;
Candidate clone 7: an oligonucleotide with 1006 nucleotides having a nucleotide sequence shown in SEQ ID NO: 7;
Candidate clone 8: an oligonucleotide with 702 nucleotides having a nucleotide sequence shown in SEQ ID NO: 8.

Example 1

Evaluation on Specificity of the Candidate Clone for *M. intracellulare*

For the 8 candidate clones obtained in Experimental Example 1, evaluation experiment through the use of PCR amplification system was performed to investigate the potential use of these clones in the specific detection system for *M. intracellulare* by using nucleic acid amplification detection system.

(1) Synthesis of the Primer for PCR

Firstly, based on the result of sequence analysis (nucleotide sequence) of the candidate clone 1, the primer sequence for the PCR amplification detection, namely, the oligonucleotides of "5'-GTTCAGCAGATCGTCGTAGG-37" (SEQ ID NO: 9) and "5'-CTCTTGACGAGGCAAAACAT-3", (SEQ ID NO: 10) were designed using a primer design tool on the web, Primer 3 (Whitehead Institute for Biomedical Research). Hereinafter, the primer having the nucleotide sequence shown in SEQ ID NO: 9 is referred to as "02_Fw1" and the primer having the nucleotide sequence shown in SEQ ID NO: 10 is referred to as "02_Rv1".

The designed oligonucleotide was synthesized by the phosphoamidite method using the ABI 392 DNA synthesizer (Applied Biosystems Inc.). The synthetic procedure was carried out according to the operation manual provided by Applied Biosystems Inc., and the deprotection of various types of oligonucleotides was performed by heating aqueous ammonia solution of the oligonucleotide at 55° C. for overnight. Subsequently, the synthesized oligonucleotide was purified by the anion exchange column chromatography using Pharmacia FPLC.

(2) Preparation of Sample

Using *Escherichia coli* (*E. coli*, ATCC 11775) and 18 species of *Mycobacterium* genus, namely *Mycobacterium tuberculosis* (TMC102[H37Rv]), *M. intracellulare* (ATCC 13950), *Mycobacterium kansasii* (ATCC 12478), *Mycobacterium marinum* (ATCC927), *Mycobacterium simiae* (ATCC25275), *Mycobacterium scrofulaceum* (ATCC19981), *Mycobacterium gordonae* (ATCC14470), *Mycobacterium szulgai* (ATCC35799), *Mycobacterium avium* (ATCC25291), *Mycobacterium gastri* (ATCC15754), *Mycobacterium xenopi* (ATCC19250), *Mycobacterium non-chromogenicum* (ATCC 19530), *Mycobacterium terrae* (ATCC15755), *Mycobacterium triviale* (ATCC23292), *Mycobacterium fortuitum* (ATCC6S841), *Mycobacterium chelonei* (ATCC35752), *Mycobacterium abscessus* (ATCC19977), *Mycobacterium peregrinum* (ATCC14467), DNAs were extracted and purified by the following method to obtain DNA samples.

Firstly, as to *Mycobacterium tuberculosis*, a purified genomic DNA was obtained from Mycos Research, LLC, and used it as the purified DNA.

For the other bacteria, the corresponding microbial strains were obtained from American Type Culture Collection (ATCC), and the DNAs thereof were extracted and purified by the following method. All bacteria used were clinical isolates, and their bacterial strain had already been differentiated by the colony morphology, and the conventional various biochemical tests and the like for the cultured bacterium.

That is, as to the genius of *Mycobacterium* bacteria, at first, the colonies grown on the Ogawa's medium were collected and suspended in purified water, and then autoclaved (at 120° C. under 2 atmospheres for 20 minutes). Subsequently, the microbial cells were subjected to disruption treatment (physical disruption using 2 mm diameter of glass beads), followed by centrifugation to obtain the supernatant solution. From the resultant supernatant solution obtained, the extraction and purification of DNAs were carried out using the ion-exchange resin type DNA extraction and purification kit, Genomic-tip (QIAGEN GmbH).

In addition, as to *E. coli*, according to the conventional procedure of *E. coli* DNA extraction method, the extraction and purification of the DNA were carried out.

Each of the purified DNAs obtained from bacteria of *Mycobacterium* genus was adjusted to give final concentration of 1 ng/μl (in 10 mM Tris-HCl buffer, pH 8.9), and used as a DNA sample.

The purified DNA obtained from *E coli*. was adjusted to give final concentration of 1 ng/μl (in 10 mM Tris-HCl buffer, pH 8.9), and used as a DNA sample.

(3) PCR

The PCR was performed as follows using the primers of 02_Fw1 and 02_Rv1 which were designed and synthesized in the above described (1) based on the nucleotide sequence (SEQ ID NO: 1) of the candidate clone. It should be noted that, the each locating position of the nucleotide sequences of each primer of 02_Fw1 and 02_Rv1 on the nucleotide sequence of the candidate clone 1 were as shown in FIG. 1.

1) Preparation of the Solution for PCR

A 10 mM Tris-HCl buffer solution (pH 8.9) containing 300 nM each of the primer 02_Fw1 and the primer 02_Rv1 obtained in the above described (1), 30 times dilution of the undiluted solution of SYBR™ Green I (Molecular Probes Inc.) as a fluorescein reagent, 1.5 mM $MgCl_2$, 80 mM KCl, 500 μg/ml BSA, 0.1% sodium cholate, 0.1% Triton X-100, 0.2 mM each of dATP, dCTP, dGTP and dTTP, and 40 unit/ml of Taq DNA polymerase (Nippon Gene Co.) was prepared, and used as a reaction solution for PCR.

2) Real-time PCR

Using the DNA sample derived from the bacteria of *Mycobacterium* genus or derived from *E. coli* as a template DNA to be amplified as a target in the PCR, the evaluation test was carried out by way of quantitative monitoring by the intercalation method, according to the following method.

Firstly, to 20 μl of the reaction solution for PCR prepared in the above described 1) of (3), 1 μl (1 ng) of the DNA sample prepared in the above described (2) was added and used as a sample for PCR. This sample for PCR was placed in each well of a 96-well reaction plate (MicroAmp Optical 96-well Reaction Plate; Applied Biosystems Japan Ltd.), and the real-time PCR was performed using a specialized thermal cycler/detector for the TaqMan™ PCR (ABI 7500, Applied Biosystems Japan Ltd.). After keeping the temperature at 95° C. for 10 minutes, a reaction cycle composed of heating at 95° C. for 15 seconds and 60° C. for 1 minute was repeated for 40 cycles, and the fluorescence intensity of SYBR™ Green I which had been intercalated into the amplification products was measured.

(4) Melting Curve Analysis

As to each amplified product for individual DNA sample, the melting curve was depicted by plotting the melting temperature of the primer extension product (double-stranded DNA) as horizontal axis and the first derivation (variation) of fluorescence intensity as vertical axis, and then detection of peak was examined.

(5) Result

The results of the melting curve analysis obtained for each DNA sample are shown collectively in FIG. 9.

As is clear from the results shown in FIG. 9, as the result of the melting curve analysis of the nucleic acid which had been amplified using the primer 02_Fw1 and the primer 02_Rv1 of the present invention in the presence of SYBR Green I, only the case when the DNA sample derived from *M. intracellulare* was used as a template (FIG. 1: *M. intracellulare*) was able to be determined as positive, because a fluorescent signal generated as the result of nucleic acid amplification was confirmed.

On the other hand, as is clear from FIG. 9, when the real-time PCR was performed in the same way using the DNA derived from bacteria of *Mycobacterium* genus except for *M. intracellulare* or the DNA derived from the bacteria of other genus like *E. coli* as a template, and using a combination of the same primers, corresponding fluorescent signal was not confirmed (FIG. 9: other species), and all cases were able to be determined as negative.

Further, as is clear from FIG. 9, from the fact that a single clear peak was obtained as the result of the melting curve analysis when the DNA sample derived from *M. intracellulare* was used as a template, it can be understood that the detection system carried out was a detection method having a quite high specificity for *M. intracellulare*.

From the above results, by using the oligonucleotide of the present invention as a primer for PCR, it can be understood that *M. intracellulare* can be detected specifically. In addition, since the detection by nucleic acid amplification such as PCR can be expected to provide a high sensitivity, isolation of bacterium is not necessary, and the clinical specimen can be used directly for the detection. Therefore, the detection of *M. intracellulare* can be finished within a day at the longest, whereas the conventional method in which the bacterial cultivation is required before detection used to take several weeks.

Example 2

Verification of Sensitivity of the Candidate Clone to Detect *M. Intracellulare*

(1) Synthesis of the Primer for PCR for Detection of *M. intracellulare*

Using the same equipment and by the same procedure as described in (1) of Example 1, the primer 02_Fw1 and the primer 02_Rv1 were synthesized.

(2) Preparation of the Probe for the Detection of *M. intracellulare*

From the nucleotide sequence shown in SEQ ID NO: 139 (155 nucleotides) which was anticipated to be amplified by the PCR using 02_Fw1 and 02_Rv1 as primers, a sequence "5'-ATACGTGCCCAGAAGCTCTACCGAGAT-3'" to be used as a probe was designed, and an oligonucleotide consisting of this sequence was synthesized (SEQ ID NO: 204; hereinafter, the oligonucleotide probe having this sequence is described as INT 0 2_F1R1_FAMTAM). The 5'-terminal of this oligonucleotide was labeled with a reporter dye of FAM and the 3'-terminal was labeled with a reporter quencher of TAMRA, and thus a labeled oligonucleotide probe (TaqMan™ Fluorescent Probe; Applied Biosystems Japan) was obtained.

(3) Preparation of the DNA Sample for PCR

For the DNA sample derived from *M. intracellulare* prepared in (1) of Experimental Example 1, quantity of the DNA in the sample was determined by measuring absorbance thereof. The quantity of the DNA (copy number of the genome) in the sample was determined by comparing the obtained quantity of DNA with the known quantity of the genomic DNA of *M. intracellulare*. A $10^8$ copy/μl of the genomic DNA was obtained.

Subsequently, the DNA sample was diluted using 10 mM Tris-HCl buffer, pH 8.9 to a dilution series of $10^5$, $10^4$, $10^3$, $10^2$, 10, 5 and 2 copy/μl, and used as a DNA sample for PCR.

(4) Real-time PCR

Using the primer 02_Fw1 as a forward primer and the primer 02_Rv1 as a reverse primer prepared in the above (1), the real-time PCR was performed as follows.

That is, a 10 mM Tris-HCl buffer solution (pH8.9) containing 1 μM each of the primer 02_Fw1 and the primer 02_Rv1, 195 nM of the fluorescence labeled probe INT 0 2_F1R1_FAMTAM prepared in the above (2), 1.5 mM $MgCl_2$, 80 mM KCl, 500 μg/ml BSA, 0.1% sodium cholate, 0.1% Triton X-100, 0.2 mM each of dATP, dCTP, dGTP and dTTP, and 40 unit/ml of Taq DNA polymerase (Nippon Gene Co.) was prepared and used as reaction solution.

To 20 μl of the reaction solution, 1 μl of each dilution series of DNA sample was added and used as a sample for PCR. This sample for PCR was placed in each well of a 96-well reaction plate (MicroAmp Optical 96-well Reaction Plate; Applied Biosystems Japan Ltd.), and the real-time PCR was performed using a specialized thermal cycler/detector for the TaqMan™ PCR (ABI 7500, Applied Biosystems Japan Ltd.). After keeping the temperature at 95° C. for 10 minutes, a reaction cycle composed of heating at 95° C. for 15 seconds and 60° C. for 1 minute was repeated for 50 cycles, and in every cycle, the fluorescence intensity of reporter dye was measured. It should be noted that, fluorescence intensity was measured by using a function of the thermal cycler used for the measurement to calculate relative fluorescent intensity ratio, for each of the 96 well reaction plates used for the measurement.

(5) Result

From the data obtained, a standard curve was made up according to the conventional procedure commonly performed in the real-time PCR method.

That is, as to each of the DNA samples for PCR, the fluorescence intensity of reporter dye (Rn, y-axis) was plotted for each cycle number of PCR (x-axis) to make up an amplification curve. After that, an Rn part where the fluorescence intensity amplified exponentially was selected, and a Threshold line (Th) was drawn. The crossing point of the Th with the fluorescence intensity of each DNA sample for PCR was defined as Threshold cycle (Ct). After that, the Ct value (y-axis) was plotted for the copy number of the genome of each used DNA sample for PCR (x-axis), and the approximated curve obtained for each Ct was used as a standard curve. The standard curve obtained is shown in FIG. 10.

$$y = -3.825x + 38.78$$

$$R^2 = 0.996$$

In consequence, from the fact that the fluorescent signal was detected by the real-time PCR, it is confirmed that *M. intracellulare* can be detected by performing the real-time PCR using the oligonucleotide of the present invention as a primer and by designing a labeled probe based on the sequence of the region to be amplified.

In addition, it is confirmed that, since the standard curve can be made up, quantitative determination of *M. intracellulare* is possible by the real-time PCR using the primer and the probe of the present invention. Further, it can be understood from FIG. 10 that the real-time PCR method using the primer and the probe of the present invention can detect *M. intracellulare* even under the condition where only 2 copies of the genomic DNA of *M. intracellulare* are present as the initial quantity.

Furthermore, in the case where the real-time PCR method is applied, the quantitative determination of the initial quantity of the template DNA can be performed more accurately, because the fluorescent intensity is monitored in real time, and therefore, the method is effective for detecting *M. intracellulare*.

Industrial Applicability

According to the method for detecting *M. intracellulare* by using the primer and/or probe of the present invention, the detection of *M. intracellulare* can be performed more rapidly and with higher accuracy compared with a conventional bacterial species identification method performed by culture examination on a bacterium. Further, the method for detecting *M. intracellulare* of the present invention can exclude any false-positive result for the diagnosis and can also detect and diagnose *M. intracellulare* with higher accuracy compared with a diagnosis method performed by is PCR using a conventional primer and/or probe. Still further, the method for detecting *M. intracellulare* of the present invention can quantify the *M. intracellulare* cell.

SEQUENCE LISTING

<160> NUMBER OF SEQ ID NOS: 208

<210> SEQ ID NO 1
<211> LENGTH: 666
<212> TYPE: DNA
<213> ORGANISM: Mycobacterium intracellulare

<400> SEQUENCE: 1

```
acaaagtccg tgacgtcgtt cagcagatcg tcgtaggagc ccgtaatcac ttccaacttg      60
acgtccgcga tgtacgcata gcgacggaga tacgtgccca gaagctctac cgagatgttg     120
gcggcgattc cgagcttgac cgtccggccg gtatgttttg cctcgtcaag agtggacaac     180
gccttaagca catcggtcat ggccgcggtt gggtcgcgca gaatctccaa ggcttcagtg     240
cgagcatcac tcacgacatc gttcccccgc cattcacctt caggctttgc cccgtgatgt     300
aggaggcctg atcggatagc aaaaaggcga cggccccgc cgtatcttcc ggcgtaccca      360
agcggcgcaa cggttttaga cgcgctgtca tcagctgctg cttttcagaa atgccgctga    420
taaatctggt gtccgtcata cccggggaga cgcagttgat cgtgatcccc tgcgggccaa    480
gctctgcggc gaggtaccgc gccatcgtcg ccagagcgcc cttggccgtg gcgtaagccg    540
tccacccgct cacggggcg ccgtcgatgg atttccgatg taatgcaaac gatgcggcct    600 ccccgttat ccgccatgag cggcgcgacc gcttggaccg acaggaacgc gcttttaacc    660
tgtaca                                                              666
```

<210> SEQ ID NO 2
<211> LENGTH: 1128
<212> TYPE: DNA
<213> ORGANISM: Mycobacterium intracellulare

<400> SEQUENCE: 2

```
cacacttccg cgcgacccgc ctcattgggg tatctccaaa gtccaatccc atacgctcgc      60
```

-continued

```
cgcgaaattg aaccccgcgc ccacgccggc tagcaccacg cgctggcctc ggctcaactt        120
gcgtttgtgc accgcttcgc tcagtgcgat tgcaagcgat gccgagccag tgttacccac        180
ctcggcgacg ttggcatatg tcttatccaa accgaatccc attttttca cgaggtattc         240 gatcaagcgc agattcgcct ggtggaacac gacgaagtcg atgtcgctga tctcgtagcc        300
cgacttggcg actgccttgc gaatggtggg gggcagatga gtgatggcct gcttccacgt        360
cgcaataccg ttcatctcca tcaagtccac cgcgcgatcg aacggccgac cgttcgtggg        420
aaacatcgag cctccgccgc gctggcgcac ggcatcgaag ttcgagctgt ccgtgtggaa        480
ggcggagtgg cggatgccgc cttgctgcac tcggctcagt acggctgcac cggcgccatc        540
actgaggtat atggcggtgt tgacgtcgct gccatcgatg tagcggctaa gcatttcaac        600
gccgataacc agcgcgtagc gcacagtgtc gtccaccttc atgcgatcgg acgctgccgt        660
caaccctgtg acgaagcccg agcagttggc ttgcacatcg tagatctgtg cgtgctttgc        720
ctcgagctgc tgctgcacct tggcggagac cggcggatag atgtagtccc cagagaaggt       780
gcaacagata atgacgtcta gttgctcggc ggagacttgc gccatcgcca tcgcctgctt        840
agctgcggcc actgcgaacc cccacgcggt gtcttgcggg tctgcaatac ggcgctggcg        900
gataccagtt ttttcttcga tccagtcagg cgtaatggct tgtgccgggt ccagcttctg        960
gcacagctcg tcgttgccga ccactcgcgc aggtaggtgg tgcccactc cgacgatgga       1020 aacggcgggc aatgggacgg cagaagtcgg aacagagttc atagcgtaaa ggttgcaacc       1080
ctctcagtga caggcgtgcg ctacgtcggc gtgcagtgcg ggtcacat                    1128
```

<210> SEQ ID NO 3
<211> LENGTH: 1002
<212> TYPE: DNA
<213> ORGANISM: Mycobacterium intracellulare

<400> SEQUENCE: 3

```
cacccttcg cgcgcatttc tgacgagtca acgcggttcg gctcggctaa tcgtgacgaa         60
cgcgtgttcg ccgatcccga cgtgtttgat atcgggcgca aacccgaaca ccaagtggcg        120
ttcggccgag gcattcactt ctgtctgggt gcgtcgttag cgcggatgga ggcccgaccg        180
caggcgttgc gcgccctgct ggcccgcgtg cccaactggg aagtcgacct agagcgcgcg        240
caacgcctgc ggtcgggccc gatccgaggt tatctgtcgt tgccgatctc gtggtcggcg        300
aattagccgc gctgcaggct agtcggagcc gctgcggcgc gaaactggtt tacggctgac        360
ggcccgctgt gcgggtttat ctgcctggcg gcggtgcgcg acgaggaagt catcgacgat        420
gcgctcgcag tcttgacgat cgatggcacg cagcccggtg aggcgggcga acgccacagg       480
cccgatgagt tgacacagga tcagctccat gtcgaagtca tccaggtcgg cgcgagcttc        540
gggggctttg caacagggca acgaacggtt gtcgatattg gtcgatgatc cgcgcgcgca        600
gcgcgtgtcg gtcctgggtt tcctgggtgc cgtcgggtgt gggccaagc gcgacccaag        660 ccagggtggt gacatgcagc ggggcttcct ggaacagcgt ggcctgtcgg ctcaacagtt        720
cgatgagttg gtcgcgcaac gatccagtcg ccggtgggg gtgcacctgc ggcagtagcc        780
gctcaaatgt ggcggccagc agttgagtgg agctgctgaa gtggcggtac agggtcgtcc        840
gcgcgacttt ggaggccttg gtgacggcat cgatggtgac ggcttcgatg ccgccggcgc        900
tcaggagttt ggtggccgca tccaagagcc gggttcgtga gcgcagccgg cgcgggtcaa       960
cgtcgtcatc gtcgtcgacc gggaattcca gggtgtcacg ct                         1002
```

```
<210> SEQ ID NO 4
<211> LENGTH: 747
<212> TYPE: DNA
<213> ORGANISM: Mycobacterium intracellulare

<400> SEQUENCE: 4
tggtgggaaa tgatgaagcg gcggccttta cgggacgacg tctttcagac cgtggacttg      60
gatttctggt tgcgccttat gctgcgatca gcggtttgct ttgtaccgca agagctctcg     120
gtacgtcatc acaccgctac caccgagtcc gcgaacatca ccaagtccca tcggcactgg     180
ctggaccagc tacgcattct gacgtggatg atcgtggacc cggcatccac acgcgctgtc     240
cgagccgctg caacgccatg gtgggcgctt gtctggctgg gactgctctt caaagtgacg     300
gcgttcggac ctcagcggtc ctcgcggctg aaggcgttgc tcgtggcgcc cgctagtgag     360
ttcgcccggg cgaggcggtt tcgcgctaat cttacgcgtc catcgcgata gccaactgag     420
aagcacgtcg ctcttcgccg tcaccgtcca aaattcgacg agggctgcga gcgccggtgt     480
acgctcaccg cgtgcctccc ctgatgatgg ccgacagcaa cacgctcgta catcgggcgc     540
cgcctgggac cgtaggagct cgcagtatcc gattcaggac tactcggaag acgactctgc     600
ccatcacaac gctcgggtct tgcgcggga cgaatccccg tcttcctcct cttcatctac     660
aaaattgtgc tcggcgaaca ggtgcacaag gtgactggtg tcgacagcat ttacggcgtg     720
gtccccatgt gcgccgtgat tccgca                                          747

<210> SEQ ID NO 5
<211> LENGTH: 618
<212> TYPE: DNA
<213> ORGANISM: Mycobacterium intracellulare

<400> SEQUENCE: 5
gactgcgaca acacgctttg gggaggcatc gtcggggaag atgggccgac cggcatcggg      60
ctcgatccgt acgactaccc aggcaatgtc ttttggactg tgcagcaaca gcttcgccag     120
ctcgaatcaa ttgggatttt gctctgccta tgcactaaga ataacgccgc agatgtggac     180
gaagtgtttg cgacgcaccc taacgcggtg ctgaaggatg aacacttcgc ggccaagaag     240
gtgaattggg agccgaaggt tgcgaacctg caagccctag cgaaggagct gaacctcgga     300
ccggagagtt tcatatttat cgacgactcc gtattcgagt tggaggccgt tcgcgcacag     360 ttgcccccaag tcagggtatt tcaggtcccg aagaagttga gcgactaccc ggcgatgctg     420
cgcgacgtga ccgcgctctg cgtggccggc ggagtagtca gcgagagcga aaataagacg     480
cgtcactaca gactgctggc cgagtcatcc gctgcgcaag cgaacttcgc gaatcaagag     540
gattacctac gctcgttgga cttggaggtg cgcatctacc gcgacgcgcg cgagcagatt     600
ccccgcatag ccgaactg                                                    618

<210> SEQ ID NO 6
<211> LENGTH: 510
<212> TYPE: DNA
<213> ORGANISM: Mycobacterium intracellulare

<400> SEQUENCE: 6
aaagaacaca acgacggtca gtctttagtc atgcaaatgg cgctgcaggg cctcgcgact      60
aactggatcg gagagcccac caacgttatg ttccggcgtc aactggcgct cgacgcagga     120
ggcatccgct ccgacatcgc tcatctatcg gatttggacc tctggttgcg tatgctgctg     180
agatcggcgc cttgcttcgt cccgcaagaa ctctcagtac gacaacattc cccgtttacg     240
gtacaaactt tcgatgcacg accctggtgg cttgaccggc tgcgccttct gacttgggtg     300
```

```
atcgttgatc cgcatcacc catcatgatc cgacttactg cgggaatgtg gtgggtgccc    360
gtctggctgc tacgagctct agaagtcatt gtctacgggc cggacagagt ctcacggatg    420
aaaacgttga tgctcgcccc cgtccgtgag ttcgcccgag cccggcggct ccgtgccaac    480
ctgaggtgga aggagtcgta gtcccgcacg                                     510

<210> SEQ ID NO 7
<211> LENGTH: 1005
<212> TYPE: DNA
<213> ORGANISM: Mycobacterium intracellulare

<400> SEQUENCE: 7
gagccgctcc gcctacatgg tcgaagtggc cgtgagtgca cagcacagct tcaggggccc     60
agtcgaggtc gttcagcttc ttctccaacg acgcggaatc cagtcctggg tcgacgatca    120
cacaacgacc aggtgcgcca gaggctaaaa gatacgtatt tgaggaaaag ccttggtttg    180
ccacgatttg caaagcgccg gcgctggtag tcatttctgt caggccgcct ccgtgcagca    240
gcgtcgaagg cgctgcacaa acgatgttga acgcgatata agcatctcaa tgtaccccgc    300
cgaggtacac cgtctgcgca gtgatacacc cgctgccagg tccacaaaag aaatcgagca    360
catgcgccac gtcttcacgc gtcgccatgc gcgcaagcgg cagggcggcg atcacggcat    420
tgactttatc gcgcggtagc tggcttaaca tgtcagtttc gaaggcgctg atcccgagcg    480
tgttacaggt gatgttcgtg gtggccagtt cctttgccat tatgttggcg agagtggtga    540
ccgcagcctt ggtggcagcg tagaccgagt cgcccatggg ctctaggctc acggccatcg    600
agctcacgct gacgatgcga ccccatttac ccttgcgcat gagcttcgcg gcctcgcgtg    660
agacgaggaa cgtgcctaac aaattcgttt cgaccatggc ctgggccgac gcggccggca    720
gtatcattgc gtactgcgag gtcagcacag cggcgttgtt gacgcagatg tccagcttgc    780
cgaaacgctt gcgaatttct tcgaaaccag cgctgactga acttgcgtcc cgatgtcga    840 cggctacgtc gtagcgacgg tccgacttgg gaacttcatc gacatggcga ctaaacccca    900
ccacgtgcgc cccgcgccgc tcgaaatgtt cagcgaccac ggcgcccaga ccccgacgcg    960
cgccggttac caacaccacc ttttcgtcat agcttgcgga catcg                   1005

<210> SEQ ID NO 8
<211> LENGTH: 700
<212> TYPE: DNA
<213> ORGANISM: Mycobacterium intracellulare

<400> SEQUENCE: 8
tcggatggct tggtcgacgg ccggggcggt agccgaaagc tgctgtagca gcggacggaa     60
ccgctggact tgggatccac tggattgggc ttgggtgagg agtccggtca acggggtcaa    120
cgcggtgcgc aaggtggtgt ccagttcgcg gagaccgccg gcgagttggt cggcgccgtg    180
ggtgagtttg gccaggtcat ccttgtgtgc gtctcccttg gcgaccgcgc cggccatctt    240
gtcgccaatc tcgccgtttt gccacgacag ttgagcctgg tccagacgcg cgcccgtcgg    300
ccgggtgaca ccggagacct tggtgacgcc gggcagttgc gagacccgag aggccatttc    360
atccaggtcg gccagggcct tgctggtgcg catatcggtg ggcgattcga cgaccatgaa    420
ttcggtgacg atggcgtcct tgcgaaagtg cctgtccagc agtcgatatc cctcattgct    480
ggccggtggc gccggctgtc ctcggcgatc gtcgtagctg atgtgcatag tcagcgcgac    540
agccgccagg cctagcacca gcgccagact ggcgaccaat agcggcacgg tcgacggac    600 caccgccacg gcgatccagt tccagtagcg gcgagtgcga tctgccttgg gttcaccgat    660
```

```
gccgcgtttg gccgctagcg ccaacaccgg gggaaataac                               700

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
gttcagcaga tcgtcgtagg                                                     20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
ctcttgacga ggcaaaacat                                                     20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
cgctgataaa tctggtgtcc                                                     20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
tacgtgccca gaagctctac                                                     20

<210> SEQ ID NO 13
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 13
attcaccttc aggctttgc                                                      19

<210> SEQ ID NO 14
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 14
catcactcac gacatcgttc                                                     20

<210> SEQ ID NO 15
<211> LENGTH: 21
<212> TYPE: DNA
<213> ORGANISM: Artificial Sequence
```

```
<220> FEATURE:
<223> OTHER INFORMATION: oligonucleotide primer

<400> SEQUENCE: 15
ccgtaatcac ttccaacttg a                                              21

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 16
aatctggtgt ccgtcatacc                                                20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 17
tacatcggaa atccatcgac                                                20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 18
gatcaggcct cctacatcac                                                20

<210> SEQ ID NO 19
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 19
atcacgatca actgcgtctc                                                20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 20
gatgacagcg cgtctaaaac                                                20

<210> SEQ ID NO 21
<211> LENGTH: 20
<212> TYPE: DNA
<213> ORGANISM: Artificial Sequence
<220> FEATURE:
<223> OTHER INFORMATION: oligonuleotide primer

<400> SEQUENCE: 21
gatgtgctta aggcgttgtc                                                20
```

```
<210> SEQ ID NO 22
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 22
gttaaaagcg cgttcctgt                                                   19

<210> SEQ ID NO 23
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 23
acagtgtcgt ccaccttcat                                                  20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 24
caccttctct ggggactaca                                                  20

<210> SEQ ID NO 25
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 25
cgcctcattg gggtatct                                                    18

<210> SEQ ID NO 26
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 26
ggctcaactt gcgtttgt                                                    18

<210> SEQ ID NO 27
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 27
cacgaggtat tcgatcaagc                                                  20

<210> SEQ ID NO 28
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 28
```

-continued gttcgtggga aacatcgag                                                19

<210> SEQ ID NO 29
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 29
gtagcggcta agcatttcaa                                               20

<210> SEQ ID NO 30
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 30
aaggtgcaac agataatgac g                                             21

<210> SEQ ID NO 31
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 31
cttgcgggtc tgcaatac                                                 18

<210> SEQ ID NO 32
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 32
ttttcttcga tccagtcagg                                               20

<210> SEQ ID NO 33
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 33
taacactggc tcggcatc                                                 18

<210> SEQ ID NO 34
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 34
aagtcgggct acgagatca                                                19

<210> SEQ ID NO 35
<211> LENGTH: 20
<212> TYPE: DNA
<213> ORGANISM: Artificial Sequence

```
<220> FEATURE:
<223> OTHER INFORMATION: oligonucleotide primer

<400> SEQUENCE: 35
atggagatga acgtattgc                                            20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 36
aacaccgcca tatacctcag                                           20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 37
caaagcacgc acagatctac                                           20

<210> SEQ ID NO 38
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 38
gacgagctgt gccagaag                                             18

<210> SEQ ID NO 39
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 39
aactctgttc cgacttctgc                                           20

<210> SEQ ID NO 40
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 40
ctgtcactga gagggttgc                                            19

<210> SEQ ID NO 41
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 41
gaaactggtt tacggctgac                                           20
```

```
<210> SEQ ID NO 42
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 42
gacttcgaca tggagctgat                                              20

<210> SEQ ID NO 43
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 43
cctttcgcgc gcatttct                                                18

<210> SEQ ID NO 44
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 44
tgggaagtcg acctagagc                                               19

<210> SEQ ID NO 45
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 45
gctcgcagtc ttgacgat                                                18

<210> SEQ ID NO 46
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 46
acaggcccga tgagttgac                                               19

<210> SEQ ID NO 47
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 47
aagccagggt ggtgacat                                                18

<210> SEQ ID NO 48
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 48
```
ggctcaacag ttcgatgagt                                          20

<210> SEQ ID NO 49
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 49
gcagtagccg ctcaaatg                                            18

<210> SEQ ID NO 50
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 50
ttgagtggag ctgctgaagt                                          20

<210> SEQ ID NO 51
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 51
gcacccagac agaagtgaa                                           19

<210> SEQ ID NO 52
<211> LENGTH: 18
<212> TYPE: DNA
<213> ORGANISM: Artificial Sequence
<220> FEATURE:
<223> OTHER INFORMATION: oligonucloreotide primer

<400> SEQUENCE: 52
gcagataaac ccgcacag                                            18

<210> SEQ ID NO 53
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 53
aatatcgaca accgttcgtt                                          20

<210> SEQ ID NO 54
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 54
gaaacccagg accgacac                                            18

<210> SEQ ID NO 55
<211> LENGTH: 20
<212> TYPE: DNA
<213> ORGANISM: Artificial Sequence

```
<220> FEATURE:
<223> OTHER INFORMATION: oligonucleotide primer

<400> SEQUENCE: 55
ttcagcagct ccactcaact                                           20

<210> SEQ ID NO 56
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 56
accaaggcct ccaaagtc                                             18

<210> SEQ ID NO 57
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 57
gccaccaaac tcctgagc                                             18

<210> SEQ ID NO 58
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 58
acgatgacga cgttgacc                                             18

<210> SEQ ID NO 59
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 59
tggacttgga tttctggttg                                           20

<210> SEQ ID NO 60
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 60
atccacgtca gaatgcgtag                                           20

<210> SEQ ID NO 61
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 61
gaacatcacc aagtcccatc                                           20
```

```
<210> SEQ ID NO 62
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 62
tggtgggaaa tgatgaagc                                              19

<210> SEQ ID NO 63
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 63
gggacgacgt ctttcaga                                               18

<210> SEQ ID NO 64
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 64
cttgtctggc tgggactg                                               18

<210> SEQ ID NO 65
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 65
cggtttcgcg ctaatcttac                                             20

<210> SEQ ID NO 66
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 66
cgtccaaaat tcgacgag                                               18

<210> SEQ ID NO 67
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 67
gtgcctcccc tgatgatg                                               18

<210> SEQ ID NO 68
<211> LENGTH: 19
<212> TYPE: DNA
<213> ORGANISM: Artificial Sequence
<220> FEATURE:
<223> OTHER INFORMATION: ologonucleotide primer

<400> SEQUENCE: 68
```
gagctcgcag tatccgatt                                                19

<210> SEQ ID NO 69
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 69
tactcggaag acgactctgc                                                20

<210> SEQ ID NO 70
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 70
ccgtcacttt gaagagcagt                                                20

<210> SEQ ID NO 71
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 71
gagagctctt gcggtacaaa                                                20

<210> SEQ ID NO 72
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 72
gtcagaatgc gtagctggtc                                                20

<210> SEQ ID NO 73
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 73
cgatggacgc gtaagattag                                                20

<210> SEQ ID NO 74
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 74
gatgtacgag cgtgttgct                                                 19

<210> SEQ ID NO 75
<211> LENGTH: 20
<212> TYPE: DNA
<213> ORGANISM: Artificial Sequence

```
<220> FEATURE:
<223> OTHER INFORMATION: oligonucleotide primer

<400> SEQUENCE: 75
tcgtcttccg agtagtcctg                                               20

<210> SEQ ID NO 76
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 76
gccgagcaca attttgtaga                                               20

<210> SEQ ID NO 77
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 77
gtcgacacca gtcaccttgt                                               20

<210> SEQ ID NO 78
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 78
cacgccgtaa atgctgtc                                                 18

<210> SEQ ID NO 79
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 79
tacgactacc caggcaatgt                                               20

<210> SEQ ID NO 80
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 80
cgaagtgttc atccttcagc                                               20

<210> SEQ ID NO 81
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 81
ccgaagaagt tgagcgacta                                               20
```

-continued

```
<210> SEQ ID NO 82
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 82
actgcgacaa cacgcttt                                                 18

<210> SEQ ID NO 83
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 83
tcgaatcaat tgggattttg                                               20

<210> SEQ ID NO 84
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 84
ggtgctgaag gatgaacact                                               20

<210> SEQ ID NO 85
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 85
ggaccggaga gtttcatatt t                                             21

<210> SEQ ID NO 86
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 86
cagcgagagc gaaaataaga                                               20

<210> SEQ ID NO 87
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 87
tccaacgagc gtaggtaatc                                               20

<210> SEQ ID NO 88
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 88
```
cggcgttatt cttagtgcat                                               20

<210> SEQ ID NO 89
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 89
gttcagctcc ttcgctagg                                                19

<210> SEQ ID NO 90
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 90
gggacctgaa ataccctgac                                               20

<210> SEQ ID NO 91
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 91
tttcgctctc gctgactact                                               20

<210> SEQ ID NO 92
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 92
ctatgcgggg aatctgct                                                 18

<210> SEQ ID NO 93
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 93
catcgctcat ctatcggatt                                               20

<210> SEQ ID NO 94
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 94
aacgatcacc caagtcagaa                                               20

<210> SEQ ID NO 95
<211> LENGTH: 20
<212> TYPE: DNA
<213> ORGANISM: Artificial Sequence

```
<220> FEATURE:
<223> OTHER INFORMATION: oligonucleotide primer

<400> SEQUENCE: 95
cgactaactg gatcggagag                                               20

<210> SEQ ID NO 96
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 96
ctccgacatc gctcatctat                                               20

<210> SEQ ID NO 97
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 97
tcccgcaaga actctcagta                                               20

<210> SEQ ID NO 98
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 98
acttactgcg ggaatgtggt                                               20

<210> SEQ ID NO 99
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 99
cttctgactt gggtgatcgt                                               20

<210> SEQ ID NO 100
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 100
gtaccgtaaa cggggaatgt                                               20

<210> SEQ ID NO 101
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 101
tcgtgcatcg aaagtttgta                                               20
```

```
<210> SEQ ID NO 102
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 102
ccgcagtaag tcggatcat                                              19

<210> SEQ ID NO 103
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 103
tacgactcct tccacctcag                                             20

<210> SEQ ID NO 104
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 104
gagcatcaac gttttcatcc                                             20

<210> SEQ ID NO 105
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 105
cgcgatataa gcatctcaat g                                           21

<210> SEQ ID NO 106
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 106
acatgttaag ccagctaccg                                             20

<210> SEQ ID NO 107
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 107
gcctacatgg tcgaagtgg                                              19

<210> SEQ ID NO 108
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 108
```
tcagcttctt ctccaacgac                                              20

<210> SEQ ID NO 109
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 109
gcgctggtag tcatttctgt                                              20

<210> SEQ ID NO 110
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 110
cacggcattg actttatcg                                               19

<210> SEQ ID NO 111
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 111
attatgttgg cgagagtggt                                              20

<210> SEQ ID NO 112
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 112
cgtgagacga ggaacgtg                                                18

<210> SEQ ID NO 113
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 113
catcgagctc acgctgac                                                18

<210> SEQ ID NO 114
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 114
cgaccccatt tacccttg                                                18

<210> SEQ ID NO 115
<211> LENGTH: 20
<212> TYPE: DNA
<213> ORGANISM: Artificial Sequence

```
<220> FEATURE:
<223> OTHER INFORMATION: oligonucleotide primer

<400> SEQUENCE: 115
gacttgggaa cttcatcgac                                               20

<210> SEQ ID NO 116
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 116
accagcgctg actgaactt                                                19

<210> SEQ ID NO 117
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 117
accaaggctt ttcctcaaat                                               20

<210> SEQ ID NO 118
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 118
cggcctgaca gaaatgacta                                               20

<210> SEQ ID NO 119
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 119
cgatttcttt tgtggacctg                                               20

<210> SEQ ID NO 120
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 120
gtctacgctg ccaccaag                                                 18

<210> SEQ ID NO 121
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 121
acgaatttgt taggcacgtt                                               20
```

```
<210> SEQ ID NO 122
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 122
agaaattcgc aagcgtttc                                              19

<210> SEQ ID NO 123
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 123
ctcgcagtac gcaatgatac                                             20

<210> SEQ ID NO 124
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 124
ggacatctgc gtcaacaac                                              19

<210> SEQ ID NO 125
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 125
gcaagctatg acgaaaaggt                                             20

<210> SEQ ID NO 126
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 126
cgaaaaggtg gtgttggtaa                                             20

<210> SEQ ID NO 127
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 127
cgatcgtcgt agctgatgt                                              19

<210> SEQ ID NO 128
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 128
```
ggtgaaccca aggcagat                                               18

<210> SEQ ID NO 129
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 129
ggtagccgaa agctgctg                                               18

<210> SEQ ID NO 130
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 130
ctggacttgg gatccactg                                              19

<210> SEQ ID NO 131
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 131
aaggtggtgt ccagttgc                                               18

<210> SEQ ID NO 132
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 132
gagaggccat ttcatccag                                              19

<210> SEQ ID NO 133
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 133
gtcgatatcc ctcattgctg                                             20

<210> SEQ ID NO 134
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 134
atgacctggc caaactcac                                              19

<210> SEQ ID NO 135
<211> LENGTH: 19
<212> TYPE: DNA
<213> ORGANISM: Artificial Sequence

```
<220> FEATURE:
<223> OTHER INFORMATION: oligonucleotide primer

<400> SEQUENCE: 135
gagacgcaca caaggatga                                                    19

<210> SEQ ID NO 136
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 136
gtctggacca ggctcaac                                                     18

<210> SEQ ID NO 137
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 137
gatatcgact gctggacagg                                                   20

<210> SEQ ID NO 138
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 138
actcgccgct actggaac                                                     18

<210> SEQ ID NO 139
<211> LENGTH: 155
<212> TYPE: DNA
<213> ORGANISM: Artificial Sequence
<220> FEATURE:
<223> OTHER INFORMATION: oligonucleotide probe

<400> SEQUENCE: 139
gttcagcaga tcgtcgtagg agcccgtaat cacttccaac ttgacgtccg cgatgtacgc       60
atagcgacgg agatacgtgc ccagaagctc taccgagatg ttggcggcga ttccgagctt      120
gaccgtccgg ccggtatgtt ttgcctcgtc aagag                                 155

<210> SEQ ID NO 140
<211> LENGTH: 168
<212> TYPE: DNA
<213> ORGANISM: Artificial Sequence
<220> FEATURE:
<223> OTHER INFORMATION: oligonucleotide probe

<400> SEQUENCE: 140
cgctgataaa tctggtgtcc gtcatacccg gggagacgca gttgatcgtg atcccctgcg       60
ggccaagctc tgcggcgagg taccgcgcca tcgtcgccag agcgcccttg gccgtggcgt      120
aagccgtcca cccgctcacg ggggcgccgt cgatggattt ccgatgta                   168

<210> SEQ ID NO 141
<211> LENGTH: 223
<212> TYPE: DNA
<213> ORGANISM: Artificial Sequence
```

<220> FEATURE:
<223> OTHER INFORMATION: oligonucleotide probe

<400> SEQUENCE: 141

| tacgtgccca gaagctctac cgagatgttg gcggcgattc cgagcttgac cgtccggccg | 60 |
| gtatgttttg cctcgtcaag agtggacaac gccttaagca catcggtcat ggccgcggtt | 120 |
| gggtcgcgca gaatctccaa ggcttcagtg cgagcatcac tcacgacatc gttccccgc | 180 |
| cattcacctt caggctttgc cccgtgatgt aggaggcctg atc | 223 |

<210> SEQ ID NO 142
<211> LENGTH: 195
<212> TYPE: DNA
<213> ORGANISM: Artificial Sequence
<220> FEATURE:
<223> OTHER INFORMATION: oligonucleotide probe

<400> SEQUENCE: 142

| attcaccttc aggctttgcc ccgtgatgta ggaggcctga tcggatagca aaaggcgac | 60 |
| ggccccgcc gtatcttccg gcgtacccaa gcggcgcaac ggttttagac gcgctgtcat | 120 |
| cagctgctgc ttttcagaaa tgccgctgat aaatctggtg tccgtcatac ccggggagac | 180 |
| gcagttgatc gtgat | 195 |

<210> SEQ ID NO 143
<211> LENGTH: 148
<212> TYPE: DNA
<213> ORGANISM: Artificial Sequence
<220> FEATURE:
<223> OTHER INFORMATION: oligonucletoide probe

<400> SEQUENCE: 143

| catcactcac gacatcgttc ccccgccatt caccttcagg ctttgccccg tgatgtagga | 60 |
| ggcctgatcg gatagcaaaa aggcgacggc ccccgccgta tcttccggcg tacccaagcg | 120 |
| gcgcaacggt tttagacgcg ctgtcatc | 148 |

<210> SEQ ID NO 144
<211> LENGTH: 154
<212> TYPE: DNA
<213> ORGANISM: Artificial Sequence
<220> FEATURE:
<223> OTHER INFORMATION: oligonucleotide probe

<400> SEQUENCE: 144

| ccgtaatcac ttccaacttg acgtccgcga tgtacgcata gcgacggaga tacgtgccca | 60 |
| gaagctctac cgagatgttg gcggcgattc cgagcttgac cgtccggccg gtatgttttg | 120 |
| cctcgtcaag agtggacaac gccttaagca catc | 154 |

<210> SEQ ID NO 145
<211> LENGTH: 237
<212> TYPE: DNA
<213> ORGANISM: Artificial Sequence
<220> FEATURE:
<223> OTHER INFORMATION: oligonucleotide probe

<400> SEQUENCE: 145

| aatctggtgt ccgtcatacc cggggagacg cagttgatcg tgatccctg cgggccaagc | 60 |
| tctgcggcga ggtaccgcgc catcgtcgcc agagcgccct tggccgtggc gtaagccgtc | 120 |
| cacccgctca gggggcgcc gtcgatggat ttccgtgta atgcaaacga tgcggcctcc | 180 |
| cccgttatcc gccatgagcg gcgcgaccgc ttggaccgac aggaacgcgc ttttaac | 237 |

```
<210> SEQ ID NO 146
<211> LENGTH: 159
<212> TYPE: DNA
<213> ORGANISM: Artificial Sequence
<220> FEATURE:
<223> OTHER INFORMATION: oligonucleotide probe

<400> SEQUENCE: 146
acagtgtcgt ccaccttcat gcgatcggac gctgccgtca accctgtgac gaagcccgag      60
cagttggctt gcacatcgta gatctgtgcg tgctttgcct cgagctgctg ctgcaccttg     120
gcggagaccg gcggatagat gtagtcccca gagaaggtg                            159

<210> SEQ ID NO 147
<211> LENGTH: 158
<212> TYPE: DNA
<213> ORGANISM: Artificial Sequence
<220> FEATURE:
<223> OTHER INFORMATION: oligonucleotide probe

<400> SEQUENCE: 147
cgcctcattg gggtatctcc aaagtccaat cccatacgct cgccgcgaaa ttgaaccccg      60
cgcccacgcc ggctagcacc acgcgctggc ctcggctcaa cttgcgtttg tgcaccgctt     120
cgctcagtgc gattgcaagc gatgccgagc cagtgtta                             158

<210> SEQ ID NO 148
<211> LENGTH: 196
<212> TYPE: DNA
<213> ORGANISM: Artificial Sequence
<220> FEATURE:
<223> OTHER INFORMATION: oligonucleotide pribe

<400> SEQUENCE: 148
ggctcaactt gcgtttgtgc accgcttcgc tcagtgcgat tgcaagcgat gccgagccag      60
tgttacccac ctcggcgacg ttggcatatg tcttatccaa accgaatccc attttttttca    120 cgaggtattc gatcaagcgc agattcgcct ggtggaacac gacgaagtcg atgtcgctga    180
tctcgtagcc cgactt                                                     196

<210> SEQ ID NO 149
<211> LENGTH: 153
<212> TYPE: DNA
<213> ORGANISM: Artificial Sequence
<220> FEATURE:
<223> OTHER INFORMATION: oligonucleotide probe

<400> SEQUENCE: 149
cacgaggtat tcgatcaagc gcagattcgc ctggtggaac acgacgaagt cgatgtcgct      60
gatctcgtag cccgacttgg cgactgcctt gcgaatggtg gggggcagat gagtgatggc    120
ctgcttccac gtcgcaatac cgttcatctc cat                                  153

<210> SEQ ID NO 150
<211> LENGTH: 150
<212> TYPE: DNA
<213> ORGANISM: Artificial Sequence
<220> FEATURE:
<223> OTHER INFORMATION: oligonuceltode probe

<400> SEQUENCE: 150
gttcgtggga acatcgagc ctccgccgcg ctggcgcacg gcatcgaagt tcgagctgtc       60
cgtgtggaag gcggagtggc ggatgccgcc ttgctgcact cggctcagta cggctgcacc    120
```

```
ggcgccatca ctgaggtata tggcggtgtt                                       150

<210> SEQ ID NO 151
<211> LENGTH: 140
<212> TYPE: DNA
<213> ORGANISM: Artificial Sequence
<220> FEATURE:
<223> OTHER INFORMATION: oligonucleotide probe

<400> SEQUENCE: 151
gtagcggcta agcatttcaa cgccgataac cagcgcgtag cgcacagtgt cgtccaccett    60 catgcgatcg gacgctgccg tcaaccctgt gacgaagccc gagcagttgg cttgcacatc   120
gtagatctgt gcgtgctttg                                                140

<210> SEQ ID NO 152
<211> LENGTH: 197
<212> TYPE: DNA
<213> ORGANISM: Artificial Sequence
<220> FEATURE:
<223> OTHER INFORMATION: oligonucleotide probe

<400> SEQUENCE: 152
aaggtgcaac agataatgac gtctagttgc tcggcggaga cttgcgccat cgccatcgcc    60
tgcttagctg cggccactgc gaaccccac gcggtgtctt gcgggtctgc aatacgcgc    120 tggcggatac cagtttttc ttcgatccag tcaggcgtaa tggcttgtgc cgggtccagc   180
ttctggcaca gctcgtc                                                   197

<210> SEQ ID NO 153
<211> LENGTH: 187
<212> TYPE: DNA
<213> ORGANISM: Artificial Sequence
<220> FEATURE:
<223> OTHER INFORMATION: oligonucleotide probe

<400> SEQUENCE: 153
cttgcgggtc tgcaatacgg cgctggcgga taccagtttt ttcttcgatc cagtcaggcg    60
taatggcttg tgccgggtcc agcttctggc acagctcgtc gttgccgacc actcgcgcag   120
gtaggtggtg gcccactccg acgatggaaa cggcgggcaa tgggacggca gaagtcggaa   180
cagagtt                                                              187

<210> SEQ ID NO 154
<211> LENGTH: 183
<212> TYPE: DNA
<213> ORGANISM: Artificial Sequence
<220> FEATURE:
<223> OTHER INFORMATION: oligonucleotide probe

<400> SEQUENCE: 154
ttttcttcga tccagtcagg cgtaatggct tgtgccgggt ccagcttctg gcacagctcg    60
tcgttgccga ccactcgcgc aggtaggtgg tgcccactc cgacgatgga aacggcgggc   120
aatgggacgg cagaagtcgg aacagagttc atagcgtaaa ggttgcaacc ctctcagtga   180
cag                                                                  183

<210> SEQ ID NO 155
<211> LENGTH: 179
<212> TYPE: DNA
<213> ORGANISM: Artificial Sequence
<220> FEATURE:
<223> OTHER INFORMATION: oligonucleotide probe
```

<400> SEQUENCE: 155

```
gaaactggtt tacggctgac ggcccgctgt gcgggtttat ctgcctggcg gcggtgcgcg      60
acgaggaagt catcgacgat gcgctcgcag tcttgacgat cgatggcacg cagcccggtg     120
aggcgggcga acgccacagg cccgatgagt tgacacagga tcagctccat gtcgaagtc     179
```

<210> SEQ ID NO 156
<211> LENGTH: 149
<212> TYPE: DNA
<213> ORGANISM: Artificial Sequence
<220> FEATURE:
<223> OTHER INFORMATION: oligonucleotide probe

<400> SEQUENCE: 156

```
cctttcgcgc gcatttctga cgagtcaacg cggttcggct cggctaatcg tgacgaacgc      60
gtgttcgccg atcccgacgt gtttgatatc gggcgcaaac ccgaacacca agtggcgttc     120
ggccgaggca ttcacttctg tctgggtgc                                        149
```

<210> SEQ ID NO 157
<211> LENGTH: 168
<212> TYPE: DNA
<213> ORGANISM: Artificial Sequence
<220> FEATURE:
<223> OTHER INFORMATION: oligonucleotide probe

<400> SEQUENCE: 157

```
tgggaagtcg acctagagcg cgcgcaacgc ctgcggtcgg gcccgatccg aggttatctg      60
tcgttgccga tctcgtggtc ggcgaattag ccgcgctgca ggctagtcgg agccgctgcg     120
gcgcgaaact ggtttacggc tgacggcccg ctgtgcgggt ttatctgc                   168
```

<210> SEQ ID NO 158
<211> LENGTH: 157
<212> TYPE: DNA
<213> ORGANISM: Artificial Sequence
<220> FEATURE:
<223> OTHER INFORMATION: oligonucleotide probe

<400> SEQUENCE: 158

```
gctcgcagtc ttgacgatcg atggcacgca gcccggtgag gcgggcgaac gccacaggcc      60
cgatgagttg acacaggatc agctccatgt cgaagtcatc caggtcggcg cgagcttcgg     120
gggctttgca acagggcaac gaacggttgt cgatatt                               157
```

<210> SEQ ID NO 159
<211> LENGTH: 147
<212> TYPE: DNA
<213> ORGANISM: Artificial Sequence
<220> FEATURE:
<223> OTHER INFORMATION: oligonucleotide probe

<400> SEQUENCE: 159

```
acaggcccga tgagttgaca caggatcagc tccatgtcga agtcatccag gtcggcgcga      60
gcttcggggg ctttgcaaca gggcaacgaa cggttgtcga tattggtcga tgatccgcgc     120
gcgcagcgcg tgtcggtcct gggtttc                                          147
```

<210> SEQ ID NO 160
<211> LENGTH: 163
<212> TYPE: DNA
<213> ORGANISM: Artificial Sequence
<220> FEATURE:
<223> OTHER INFORMATION: oligonucleotide probe

```
<400> SEQUENCE: 160
aagccagggt ggtgacatgc agcggggctt cctggaacag cgtggcctgt cggctcaaca      60
gttcgatgag ttggtcgcgc aacgatccag tcgccggtgg ggggtgcacc tgcggcagta     120
gccgctcaaa tgtggcggcc agcagttgag tggagctgct gaa                       163

<210> SEQ ID NO 161
<211> LENGTH: 154
<212> TYPE: DNA
<213> ORGANISM: Artificial Sequence
<220> FEATURE:
<223> OTHER INFORMATION: oligonucleotide probe

<400> SEQUENCE: 161
ggctcaacag ttcgatgagt tggtcgcgca acgatccagt cgccggtggg gggtgcacct      60
gcggcagtag ccgctcaaat gtggcggcca gcagttgagt ggagctgctg aagtggcggt     120
acagggtcgt ccgcgcgact ttggaggcct tggt                                 154

<210> SEQ ID NO 162
<211> LENGTH: 145
<212> TYPE: DNA
<213> ORGANISM: Artificial Sequence
<220> FEATURE:
<223> OTHER INFORMATION: oligonucleotide probe

<400> SEQUENCE: 162
gcagtagccg ctcaaatgtg gcggccagca gttgagtgga gctgctgaag tggcggtaca      60
gggtcgtccg cgcactttg gaggccttgg tgacggcatc gatggtgacg cttcgatgc       120 cgccggcgct caggagtttg gtggc                                           145

<210> SEQ ID NO 163
<211> LENGTH: 170
<212> TYPE: DNA
<213> ORGANISM: Artificial Sequence
<220> FEATURE:
<223> OTHER INFORMATION: oligonucleotide probe

<400> SEQUENCE: 163
ttgagtggag ctgctgaagt ggcggtacag ggtcgtccgc gcactttgg aggccttggt       60 gacggcatcg atggtgacgg cttcgatgcc gccggcgctc aggagtttgg tggccgcatc     120
caagagccgg gttcgtgagc gcagccggcg cgggtcaacg tcgtcatcgt                170

<210> SEQ ID NO 164
<211> LENGTH: 157
<212> TYPE: DNA
<213> ORGANISM: Artificial Sequence
<220> FEATURE:
<223> OTHER INFORMATION: oligonucleotide probe

<400> SEQUENCE: 164
tggacttgga tttctggttg cgccttatgc tgcgatcagc ggtttgcttt gtaccgcaag      60
agctctcggt acgtcatcac accgctacca ccgagtccgc gaacatcacc aagtcccatc     120
ggcactggct ggaccagcta cgcattctga cgtggat                              157

<210> SEQ ID NO 165
<211> LENGTH: 149
<212> TYPE: DNA
<213> ORGANISM: Artificial Sequence
<220> FEATURE:
<223> OTHER INFORMATION: oligonucleotide probe
```

-continued

```
<400> SEQUENCE: 165
gaacatcacc aagtcccatc ggcactggct ggaccagcta cgcattctga cgtggatgat    60
cgtggacccg gcatccacac gcgctgtccg agccgctgca acgccatggt gggcgcttgt   120
ctggctggga ctgctcttca aagtgacgg                                     149

<210> SEQ ID NO 166
<211> LENGTH: 119
<212> TYPE: DNA
<213> ORGANISM: Artificial Sequence
<220> FEATURE:
<223> OTHER INFORMATION: oligonucleotide probe

<400> SEQUENCE: 166
tggtgggaaa tgatgaagcg ggcggcctta cgggacgacg tctttcagac cgtggacttg    60
gatttctggt tgcgccttat gctgcgatca gcggtttgct ttgtaccgca agagctctc    119

<210> SEQ ID NO 167
<211> LENGTH: 172
<212> TYPE: DNA
<213> ORGANISM: Artificial Sequence
<220> FEATURE:
<223> OTHER INFORMATION: oligonucleotide probe

<400> SEQUENCE: 167
gggacgacgt ctttcagacc gtggacttgg atttctggtt gcgccttatg ctgcgatcag    60
cggtttgctt tgtaccgcaa gagctctcgg tacgtcatca caccgctacc accgagtccg   120
cgaacatcac caagtcccat cggcactggc tggaccagct acgcattctg ac           172

<210> SEQ ID NO 168
<211> LENGTH: 138
<212> TYPE: DNA
<213> ORGANISM: Artificial Sequence
<220> FEATURE:
<223> OTHER INFORMATION: oligonucleotide probe

<400> SEQUENCE: 168
cttgtctggc tgggactgct cttcaaagtg acggcgttcg gacctcagcg gtcctcgcgg    60
ctgaaggcgt tgctcgtggc gcccgctagt gagttcgccc gggcgaggcg gtttcgcgct   120
aatcttacgc gtccatcg                                                 138

<210> SEQ ID NO 169
<211> LENGTH: 159
<212> TYPE: DNA
<213> ORGANISM: Artificial Sequence
<220> FEATURE:
<223> OTHER INFORMATION: oligonucleotide probe

<400> SEQUENCE: 169
cggtttcgcg ctaatcttac gcgtccatcg cgatagccaa ctgagaagca cgtcgctctt    60
cgccgtcacc gtccaaaatt cgacgagggc tgcgagcgcc ggtgtacgct caccgcgtgc   120
ctcccctgat gatggccgac agcaacacgc tcgtacatc                          159

<210> SEQ ID NO 170
<211> LENGTH: 150
<212> TYPE: DNA
<213> ORGANISM: Artificial Sequence
<220> FEATURE:
<223> OTHER INFORMATION: oligonucleotide probe

<400> SEQUENCE: 170
```

```
cgtccaaaat tcgacgaggg ctgcgagcgc cggtgtacgc tcaccgcgtg cctccctga    60 tgatggccga cagcaacacg ctcgtacatc gggcgccgcc tgggaccgta ggagctcgca   120
gtatccgatt caggactact cggaagacga                                    150

<210> SEQ ID NO 171
<211> LENGTH: 184
<212> TYPE: DNA
<213> ORGANISM: Artificial Sequence
<220> FEATURE:
<223> OTHER INFORMATION: oligonucleotide probe

<400> SEQUENCE: 171
gtgcctcccc tgatgatggc cgacagcaac acgctcgtac atcgggcgcc gcctgggacc    60
gtaggagctc gcagtatccg attcaggact actcggaaga cgactctgcc catcacaacg   120
ctcgggtctt tgcgcgggac gaatccccgt cttcctcctc ttcatctaca aaattgtgct   180
cggc                                                                184

<210> SEQ ID NO 172
<211> LENGTH: 150
<212> TYPE: DNA
<213> ORGANISM: Artificial Sequence
<220> FEATURE:
<223> OTHER INFORMATION: oligonucleotide probe

<400> SEQUENCE: 172
gagctcgcag tatccgattc aggactactc ggaagacgac tctgcccatc acaacgctcg    60
ggtctttgcg cgggacgaat ccccgtcttc ctcctcttca tctacaaaat tgtgctcggc   120
gaacaggtgc acaaggtgac tggtgtcgac                                    150

<210> SEQ ID NO 173
<211> LENGTH: 140
<212> TYPE: DNA
<213> ORGANISM: Artificial Sequence
<220> FEATURE:
<223> OTHER INFORMATION: oligonucleotide probe

<400> SEQUENCE: 173
tactcggaag acgactctgc ccatcacaac gctcgggtct ttgcgcggga cgaatccccg    60
tcttcctcct cttcatctac aaaattgtgc tcggcgaaca ggtgcacaag gtgactggtg   120
tcgacagcat ttacggcgtg                                               140

<210> SEQ ID NO 174
<211> LENGTH: 160
<212> TYPE: DNA
<213> ORGANISM: Artificial Sequence
<220> FEATURE:
<223> OTHER INFORMATION: oligonucleotide probe

<400> SEQUENCE: 174
tacgactacc caggcaatgt cttttggact gtgcagcaac agcttcgcca gctcgaatca    60
attgggattt tgctctgcct atgcactaag aataacgccg cagatgtgga cgaagtgttt   120
gcgacgcacc ctaacgcggt gctgaaggat gaacacttcg                         160

<210> SEQ ID NO 175
<211> LENGTH: 173
<212> TYPE: DNA
<213> ORGANISM: Artificial Sequence
<220> FEATURE:
<223> OTHER INFORMATION: oligonucleotide probe
```

<400> SEQUENCE: 175

```
ccgaagaagt tgagcgacta cccggcgatg ctgcgcgacg tgaccgcgct ctgcgtggcc      60
ggcggagtag tcagcgagag cgaaaataag acgcgtcact acagactgct ggccgagtca     120
tccgctgcgc aagcgaactt cgcgaatcaa gaggattacc tacgctcgtt gga            173
```

<210> SEQ ID NO 176
<211> LENGTH: 168
<212> TYPE: DNA
<213> ORGANISM: Artificial Sequence
<220> FEATURE:
<223> OTHER INFORMATION: oligonucleotide probe

<400> SEQUENCE: 176

```
actgcgacaa cacgctttgg ggaggcatcg tcggggaaga tgggccgacc ggcatcgggc      60
tcgatccgta cgactaccca ggcaatgtct tttggactgt gcagcaacag cttcgccagc    120
tcgaatcaat tgggattttg ctctgcctat gcactaagaa taacgccg                 168
```

<210> SEQ ID NO 177
<211> LENGTH: 173
<212> TYPE: DNA
<213> ORGANISM: Artificial Sequence
<220> FEATURE:
<223> OTHER INFORMATION: oligonucleotide probe

<400> SEQUENCE: 177

```
tcgaatcaat tgggattttg ctctgcctat gcactaagaa taacgccgca gatgtggacg      60
aagtgtttgc gacgcaccct aacgcggtgc tgaaggatga acacttcgcg ccaagaagg     120 tgaattggga gccgaaggtt gcgaacctgc aagccctagc gaaggagctg aac            173
```

<210> SEQ ID NO 178
<211> LENGTH: 183
<212> TYPE: DNA
<213> ORGANISM: Artificial Sequence
<220> FEATURE:
<223> OTHER INFORMATION: oligonucleotide probe

<400> SEQUENCE: 178

```
ggtgctgaag gatgaacact tcgcggccaa gaaggtgaat tgggagccga aggttgcgaa      60
cctgcaagcc ctagcgaagg agctgaacct cggaccggag agtttcatat ttatcgacga    120
ctccgtattc gagttggagg ccgttcgcgc acagttgccc caagtcaggg tatttcaggt    180
ccc                                                                   183
```

<210> SEQ ID NO 179
<211> LENGTH: 175
<212> TYPE: DNA
<213> ORGANISM: Artificial Sequence
<220> FEATURE:
<223> OTHER INFORMATION: oligonucleotide probe

<400> SEQUENCE: 179

```
ggaccggaga gtttcatatt tatcgacgac tccgtattcg agttggaggc cgttcgcgca      60
cagttgcccc aagtcagggt atttcaggtc ccgaagaagt tgagcgacta cccggcgatg    120
ctgcgcgacg tgaccgcgct ctgcgtggcc ggcggagtag tcagcgagag cgaaa          175
```

<210> SEQ ID NO 180
<211> LENGTH: 152
<212> TYPE: DNA
<213> ORGANISM: Artificial Sequence
```

-continued

```
<220> FEATURE:
<223> OTHER INFORMATION: oligonucleotide probe

<400> SEQUENCE: 180
cagcgagagc gaaaataaga cgcgtcacta cagactgctg gccgagtcat ccgctgcgca        60
agcgaacttc gcgaatcaag aggattacct acgctcgttg gacttggagg tgcgcatcta       120
ccgcgacgcg cgcgagcaga ttccccgcat ag                                     152

<210> SEQ ID NO 181
<211> LENGTH: 172
<212> TYPE: DNA
<213> ORGANISM: Artificial Sequence
<220> FEATURE:
<223> OTHER INFORMATION: oligonucleotide probe

<400> SEQUENCE: 181
catcgctcat ctatcggatt tggacctctg gttgcgtatg ctgctgagat cggcggcttg        60
cttcgtcccg caagaactct cagtacgaca acattccccg tttacggtac aaactttcga       120
tgcacgaccc tggtggcttg accggctgcg ccttctgact tgggtgatcg tt               172

<210> SEQ ID NO 182
<211> LENGTH: 189
<212> TYPE: DNA
<213> ORGANISM: Artificial Sequence
<220> FEATURE:
<223> OTHER INFORMATION: oligonucleotide probe

<400> SEQUENCE: 182
cgactaactg gatcggagag cccaccaacg ttatgttccg gcgtcaactg gcgctcgacg        60
caggaggcat ccgctccgac atcgctcatc tatcggattt ggacctctgg ttgcgtatgc       120
tgctgagatc ggcggcttgc ttcgtcccgc aagaactctc agtacgacaa cattccccgt       180
ttacggtac                                                               189

<210> SEQ ID NO 183
<211> LENGTH: 133
<212> TYPE: DNA
<213> ORGANISM: Artificial Sequence
<220> FEATURE:
<223> OTHER INFORMATION: oligonucleotide probe

<400> SEQUENCE: 183
ctccgacatc gctcatctat cggatttgga cctctggttg cgtatgctgc tgagatcggc        60
ggcttgcttc gtcccgcaag aactctcagt acgacaacat tccccgttta cggtacaaac       120
tttcgatgca cga                                                          133

<210> SEQ ID NO 184
<211> LENGTH: 144
<212> TYPE: DNA
<213> ORGANISM: Artificial Sequence
<220> FEATURE:
<223> OTHER INFORMATION: oligonucleotide probe

<400> SEQUENCE: 184
tcccgcaaga actctcagta cgacaacatt ccccgtttac ggtacaaact ttcgatgcac        60
gaccctggtg gcttgaccgg ctgcgccttc tgacttgggt gatcgttgat cccgcatcac       120
ccatcatgat ccgacttact gcgg                                              144

<210> SEQ ID NO 185
<211> LENGTH: 168
```

```
<212> TYPE: DNA
<213> ORGANISM: Artificial Sequence
<220> FEATURE:
<223> OTHER INFORMATION: oligonucleotide probe

<400> SEQUENCE: 185
acttactgcg ggaatgtggt gggtgcccgt ctggctgcta cgagctctag aagtcattgt      60
ctacgggccg acagagtct cacggatgaa aacgttgatg ctcgccccg tccgtgagtt      120 cgcccgagcc cggcggctcc gtgccaacct gaggtggaag gagtcgta               168

<210> SEQ ID NO 186
<211> LENGTH: 150
<212> TYPE: DNA
<213> ORGANISM: Artificial Sequence
<220> FEATURE:
<223> OTHER INFORMATION: oligonucleotide probe

<400> SEQUENCE: 186
cttctgactt gggtgatcgt tgatcccgca tcacccatca tgatccgact tactgcggga      60
atgtggtggg tgcccgtctg ctgctacga gctctagaag tcattgtcta cgggccggac      120
agagtctcac ggatgaaaac gttgatgctc                                      150

<210> SEQ ID NO 187
<211> LENGTH: 181
<212> TYPE: DNA
<213> ORGANISM: Artificial Sequence
<220> FEATURE:
<223> OTHER INFORMATION: oligonucleotide probe

<400> SEQUENCE: 187
cgcgatataa gcatctcaat gtaccccgcc gaggtacacc gtctgcgcag tgatacaccc      60
gctgccaggt ccacaaaaga aatcgagcac atgcgccacg tcttcacgcg tcgccatgcg      120
cgcaagcggc aggcggcgat cacggcattg actttatcgc gcggtagctg gcttaacatg      180
t                                                                     181

<210> SEQ ID NO 188
<211> LENGTH: 167
<212> TYPE: DNA
<213> ORGANISM: Artificial Sequence
<220> FEATURE:
<223> OTHER INFORMATION: oligonucleotide probe

<400> SEQUENCE: 188
gcctacatgg tcgaagtggc cgtgagtgca cagcacagct tcaggggccc agtcgaggtc      60
gttcagcttc ttctccaacg acgcggaatc cagtcctggg tcgacgatca cacaacgacc      120
aggtgcgcca gaggctaaaa gatacgtatt tgaggaaaag ccttggt                  167

<210> SEQ ID NO 189
<211> LENGTH: 155
<212> TYPE: DNA
<213> ORGANISM: Artificial Sequence
<220> FEATURE:
<223> OTHER INFORMATION: oligonucleotide probe

<400> SEQUENCE: 189
tcagcttctt ctccaacgac gcggaatcca gtcctgggtc gacgatcaca caacgaccag      60
gtgcgccaga ggctaaaaga tacgtatttg aggaaaagcc ttggtttgcc acgatttgca      120
aagcgccggc gctggtagtc atttctgtca ggccg                               155
```

```
<210> SEQ ID NO 190
<211> LENGTH: 156
<212> TYPE: DNA
<213> ORGANISM: Artificial Sequence
<220> FEATURE:
<223> OTHER INFORMATION: oligonucleotide probe

<400> SEQUENCE: 190
gcgctggtag tcatttctgt caggccgcct ccgtgcagca gcgtcgaagg cgctgcacaa      60
acgatgttga acgcgatata agcatctcaa tgtaccccgc cgaggtacac cgtctgcgca     120
gtgatacacc cgctgccagg tccacaaaag aaatcg                               156

<210> SEQ ID NO 191
<211> LENGTH: 153
<212> TYPE: DNA
<213> ORGANISM: Artificial Sequence
<220> FEATURE:
<223> OTHER INFORMATION: oligonucleotide probe

<400> SEQUENCE: 191
cacggcattg actttatcgc gcggtagctg gcttaacatg tcagtttcga aggcgctgat      60
cccgagcgtg ttacaggtga tgttcgtggt ggccagttcc tttgccatta tgttggcgag     120
agtggtgacc gcagccttgg tggcagcgta gac                                  153

<210> SEQ ID NO 192
<211> LENGTH: 170
<212> TYPE: DNA
<213> ORGANISM: Artificial Sequence
<220> FEATURE:
<223> OTHER INFORMATION: oligonucleotide probe

<400> SEQUENCE: 192
attatgttgg cgagagtggt gaccgcagcc ttggtggcag cgtagaccga gtcgcccatg      60
ggctctaggc tcacggccat cgagctcacg ctgacgatgc gacccatttt acccttgcgc     120
atgagcttcg cggcctcgcg tgagacgagg aacgtgccta acaaattcgt                170

<210> SEQ ID NO 193
<211> LENGTH: 144
<212> TYPE: DNA
<213> ORGANISM: Artificial Sequence
<220> FEATURE:
<223> OTHER INFORMATION: oligonucleotide probe

<400> SEQUENCE: 193
cgtgagacga ggaacgtgcc taacaaattc gtttcgacca tggcctgggc cgacgcggcc      60
ggcagtatca ttgcgtactg cgaggtcagc acagcggcgt tgttgacgca gatgtccagc     120
ttgccgaaac gcttgcgaat ttct                                            144

<210> SEQ ID NO 194
<211> LENGTH: 145
<212> TYPE: DNA
<213> ORGANISM: Artificial Sequence
<220> FEATURE:
<223> OTHER INFORMATION: oligonucleotide probe

<400> SEQUENCE: 194
catcgagctc acgctgacga tgcgacccca tttacccttg cgcatgagct tcgcggcctc      60
gcgtgagacg aggaacgtgc ctaacaaatt cgtttcgacc atggcctggg ccgacgcggc     120
cggcagtatc attgcgtact gcgag                                           145
```

```
<210> SEQ ID NO 195
<211> LENGTH: 156
<212> TYPE: DNA
<213> ORGANISM: Artificial Sequence
<220> FEATURE:
<223> OTHER INFORMATION: oligonucoeltode probe

<400> SEQUENCE: 195
cgaccccatt taccottgcg catgagcttc gcggcctcgc gtgagacgag gaacgtgcct      60
aacaaattcg tttcgaccat ggcctgggcc gacgcggccg gcagtatcat tgcgtactgc     120
gaggtcagca cagcggcgtt gttgacgcag atgtcc                               156

<210> SEQ ID NO 196
<211> LENGTH: 134
<212> TYPE: DNA
<213> ORGANISM: Artificial Sequence
<220> FEATURE:
<223> OTHER INFORMATION: oligonucleotide probe

<400> SEQUENCE: 196
gacttgggaa cttcatcgac atggcgacta aaccccacca cgtgcgcccc gcgccgctcg      60
aaatgttcag cgaccacggc gcccagaccc cgacgcgcgc cggttaccaa caccacctt     120 tcgtcatagc ttgc                                                       134

<210> SEQ ID NO 197
<211> LENGTH: 181
<212> TYPE: DNA
<213> ORGANISM: Artificial Sequence
<220> FEATURE:
<223> OTHER INFORMATION: oligonucleotide probe

<400> SEQUENCE: 197
accagcgctg actgaacttg cgtccccgat gtcgacggct acgtcgtagc gacggtccga      60
cttgggaact tcatcgacat ggcgactaaa ccccaccacg tgcgcccgc gccgctcgaa     120 atgttcagcg accacggcgc ccagaccccg acgcgcgccg gttaccaaca ccaccttttc     180
g                                                                     181

<210> SEQ ID NO 198
<211> LENGTH: 152
<212> TYPE: DNA
<213> ORGANISM: Artificial Sequence
<220> FEATURE:
<223> OTHER INFORMATION: oligonucleotide probe

<400> SEQUENCE: 198
cgatcgtcgt agctgatgtg catagtcagc gcgacagccg ccaggcctag caccagcgcc      60
agactggcga ccaatagcgg cacgggtcga cggaccaccg ccacggcgat ccagttccag     120
tagcggcgag tgcgatctgc cttgggttca cc                                   152

<210> SEQ ID NO 199
<211> LENGTH: 173
<212> TYPE: DNA
<213> ORGANISM: Artificial Sequence
<220> FEATURE:
<223> OTHER INFORMATION: oligonucleotide probe

<400> SEQUENCE: 199
ggtagccgaa agctgctgta gcagcggacg gaaccgctgg acttgggatc cactggattg      60 gcttgggtg aggagtccgg tcaacggggt caacgcggtg cgcaaggtgg tgtccagttg     120
cgcgagaccg ccggcgagtt ggtcggcgcc gtgggtgagt ttggccaggt cat            173
```

<210> SEQ ID NO 200
<211> LENGTH: 152
<212> TYPE: DNA
<213> ORGANISM: Artificial Sequence
<220> FEATURE:
<223> OTHER INFORMATION: oligonucleotide probe

<400> SEQUENCE: 200
ctggacttgg gatccactgg attgggcttg ggtgaggagt ccggtcaacg gggtcaacgc    60
ggtgcgcaag gtggtgtcca gttgcgcgag accgccggcg agttggtcgg cgccgtgggt   120
gagtttggcc aggtcatcct tgtgtgcgtc tc                                 152

<210> SEQ ID NO 201
<211> LENGTH: 157
<212> TYPE: DNA
<213> ORGANISM: Artificial Sequence
<220> FEATURE:
<223> OTHER INFORMATION: oligonucleotide probe

<400> SEQUENCE: 201
aaggtggtgt ccagttgcgc gagaccgccg gcgagttggt cggcgccgtg ggtgagtttg    60
gccaggtcat ccttgtgtgc gtctcccttg gcgaccgcgc cggccatctt gtcgccaatc   120
tcgccgtttt gccacgacag ttgagcctgg tccagac                            157

<210> SEQ ID NO 202
<211> LENGTH: 123
<212> TYPE: DNA
<213> ORGANISM: Artificial Sequence
<220> FEATURE:
<223> OTHER INFORMATION: oligonucleotide probe

<400> SEQUENCE: 202
gagaggccat ttcatccagg tcggccaggg ccttgctggt gcgcatatcg gtgggcgatt    60
cgacgaccat gaattcggtg acgatggcgt ccttgcgaaa gtgcctgtcc agcagtcgat   120
atc                                                                 123

<210> SEQ ID NO 203
<211> LENGTH: 175
<212> TYPE: DNA
<213> ORGANISM: Artificial Sequence
<220> FEATURE:
<223> OTHER INFORMATION: oligonucleotide probe

<400> SEQUENCE: 203
gtcgatatcc ctcattgctg gccgtggtcg ccggctgtcc tcggcgatcg tcgtagctga    60
tgtgcatagt cagcgcgaca gccgccaggc ctagcaccag cgccagactg gcgaccaata   120
gcggcacggg tcgacggacc accgccacgg cgatccagtt ccagtagcgg cgagt        175

<210> SEQ ID NO 204
<211> LENGTH: 27
<212> TYPE: DNA
<213> ORGANISM: Artificial Sequence
<220> FEATURE:
<223> OTHER INFORMATION: oligonucleotide probe

<400> SEQUENCE: 204
atacgtgccc agaagctcta ccgagat                                        27

<210> SEQ ID NO 205
<211> LENGTH: 167

<212> TYPE: DNA
<213> ORGANISM: Mycobacterium intracellulare
<220> FEATURE:
<221> NAME/KEY: misc_feature
<223> OTHER INFORMATION: rps1

<400> SEQUENCE: 205
cgggacaagg tcgccaaggt caagaccgcg gcgctcaagg gcagcccgca gcgccgtggc    60
gtatgcaccc gcgtgtacac caccactccg aagaagccga actccgctct tcggaaggtc   120
gcccgcgtga agctgacgag ccaggttgag gtgacggcct acatccc                 167

<210> SEQ ID NO 206
<211> LENGTH: 168
<212> TYPE: DNA
<213> ORGANISM: Mycobacterium bovis
<220> FEATURE:
<221> NAME/KEY: misc_feature
<223> OTHER INFORMATION: IS6110

<400> SEQUENCE: 206
acctcaccta tgtgtcgacc tgggcagggt tcgcctacgt ggcctttgtc accgacgcct    60
acgctcgcag gatcctgggc tggcgggtcg cttccacgat ggccacctcc atggtcctcg   120
acgcgatcga gcaagccatc tggacccgcc aacaagaaag cgtactcg                168

<210> SEQ ID NO 207
<211> LENGTH: 236
<212> TYPE: DNA
<213> ORGANISM: Mycobacterium kansasii
<220> FEATURE:
<221> NAME/KEY: misc_feature
<223> OTHER INFORMATION: KATS2 sequence

<400> SEQUENCE: 207
gtccctggct gctcttgacc gccatagctc gatcgaaatg cctacgggca gtgagcaaat    60
cacccatcgt atccaccatc ctcgacagcg tggtggtatt cgtcccgaaa gtgggacgtc   120
cgcctcatga cgttgtgccg caacgttgat cgagtcactg tgtagcaatc gacatggtga   180
cgggttcgag gctgacgtaa cggttctcgg cgcggaacat ctccatctcc accagc       236

<210> SEQ ID NO 208
<211> LENGTH: 111
<212> TYPE: DNA
<213> ORGANISM: Mycobacterium avium
<220> FEATURE:
<221> NAME/KEY: misc_feature
<223> OTHER INFORMATION: MAV19K

<400> SEQUENCE: 208
cggctgttcg agtggcaaca agtcggctcc cagcagttcc gcgagcagct cgagcaccag    60
tccgtcggcg agcagcggcg gggcggccgg gaccaaggtc atcatcgacg g            111

What is claimed is:

1. An isolated or purified oligonucleotide comprising:
 a nucleotide sequence selected from the nucleotide sequence of SEQ ID NO: 1 or the sequence complementary to the nucleotide sequence of SEQ ID NO: 1, wherein the oligonucleotide is no more than about 700 nucleotides in length, and wherein the oligonucleotide is capable of hybridizing with a nucleotide sequence of a *Mycobacterium intracellulare* gene.

2. A primer for detecting *Mycobacterium intracellulare* comprising:
 an oligonucleotide consisting of the nucleotide sequence of SEQ ID NO: 9 or 10, or the sequence complementary to the nucleotide sequence of SEQ ID NO: 9 or 10, wherein the primer is no more than about 25 nucleotides in length, and wherein the oligonucleotide is capable of hybridizing with a nucleotide sequence of a *Mycobacterium intracellulare* gene.

3. The primer according to claim 2, wherein the primer is labeled with a labeling substance.

4. The primer according to claim 3, wherein the labeling substance is selected from a radioisotope, an enzyme, a fluorescent substance, a luminescent substance, and biotin.

5. A probe for detecting *Mycobacterium intracellulare* comprising:
 an oligonucleotide consisting of the nucleotide sequence of:
 SEQ ID NO: 9, 10, or 204, or the sequence complementary to the nucleotide sequence of SEQ ID NO: 9, 10, or 204, wherein the probe is no more than about 50 nucleotides in length; or
 SEQ ID NO: 1 or 139, or the sequence complementary to the nucleotide sequence of SEQ ID NO: 1 or 139, wherein the probe is no more than about 700 nucleotides in length; and
 wherein the oligonucleotide is capable of hybridizing with a nucleotide sequence of a *Mycobacterium intracellulare* gene.

6. The probe according to claim 5, wherein the probe is labeled with a labeling substance.

7. The probe according to claim 6, wherein the labeling substance is selected from a radioisotope, an enzyme, a fluorescent substance, a luminescent substance, and biotin.

8. A reagent kit for detecting *Mycobacterium intracellulare*, comprising:
 at least one of a primer, a pair of primers, or a probe;
 wherein the primer comprises an oligonucleotide consisting of the nucleotide sequence of SEQ ID NO: 9 or 10, or the sequence complementary to the nucleotide sequence of SEQ ID NO: 9 or 10, wherein the primer is no more than about 25 nucleotides in length, and wherein the oligonucleotide is capable of hybridizing with a nucleotide sequence of a *Mycobacterium intracellulare* gene;
 wherein the pair of primers comprises a first primer comprising an oligonucleotide consisting of the nucleotide sequence of SEQ ID NO: 9 or the complementary sequence thereof, and a second primer comprising an oligonucleotide consisting of the nucleotide sequence of SEQ ID NO:10 or the complementary sequence thereof, wherein the primers are no more than about 25 nucleotides in length, wherein the oligonucleotides are capable of hybridizing with a nucleotide sequence of a *Mycobacterium intracellulare* gene, and wherein the first and second primers can operate together to produce a nucleic acid amplification product; and
 wherein the probe comprises an oligonucleotide consisting of the nucleotide sequence of:
 SEQ ID NO: 9, 10, or 204, or the sequence complementary to the nucleotide sequence of SEQ ID NO: 9, 10, or 204, wherein the probe is no more than about 50 nucleotides in length; or
 SEQ ID NO: 1 or 139, or the sequence complementary to the nucleotide sequence of SEQ ID NO: 1 or 139, wherein the probe is no more than about 700 nucleotides in length; and wherein the oligonucleotide is capable of hybridizing with a nucleotide sequence of a *Mycobacterium intracellulare* gene.

9. The probe according to claim 5, wherein the probe is labeled with a reporter fluorescent dye and with a quencher dye.

10. The probe according to claim 9, wherein the 5'-terminal of the probe is labeled with the reporter fluorescent dye and the 3'-terminal of the probe is labeled with the quencher dye.

* * * * *